United States Patent
Sonnenschein et al.

(10) Patent No.: US 7,156,863 B2
(45) Date of Patent: *Jan. 2, 2007

(54) FUNDOPLICATION APPARATUS AND METHOD

(75) Inventors: Elazar Sonnenschein, Beersheva (IL); Minelu Zonnenshein, Beersheva (IL); Randal Chinnock, Sturbridge, MA (US); Lawrence Crainich, Charlestown, NH (US)

(73) Assignee: Medigus Ltd., Omer (IL)

( * ) Notice: Subject to any disclaimer, the term of this patent is extended or adjusted under 35 U.S.C. 154(b) by 1373 days.

This patent is subject to a terminal disclaimer.

(21) Appl. No.: 09/809,291

(22) Filed: Mar. 15, 2001

(65) Prior Publication Data

US 2001/0056282 A1 Dec. 27, 2001

(30) Foreign Application Priority Data

| Mar. 16, 2000 | (IL) | 135117 |
| Sep. 21, 2000 | (IL) | 138632 |
| Nov. 20, 2000 | (IL) | 139788 |
| Feb. 26, 2001 | (IL) | 141665 |

(51) Int. Cl.
*A61B 17/068* (2006.01)
*A61B 1/005* (2006.01)

(52) U.S. Cl. ............ 606/219; 606/142; 606/143; 227/181.1; 600/130; 600/106

(58) Field of Classification Search .......... 600/173, 600/117, 130; 606/219, 142, 143; 227/181.1, 227/175.1, 179.1
See application file for complete search history.

(56) References Cited

U.S. PATENT DOCUMENTS

| 3,889,662 A | 6/1975 | Mitsui |
| 4,612,933 A | 9/1986 | Brinkerhoff et al. |
| 4,848,637 A | 7/1989 | Pruitt |
| 5,129,570 A | 7/1992 | Schulze et al. |
| 5,181,514 A | 1/1993 | Solomon et al. |

(Continued)

FOREIGN PATENT DOCUMENTS

DE 4241938 6/1994

(Continued)

OTHER PUBLICATIONS

Christensen, Douglas A., "Ultrasonic Bioinstrumentation," p. 131.

(Continued)

*Primary Examiner*—John P. Leubecker
(74) *Attorney, Agent, or Firm*—Roach Brown McCarthy & Gruber, P.C.; Kevin D. McCarthy

(57) ABSTRACT

An endoscopic device for the partial fundoplication for the treatment of GERD, comprises: a) a distal bending portion and a flexible portion suitable to be positioned in extended shape within the esophagus of a subject; b) a positioning assembly comprising two separate elements, one of which is located on said distal bending portion, and the other on said flexible portion; c) a stapling assembly comprising a staple ejecting device, wherein said staple ejecting device is located on either said bending portion or on said flexible portion, said staple ejecting devices being in working positioned relationship when said two separate elements of said positioning assembly are aligned; and d) circuitry for determining when said two separate elements of said positioning assembly are aligned.

55 Claims, 59 Drawing Sheets

U.S. PATENT DOCUMENTS

| | | |
|---|---|---|
| 5,197,649 A | 3/1993 | Bessler et al. |
| 5,259,837 A | 11/1993 | Van Wormer |
| 5,395,030 A | 3/1995 | Kuramoto et al. |
| 5,403,326 A | 4/1995 | Harrison et al. |
| 5,411,508 A | 5/1995 | Bessler et al. |
| 5,441,507 A | 8/1995 | Wilk |
| 5,445,144 A | 8/1995 | Wodicka et al. |
| 5,452,836 A | 9/1995 | Huitema et al. |
| 5,558,665 A | 9/1996 | Kieturakis |
| 5,571,116 A | 11/1996 | Bolanos et al. |
| 5,603,443 A | 2/1997 | Clark et al. |
| 5,630,540 A | 5/1997 | Blewett |
| 5,630,541 A | 5/1997 | Williamson, IV et al. |
| 5,676,674 A | 10/1997 | Bolanos et al. |
| 5,727,553 A | 3/1998 | Saad |
| 5,772,099 A | 6/1998 | Gravener |
| 5,772,673 A | 6/1998 | Cuny et al. |
| 5,776,049 A | 7/1998 | Takahashi |
| 5,787,897 A | 8/1998 | Kieturakis |
| 5,814,055 A | 9/1998 | Knodel et al. |
| 5,833,616 A | 11/1998 | Gruner et al. |
| 5,833,696 A | 11/1998 | Whitfield et al. |
| 5,897,562 A | 4/1999 | Bolanos et al. |
| 5,906,578 A | 5/1999 | Rajan et al. |
| 6,056,695 A | 5/2000 | Rupp et al. |
| 6,059,719 A | 5/2000 | Yamamoto et al. |
| 6,090,120 A | 7/2000 | Wright et al. |
| 6,099,542 A | 8/2000 | Cohn et al. |
| 6,149,598 A | 11/2000 | Tanaka |
| 6,159,146 A | 12/2000 | El Gazayerli |
| 6,312,437 B1 * | 11/2001 | Kortenbach .................. 606/139 |
| 6,338,737 B1 | 1/2002 | Toledano |
| 6,506,196 B1 * | 1/2003 | Laufer ........................ 606/142 |
| 6,632,227 B1 | 10/2003 | Adams |
| 6,663,639 B1 | 12/2003 | Laufer et al. |
| 6,695,198 B1 | 2/2004 | Adams et al. |
| 6,716,233 B1 | 4/2004 | Whitman |
| 6,736,828 B1 | 5/2004 | Adams et al. |
| 2001/0054636 A1 | 12/2001 | Nicolo |

FOREIGN PATENT DOCUMENTS

| | | |
|---|---|---|
| EP | 0630612 | 12/1994 |
| JP | 11047079 | 2/1999 |
| WO | 8911252 | 11/1989 |
| WO | 9100049 | 1/1991 |
| WO | 9747231 | 12/1997 |
| WO | 9953838 | 10/1999 |
| WO | 0053102 | 9/2000 |
| WO | 0167964 | 9/2001 |

OTHER PUBLICATIONS

Kino, Gordon S., "Acoustic Waves: Devices, Imaging, and Analog Signal Processing," Prentice-Hall, Inc., New Jersey, 1987, pp. 175, 220-225.

Proakis, John G. and Dimitris G. Manolakis, "Digital Signal Processing," Prentice-Hall, Inc., New Jersey, 1996, pp. 30, 130-131.

Seto, William W., "Schaum's Outline of Theory and Problems of Acoustics," McGraw-Hill, Inc., New York, 1971, pp. 13-14.

"The Esophagus, "(Donald O. Castell, ed., Lippincott Williams & Wilkins, 3d ed. 1999), pp. 515-517.

U.S. Appl. No. 10/036,171, filed Dec. 31, 2001.

European International Search Report.

"Physical Principles of Medical Ultrasonics," Editor, C.R.Hill, Ellis Horwood Series in Applied Physics, John Wiley &Sons, NY 1986.

"Physical Principles of Medical Ultrasonics," Editor, C.R.Hill, Ellis Horwood Series in Applied Physics, John Wiley & Sons, NY 1986, pp. 205-206, 327-329.

* cited by examiner

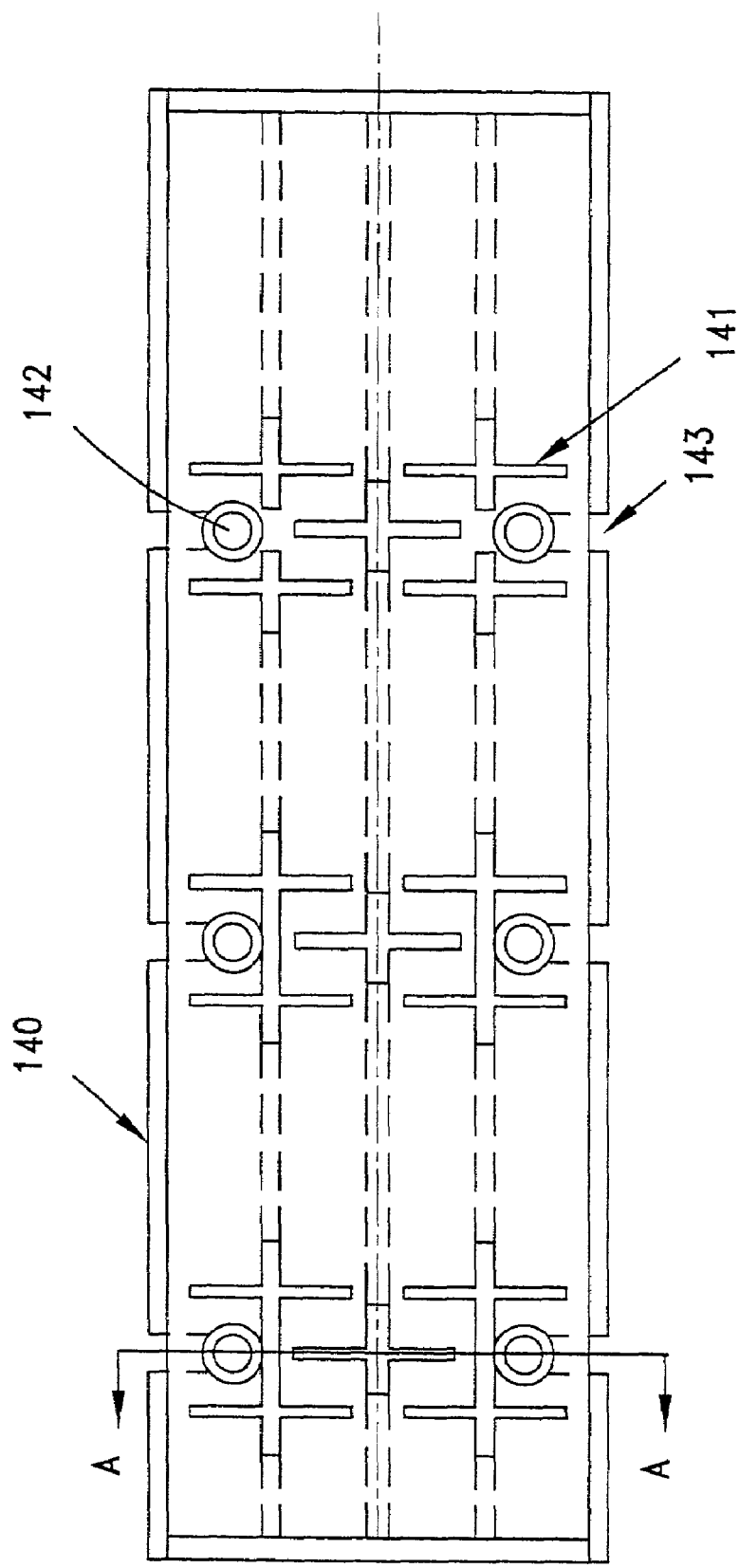

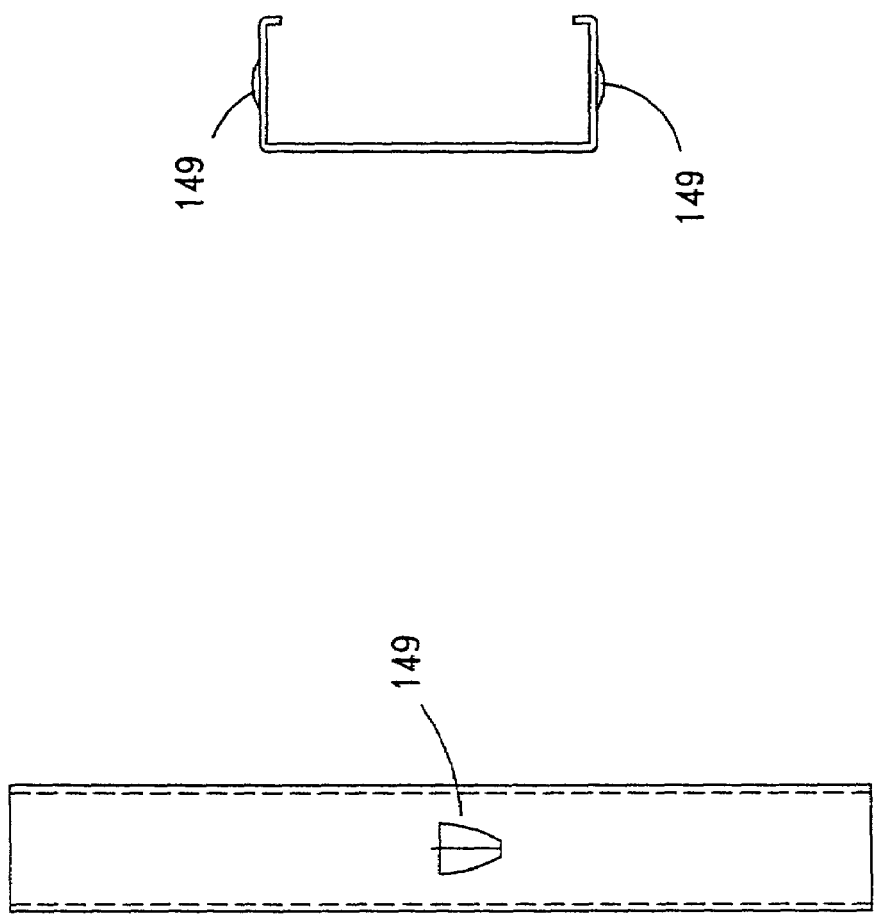

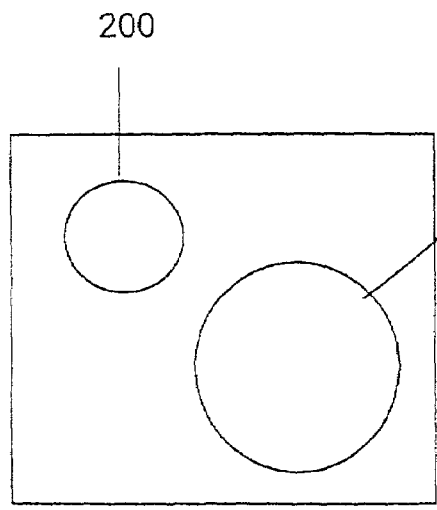
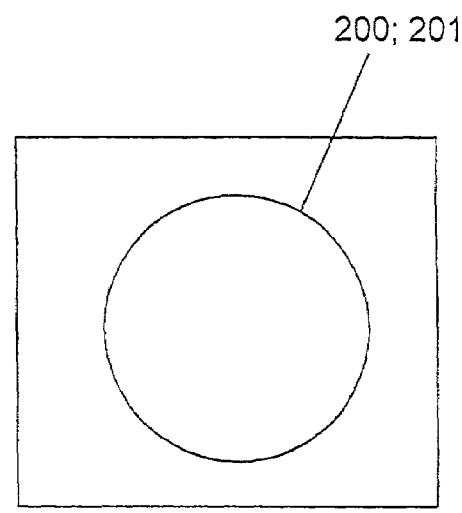
Fig. 29A    Fig. 29B
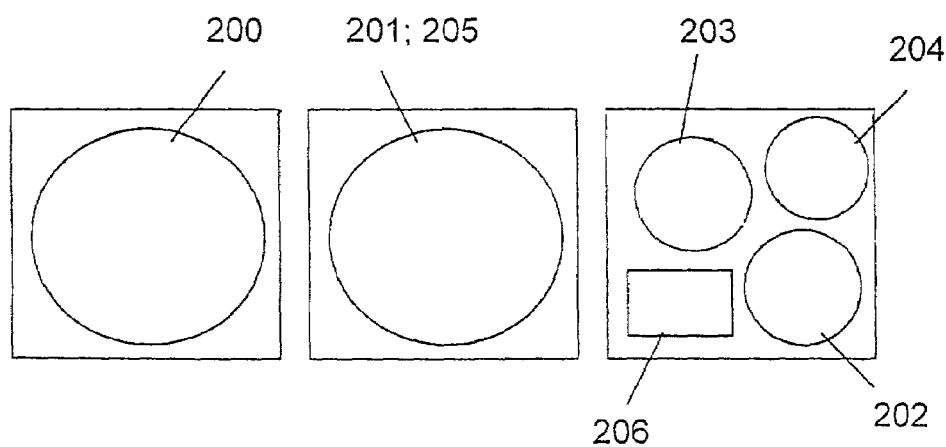
Fig. 29C

FUNDOPLICATION APPARATUS AND METHOD

FIELD OF THE INVENTION

The present invention relates to endoscopic apparatus. More particularly, the invention relates to an apparatus and a method for the endoscopic fundoplication for the treatment of gastroesophageal reflux disease (GERD).

BACKGROUND OF THE INVENTION

GERD is caused by abnormal regurgitation of acid fluids from the stomach into the esophagus. The stomach generates strong acids to aid digestion. The esophagus is normally protected from these acids by a one-way valve mechanism at its junction with the stomach. This one-way valve is called the lower esophageal sphincter (LES). In patients with GERD, the LES frequently malfunctions because it is either too weak or too short. The short or weak LES cannot retain the contents of the stomach as it fills up and pressure inside rises.

When the LES falls, acid flows backwards—refluxes—up into the esophagus which is not designed to handle it. The result is an acid burn, commonly called "heartburn", or "acid indigestion". Heartburn feels like a burning or pressure pain behind the breastbone—it may feel very much like a heart attack. When the acid is in the esophagus, and one belches, it may regurgitate up into the back of the throat, tasting sour or bitter, and causing a burning sensation. If this occurs at night, one may wake-up with either a hot, fiery feeling in the back of the throat, or even coughing and gasping resulting from acid entering the breathing tubes. This last phenomenon is called Reflux Nocturnal Aspiration and can be quite serious in itself.

Reflux Nocturnal Aspiration can be dangerous, because it introduces acid and bacteria into the airway and lungs. This can cause recurrent bronchitis, pneumonia, lung abscess, or chronic scarring of the lung. It can also lead to asthma attacks in those with an asthmatic tendency.

When acid reflux and these symptoms occur daily or up to three or four times weekly, the esophagus cannot withstand the damaging effects of the acid bath and becomes inflamed, especially at its lower part. Swallowing can frequently be painful, and food may stick in the chest. This is called reflux esophagitis, meaning inflammation of the esophagus due to acid reflux. Persistent esophagitis can cause erosions and ulcers and lead to scarring and narrowing and also irreversible injury to the esophagus.

In some patients, as the esophageal lining becomes increasingly damaged and the body may attempt to try to protect it by changing the lining material to a more resistant type, such as found in the intestine. This change, called Barrett's Esophageal Metaplasia, or Barrett's Esophagus, does not make the symptoms disappear but actually produces a new problem. Metaplastic changes increase the risk of a cancer forming in the new and abnormal lining. Adenocarcinoma of the Gastroesophageal Cardia is a highly malignant and fatal type of cancer, the incidence of which is increasing rapidly in America. Some authorities believe that Barrett's esophagus is caused by bile reflux and that the rising incidence of this particular type of cancer is due to the increasing use of medication that suppresses acid production, thus allowing the alkaline bile to reflux unopposed into the esophagus.

The symptoms of acid reflux are uncomfortable, and some sort of relief is usually sought. Some patients chew antacid tablets, sleep on several pillows, or even sleep upright in a recliner. Those with frequent symptoms are treated with drugs that interfere with the formation of acid in the stomach such as Tagamet®, Zantac®, Pepcid®, and Prilosec®. These medications work well in relieving symptoms, till the next dose is due, but they have to be taken daily, often for life, and the cost is substantial (around $1,300 per patient per year).

Moreover, these medications relieve the symptoms, but do not correct the underlying problem.

Currently, the only way to restore the valve function is to operate under a general anesthetic. In the past, the operation was a complex undertaking, entailing a large abdominal or thoracic incision, a lengthy stay in hospital, and a prolonged absence from work. Today, the operation can be done laparoscopically. This shortens the hospital stay, from about ten days to two or three days, but is still carried on under a general anesthetic, and is associated with a significant complication rate, Therefore gastroenterologists are often reluctant to refer patients to surgeons for anti-reflux surgery and many patients who should be operated upon are not.

It is estimated that in the USA alone, 65 million people suffer from heartburn and GERD symptoms are currently the most common complaint of patients who consult with gastroenterologists. According to the New England Journal of Medicine, nearly 40% of adult Americans suffer from heartburn; of those who seek treatment for symptoms of reflux esophagitis, 10 to 20% have serious complications (about 4–8% of the total adult population).

THE PRIOR ART

Surgical Treatment of Reflux Esophagitis

Surgical procedures are usually effective in controlling severe gastresophageal reflux disease. Surgical procedures are designed to correct gastroesophageal reflux by creating a new functional lower esophageal sphincter and to repair a hiatal hernia when present. The most popular approach is the Nissen fundoplication or a modification of this technique [*The Esophagus*, $3^{rd}$ Ed., Donald O. Castell, Ed., pp. 515–517]. It involves mobilization and wrapping of the fundus of the stomach around the lower esophagus. As pressure increases in the stomach it compresses the lower esophagus, preventing reflux. The procedure is performed after first placing a large dilator in the esophagus in order to prevent making the wrap too tight. Fundoplication performed by either a traditional open or laparoscopic technique should be identical, except that access to the esophagus by laparoscopy is through a series of four or five punctures, rather than by an upper abdominal incision. The advantages of the open technique include the ability to see structures in three dimensions and to palpate them. Laparoscopy provides a clear magnified view of the area of surgery and is associated with less pain and more rapid recovery postoperatively.

This procedure is illustrated in FIG. 1. The length of the suture "S" is 2.5 to 3.0 cm, and 2 to 5 sutures are typically required. Because wrapping the stomach "ST" 360 degrees around the esophagus "E", as shown in FIG. 1, is associated with inability or difficulty in belching and vomiting, partial fundoplications have been devised. These include the Toupet posterior partial fundoplication (270 degrees) [Ibid, pp. 517–518] illustrated in FIG. 2, in which "F" is the esophagus, AW is the anterior wall of wrap sutured to the esophagus, and "GJ" is the gastroesophageal junction, and the Thal anterior fundoplication (180 degrees), illustrated in FIG. 3, where "F" indicates the fundus being plicated.

All these procedures have an excellent track record in terms of safety, and ability to control both biliary and acid reflux. However, they can only be carried out laparoscopically or via a laparotomy (abdominal incision) or a thoracotomy (opening the chest). Either way, general anesthesia is required. Because of this disadvantage, the art has attempted do devise minimally invasive methods and apparatus that can be used to carry out fundoplication procedures. U.S. Pat. No. 5,403,326 describes a fundoplication method of the stomach to the esophagus that requires the introduction of an esophageal manipulator and a stapler into the stomach lumen, and the stapling the intussusception esophagus to the stomach. U.S. Pat. No. 5,558,665, and its related patent U.S. Pat. No. 5,787,897, disclose a variform intraluminal member that can be used to manipulate the fundus to a position where it can be fastened by other devices, and a method for carrying out such surgery. U.S. Pat. No. 5,571,116, and its related U.S. Pat. Nos. 5,676,674 and 5,897,562 describe a multi-stapler device, and associated staplers, for carrying out an automatic approximation of the lower esophagus and fundus of the stomach and for invaginating the gastroesophageal junction into the stomach, thereby involuting the surrounding fundic wall.

WO 00/53102 describes a method and apparatus for minimally-invasive fundoplication which requires to use a gripping head to grip the fundus and to move it toward the esophagus. The device of this reference has the severe drawback of being unable to position the stapling head precisely, and therefore any attempt to carry out a fundoplication may result in dangerous damage being inflicted on the patient. Furthermore, it entails an undesirable perforation of the fundus by the gripping head.

Many types of surgical stapling instruments have been devised for different surgical procedures. Typical designs of basic surgical staplers are disclosed in, for example, U.S. Pat. No. 5,129,570 and U.S. Pat. No. 5,630,541. U.S. Pat. No. 5,452,836 and U.S. Pat. No. 5,603,443 disclose staple designs in which the staple dispensing part and the anvil are separated.

U.S. Pat. No. 5,197,649 and U.S. Pat. No. 5,395,030 describe surgical staplers that have been developed for connecting the severed edges of tubular tissue such as that of the intestines.

Many other stapler designs are disclosed in the prior art. Many of these are specialized devices that are suitable for performing only the type of procedure for which they have been designed. Most of these are very difficult and time consuming to work with, requiring a great deal of skill to manipulate the tissues and the stapling device.

A basic consideration in the design of all staplers is the fact that it takes a substantial force to bend the staples. Consequently, at the time the staples are fired, the anvil and the head must be clamped rigidly together, or the force will cause them to separate, and the staples will not bend. In addition, for the staples to bend to the shape required to hold the tissues together, the anvil and the staple dispensing part must be aligned precisely. Because of these limitations, the distal stapler holding and anvil portions of the device are typically rigidly pivotally connected together in existing staplers. In staplers where the anvil and staple dispensing parts are separate, clamping is done manually at the desired location for stapling, which often necessitates physical manual contact with the tissues to be stapled together.

With current stapling methods, it is impossible to hold the aforementioned parts rigidly together unless they are rigidly or pivotally connected at the time of placement.

Endoscopy is a mature class of surgery that came into wide use after the invention of the Hopkins "rod-lens" relay system in the 1960s. Prior to this breakthrough, endoscopes provided very poor image quality coupled with an inability to provide and transmit adequate illumination and were not suitable for most surgical and diagnostic applications. The earliest endoscopes relied on the physician to directly view the interior surgical site by looking through the eyepiece of the endoscope. As video camera technology evolved, endoscopes could be coupled to a video camera indirectly through a coupling lens attached to the eyepiece, or directly by coupling the image to the sensor without use of an eyepiece at all. The use of video displays allows the entire operating team to view the surgical site, and the surgeon is not required to keep his eye at the endoscope ocular. The use of video also permits documentation (image storage) without the use of bulky and inconvenient photographic equipment.

Endoscopes currently exist in an array of different forms and are suitable for a wide variety of surgical procedures. Most endoscopes are designed to provide a broad view of the interior surgical site, but do not necessarily provide adequate visualization of the tools used with the endoscope. Even though endoscopes may be highly specialized for a particular procedure, they all contain the same basic component systems. An objective optical system captures a single image or view of the surgical area, a relay optical system carries the image from the distal to proximal end of the device, and an eyepiece or camera system (or both) are used to view the transmitted image. Light to illuminate the surgical scene is delivered via optical fibers or waveguides that are integral to the endoscope. The endoscope may also contain working channels or incorporate treatment options such as laser delivery. All of these parts are contained within an outer sheath that may be made from rigid or flexible materials. The endoscope itself may be rigid, semi-flexible, or flexible, and may have the ability to actively bend in one or more directions at its distal tip.

The objective of an endoscope may consist of glass or plastic lenses, diffractive or hybrid diffractive/refractive lenses, GRIN (graduated refractive index) lenses, prisms or mirrors. The image relay system may consist of a series of glass rods and lenses (a "rod lens" system), a series of lenses only, or fiberoptic image guides. The relay system may be bypassed in a video-only endoscope by placing the image sensor directly in the objective focal plane. The eyepiece typically consists of glass or plastic lenses. A video camera may be coupled to the eyepiece via a coupling lens, or may connect directly to the endoscope and view the image formed by the relay or objective system directly. A light source is coupled to the endoscope by a flexible fiberoptic cable in most cases, and is delivered by optical waveguides or fibers that may be glass or plastic. Some endoscopes provide viewing in stereo by incorporating more than one optical system at the proximal end to view the scene from two slightly offset perspectives. While these stereo endoscopes incorporate multiple image channels, they provide only one view of the surgical scene on an electronic display.

Endoscopes may be reusable or disposable, or may be split into one or more disposable and one or more reusable parts. Advantages of reusable endoscopes are that they are usually of much higher quality and have durability designed in. Disadvantages include degradation of the image quality after sterilization, which is performed using such methods as steam autoclave, ETO (ethylene oxide), glutaraldehyde, Steris (peractic acid), Sterrad (hydrogen peroxide plasma), or other harsh chemicals and temperatures. The sterilization process degrades optical coatings, cements, and surfaces, and can also have deleterious effects on the mechanical parts. Another disadvantage of reusable endoscopes is their comparatively high initial cost. Disposable endoscopes do not suffer from repeated sterilization, and also reduce the possibility of cross-contamination from one surgical procedure to the next. Because they must be purchased in larger quantities and do not need to be as durable, initial costs are less than reusables (though per-use costs are typically higher). Endoscopes that are partly disposable and partly reusable are designed to maximize the advantages of each type of device while minimizing the disadvantages and cost per use.

Notwithstanding the great efforts made in the art to overcome the need for major surgery in the treatment of GERD, none of the abovementioned devices and methods have gained any actual popularity, and they are currently not in use. The reasons for this fact are many, and include the difficulty in controlling the operation of the device, the inherent disadvantages of the types of fundoplications that can be achieved by them, the ongoing need for additional invasive operations, particularly the laparoscopic introduction of devices, etc. It is therefore clear that there is a need in the art for a fundoplication method that can be effectively used for the treatment of GERD, and which is free from the above disadvantages of prior art methods and devices.

It is therefore an object of this invention to provide a device and method using it, for the treatment of GERD, which overcome the aforementioned drawbacks of the prior art.

It is another purpose of this invention to provide fundoplication surgical apparatus that can be operated quickly and effectively, without the need for general anesthesia.

It is yet another object of the invention to provide surgical apparatus for the treatment of GERD that can be operated ambulatorily without the need for expensive operating rooms.

It is a further object of the invention to provide a method and apparatus for the partial fundoplication of the fundus of a patient's stomach.

It is an object of this invention to provide a surgical stapler which overcomes the drawbacks of prior art by providing a totally flexible connection between the staple holder and the anvil parts, at the time of insertion and placement at the surgical site; yet holding the staple dispensing part and the anvil part rigidly together and in precise alignment at the time of the firing of the staples.

It is another purpose of the invention to combine a flexible stapling device with a flexible endoscope to achieve an instrument that can be used to endoscopically perform a variety of surgical procedures.

It is a further purpose of this invention to provide a device for performing endoscopic surgical procedures that improves over the devices of prior art in its ease of operation.

It is yet another purpose of the invention to provide a stapling device that is particularly suitable for use in a flexible endoscope for the treatment of GERD by fundoplication.

It is another purpose of the present invention to provide devices that allow implementation of said methods by using ultrasound techniques to position separate parts of an endoscope with respect to each other.

Other purposes and advantages of this invention will appear as the description proceeds.

SUMMARY OF THE INVENTION

In one aspect, the invention is directed to an endoscopic device, particularly for the partial fundoplication, comprising:
- a distal bending portion and a flexible portion suitable to be positioned in extended shape within the esophagus of a subject;
- a positioning assembly comprising two separate elements, one of which is located on said distal bending portion, and the other on said flexible portion;
- a stapling assembly comprising a staple ejecting device, wherein said staple ejecting device is located on either said bending portion or on said flexible portion, said staple ejecting devices being in working positioned relationship when said two separate elements of said positioning assembly are aligned; and
- circuitry for determining when said two separate elements of said positioning assembly are aligned.

According to a preferred embodiment of the invention, the stapling assembly further comprises an anvil, wherein one of said anvil and of said staple ejecting device is located on said bending portion, and the other is located on said flexible portion, said anvil and said staple ejecting devices being in working positioned relationship when said two separate elements of said positioning assembly are aligned.

Preferably, but non-limitatively, the device of the invention comprises safety means for disabling the operation of the staple-ejecting device when the two separate elements of the positioning assembly are not aligned.

The device of the invention should preferably comprise viewing means, typically a video camera. As will be apparent to the skilled person, it is usually necessary to provide illumination apparatus for viewing purposes. These, however, are conventional, and are therefore not discussed herein in detail, for the sake of brevity. Additionally, conventional endoscopic devices and accessories can be provided, such as water and/or air supply and/or suction.

According to a preferred embodiment of the invention the endoscopic device further comprises a positioning assembly to position a portion of a stapling assembly within the esophagus at a location of about 5–6 cm above the gastroesophageal junction, when the endoscopic device is in working position. In a preferred embodiment of the invention said portion of the stapling assembly comprises an anvil.

The said portion of the stapling assembly can be displaced along the axis of the endoscopic device by various means. According to a preferred embodiment of the invention this is achieved by the action of a flexible threaded cable coupled with a female thread located in said portion of stapling assembly. In one preferred embodiment of the invention the flexible threaded cable is located within the endoscopic device, and is in contact with the female thread through a slit provided in the wall of the body of the endoscopic device. In another alternative preferred embodiment of the invention the flexible threaded cable is embedded in the external wall of the endoscopic device, and is in direct contact with the female thread of the portion of the stapling assembly.

In one preferred form of the invention the flexible threaded cable is rotated using a micrometric assembly, thereby to displace the portion of the stapling assembly positioned within the esophagus by a controlled distance.

The anvil will be often located within the esophagus, and can be of any suitable shape. According to a preferred embodiment of the invention the anvil is essentially ring-like in shape.

The distal portion of the positioning assembly can be located at different positions on the distal end of the endoscopic device. According to a preferred embodiment of the invention said distal portion of the positioning assembly is located on the distal tip. According to another preferred embodiment of the invention the distal portion of the positioning assembly is located on the outer wall of the distal tip.

Similarly, the distal portion of the stapling assembly can be located at different positions on the distal end of the endoscopic device. According to a preferred embodiment of the invention said distal portion of the stapling assembly is located on the distal tip. According to an alternative preferred embodiment of the invention the distal portion of the stapling assembly is located on the outer wall of the distal tip.

In a further aspect, the invention is directed towards providing a stapling device for a surgical endoscopic device provided with at least one flexible portion, comprising a staple-firing portion and an anvil portion, wherein one of said staple firing portions and one of said anvil portions are located longitudinally displaced from one another along the longitudinal axis of said endoscopic device, with at least a part of said flexible portion between them.

According to preferred embodiments of the invention, the staple firing portion is located proximately to the proximal end of the flexible portion and the anvil portion is located on the distal end or tip of the flexible portion.

According to another preferred embodiment of the invention, the flexible portion is an articulation section According to one embodiment of the invention, the stapling assembly comprises one or more alignment/locking pins that can be extended or retracted from one part of the stapling assembly into a locking position in the second part of the stapling assembly. According to a preferred embodiment of the invention, the motion of the alignment/locking pins is accomplished by employing a dual rack and single pinion system.

According to a preferred embodiment of the invention, the parts of the stapling device are in correct working relationship when two alignment/locking pins that are stored in the anvil portion are extended and engage and lock into receptacles on the staple firing portion.

According to a further preferred embodiment of the invention, the endoscope employs a two-way articulation system. In this case, completely bending the articulation section using a fixed radius of curvature brings the two portions of the stapler into alignment.

In another embodiment, a four-way articulation section is used. In this case a positioning assembly comprising two separate elements, one of which is located near the staple ejecting portion, and the other near the anvil portion is provided to assist in bringing the parts of the stapling device into correct working relationship. The positioning assembly can employ ultrasonic, light, radio frequency, piezoelectric, or magnetic sources and detectors.

The staple firing portion contains a staple cartridge containing one or a plurality of arrays of staples. Each array consists of one or a plurality of staples. The arrays of staples are fired by staple pushers actuated by cams actuable by proximal means. The staple cartridge is indexable after the firing of each of the arrays of staples by the action of a proximal actuating device.

In a preferred embodiment of the invention, there are three arrays of staples and there are five staples in each array and three windows are provided on each side of the staple cartridge to assist in locking it in place after indexing.

Preferably, but non-limitatively, the device of the invention comprises safety means for disabling the operation of the staple-ejecting device when the two separate elements of the positioning assembly are not aligned.

In a preferred embodiment of the invention, the alignment/locking pins are manufactured such that the pin tips can be broken by the force exerted by unbending the articulation section, in case of malfunctioning of the unlocking mechanism.

The endoscopic device of the invention should preferably comprise viewing means, typically a video camera. In a preferred embodiment of the invention, two separate optical channels are provided to provide two independent images, one from the area of the anvil at the distal tip and one from the area of the staple cartridge in the shaft of the endoscope. As will be apparent to the skilled person, it is usually necessary to provide illumination apparatus for viewing purposes. Additionally, other conventional endoscopic devices and accessories, such as water and/or air supply and/or suction, and/or ultrasound are provided.

The present invention also relates to an endoscope comprising two or more optical channels that produce two or more distinct views. The endoscope of the invention is suitable for performing various surgical procedures, including fundoplications, stapling of the stomach for obesity management, bladder neck sling procedures for incontinence management, and other procedures that may benefit from having multiple interior views. Such treatments may be performed percutaneously, or by gaining access via natural body canals such as the esophagus or urethra.

Thus, in one aspect, the invention is directed to an endoscope comprising two or more separate optical channels that produce two or more distinct views, each of said optical channels consisting of an objective lens and a means of capturing or viewing the image; each channel optionally also including one or more of the following elements: a) an optical relay system; b) an ocular; and c) a coupling lens suitable to deliver the image acquired by said objective lens to an image sensor and display apparatus; wherein each objective lens is located at a different position along the length of the endoscope.

In another aspect, the invention is directed to a GERD endoscope comprising:
a) a sheath provided with a distal articulated section;
b) stapler components distributed between a first location at the tip of said articulated section, and a second location along the length of said sheath, and which stapler components can be brought into a cooperative working positioned relationship by articulation of said articulating tip;
c) a first objective lens located on said distal tip;
d) a second objective lens located at said second location along the flexible sheath;
e) a first optical channel to deliver the image acquired by said first objective lens to display apparatus coupled to said endoscope; and
f) a second optical channel to deliver the image acquired by said second objective lens to display apparatus coupled to said endoscope.

In another aspect the invention is directed to a method for carrying out an endoscopic partial fundoplication of the fundus of the stomach of a patient, comprising the steps of:
a) providing an endoscopic device comprising a bending portion and a flexible portion, a positioning assembly comprising two separate elements, and a stapling assembly comprising a staple ejecting device;

b) moving the distal tip of said endoscopic device so as to engage the fundus of the patient and to displace it toward the lower part of the esophagus;

c) bringing said stapling assembly into working positioned relationship by aligning said two separate elements of said positioning assembly located one on the bending portion and the other on the flexible portion of said endoscope;

d) determining when said two separate elements of said positioning assembly are aligned by analyzing a signal resulting by bringing them into close positioned relationship and received at a signal receiving and analyzing circuit cooperating with said positioning assembly;

e) ejecting a plurality of staples from said staple-ejecting device, thereby to connect the tissue between them; and f) rotating the endoscopic device relative to the axis of the esophagus and repeating steps (c) through (e) for as many times as needed to achieve the desired partial fundoplication.

According to a preferred embodiment of the invention the stapling assembly further comprises an anvil, wherein one of said anvil and of said staple ejecting device is located on said bending portion, and the other is located on said flexible portion.

In one preferred embodiment of the invention the signal resulting by bringing the two separate elements into close positioned relationship is maximized by measuring a physical parameter which is a function of the distance. In another preferred embodiment of the invention the signal resulting by bringing the two separate elements into close positioned relationship is maximized by correlating it to a measured physical parameter.

The invention also encompasses a method for positioning the endoscopic device of the invention in pre-aligned working position, comprising the steps of:

A) introducing the endoscopic device through the mouth of a patient and locating the position of the gastroesophageal junction;

B) determining the distance from a reference point located on the endoscopic device, and the gastroesophageal junction;

C) introducing the endoscopic device into the stomach by a length below the gastroesophageal junction sufficient to permit the distal tip to be flexed into a position where the fundus is pushed toward the esophagus;

D) locking the endoscopic device such that it cannot move relatively to the axis of the esophagus;

E) determining the position of the portion of the stapling assembly positioned within the esophagus using its original axial location, the distance determined in step B) above, and the radius of curvature of the distal portion of the endoscopic device; and F) displacing said portion of the stapling assembly so as to position it in the range of about 5–6 cm above the gastroesophageal junction.

All the above and other characteristics and advantages of the invention will be further understood through the following illustrative and non-limitative description of preferred embodiments thereof, with reference to the appended drawings.

BRIEF DESCRIPTION OF THE DRAWINGS

FIG. 20A shows the layout of the cartridge holder body of FIGS. 19A and 19B;

FIGS. 23A and 23B are respectively side and top schematic views of the housing of the stapler cartridge;

FIG. 29A through FIG. 29C show different options for displaying the multiple views;

DETAILED DESCRIPTION OF PREFERRED EMBODIMENTS

Figure 1:
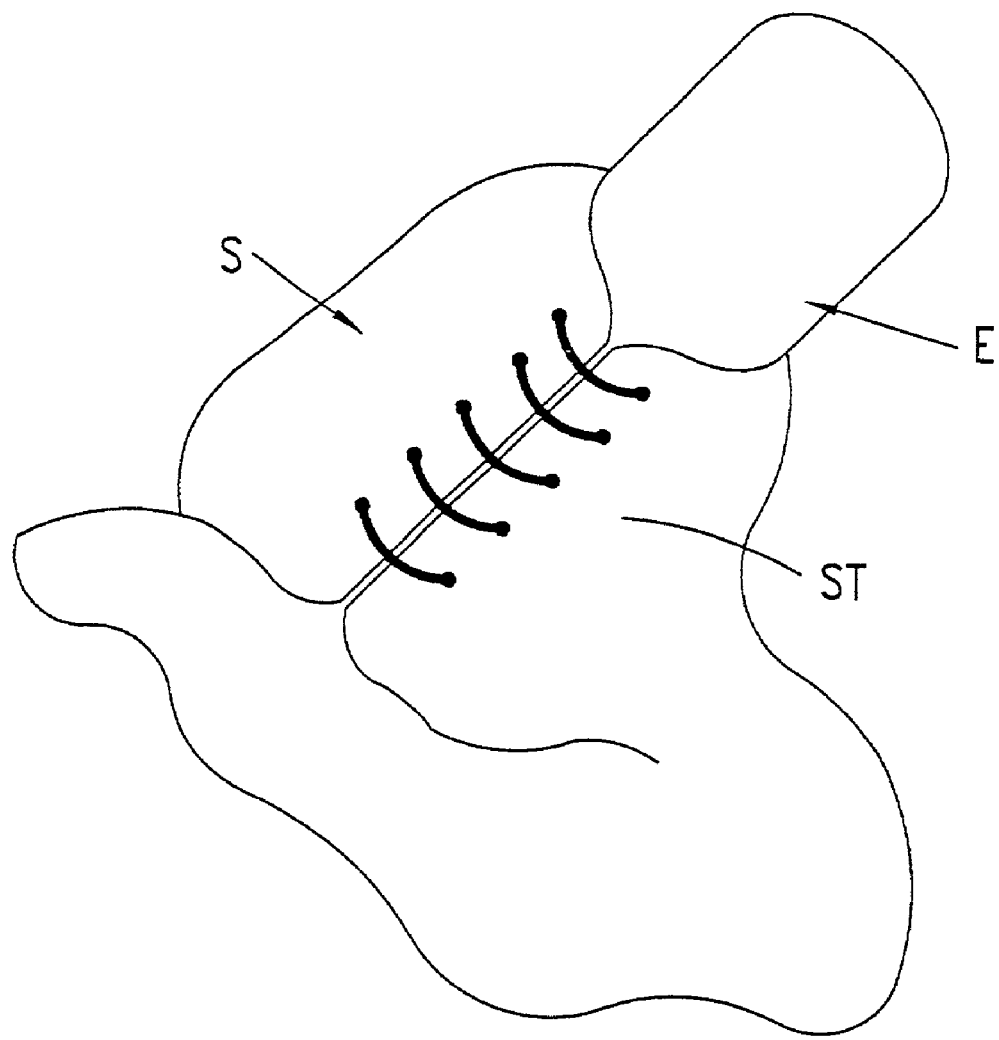
FIG. 1 illustrates the prior art wrapping of the stomach 360 degrees around the esophagus.
Figure 2:
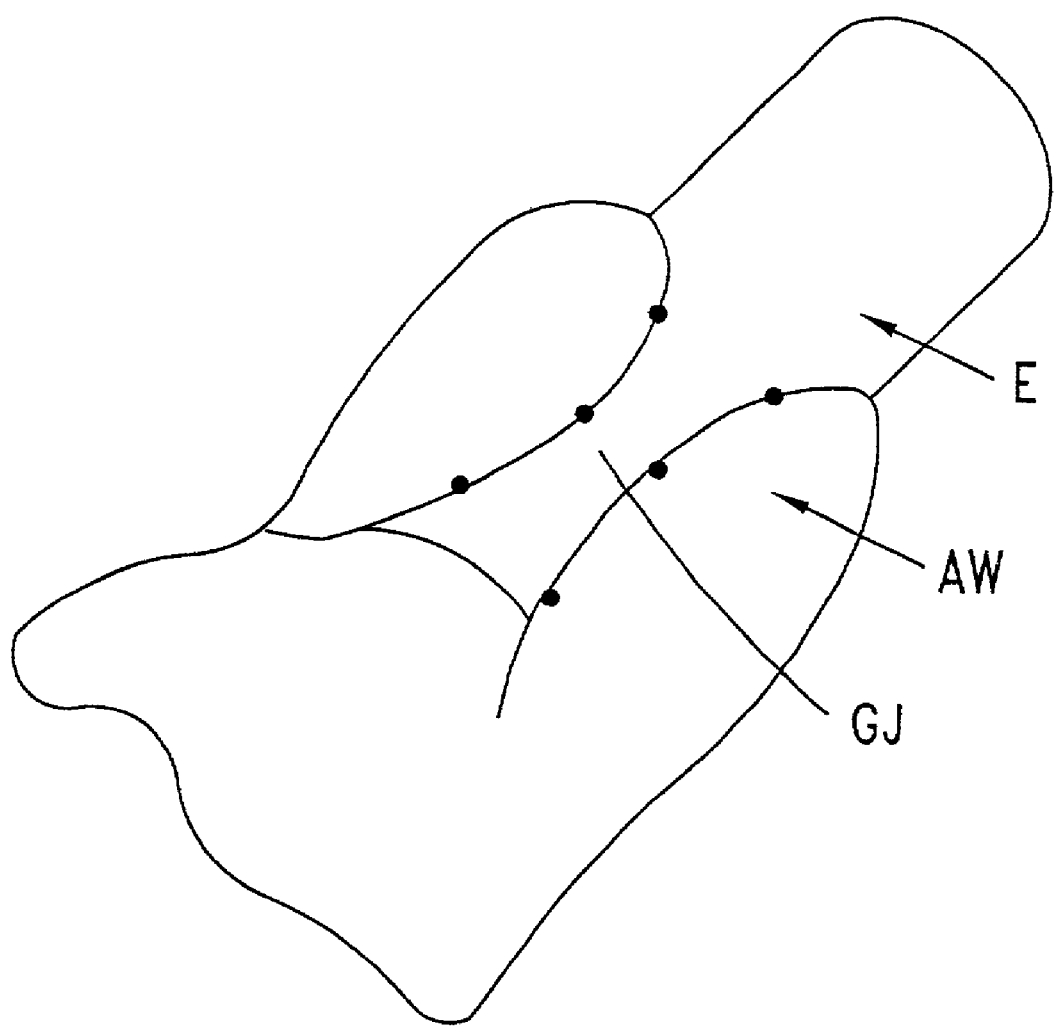
FIG. 2 illustrates the prior art Toupet posterior partial fundoplication (270 degrees)
Figure 3:
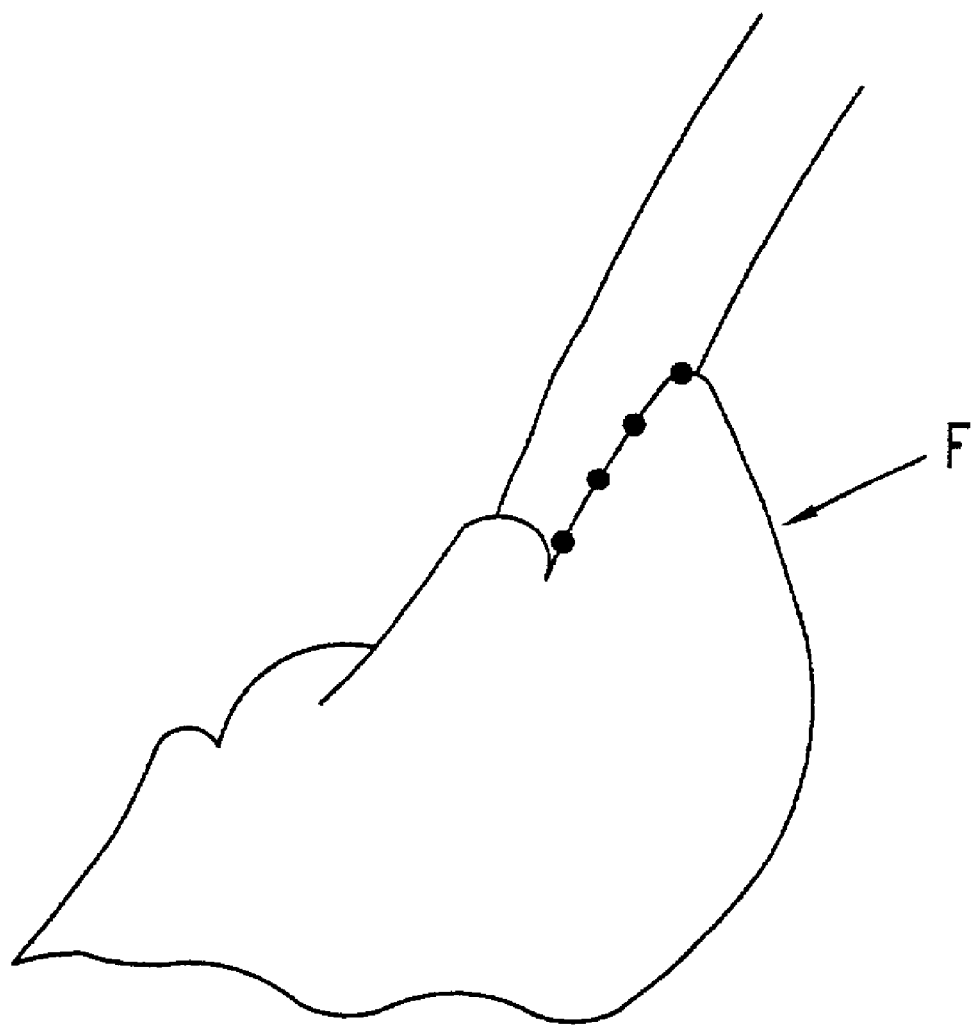
FIG. 3 illustrates the prior art Thal anterior fundoplication (180 degrees)
Figure 4A:
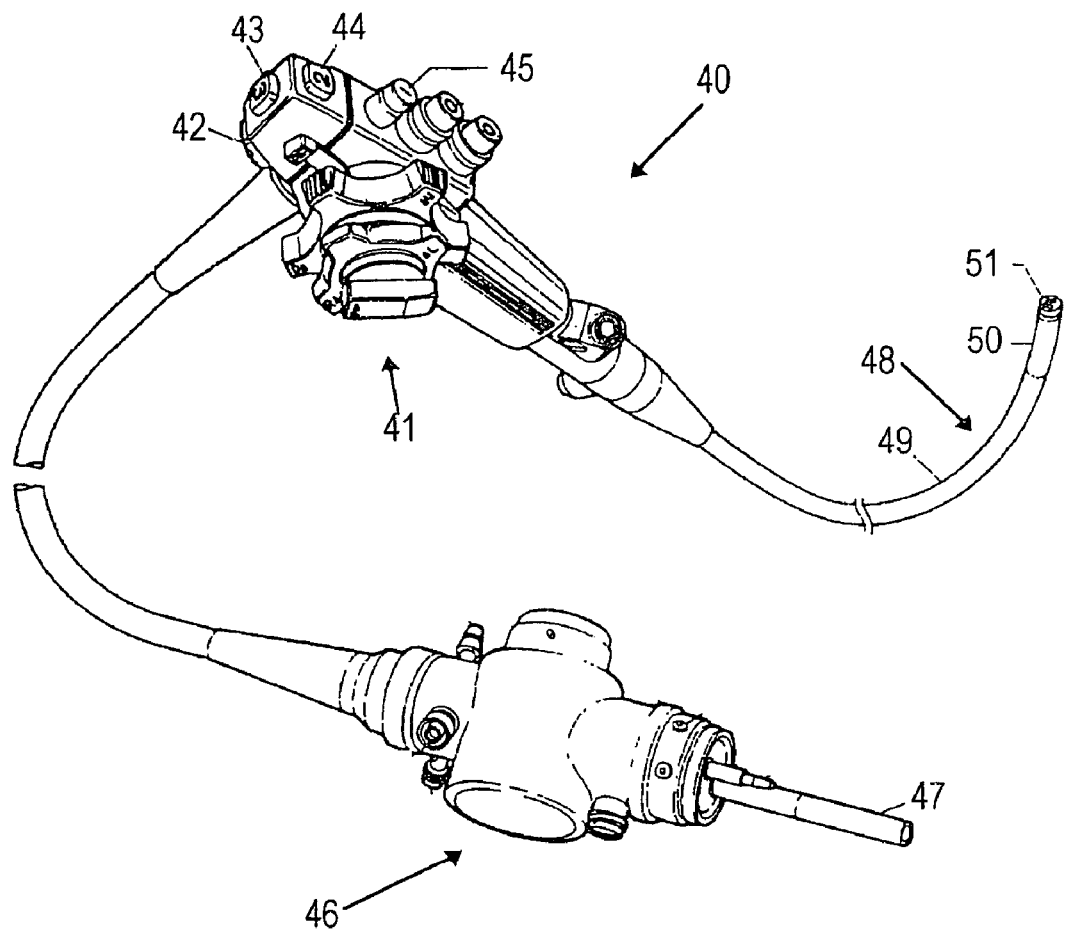
FIGS. 4A and 4B schematically illustrate a conventional endoscope.
Figure 4B:
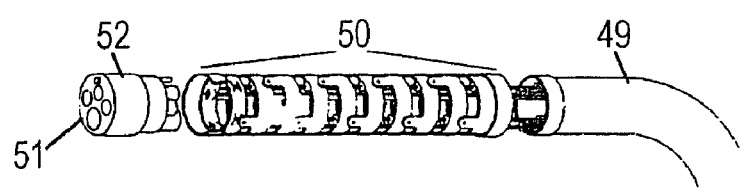

The invention will now be further explained through the illustrative and non-limitative description of preferred embodiments. The invention employs many elements, such as the endoscopic base elements and the surgical stapler, which are well known in the art, and which are therefore not described here in detail, for the sake of brevity. A conventional endoscope is illustrated in FIG. 4. This endoscope comprises several features, such as the operating switches, the angulation lock, etc., that may be present in the device of the invention, but that will not be described in detail in the description to follow, because they are conventional and well known to the skilled person. Thus in the following description only elements needed to illustrate the invention will be described. Briefly, however, the endoscope illustrated in FIG. 4A and generally indicated at 40, is provided with a control section 41 provided with suction valves, locks, switches, etc., switches 42–45 being marked for illustration purposes. It also comprises a connector section 46, used to connect air and water inlets, light guides, etc., the light guide being indicated at 47, for illustration purposes. The insertion tube 48 consists of three separate sections: a flexible portion 49, a bending section 50 and a distal end 51. These latter three sections are shown in greater detail in FIG. 4B, which also indicates the distal tip 52 in which the distal end 51 resides.

Figure 5:
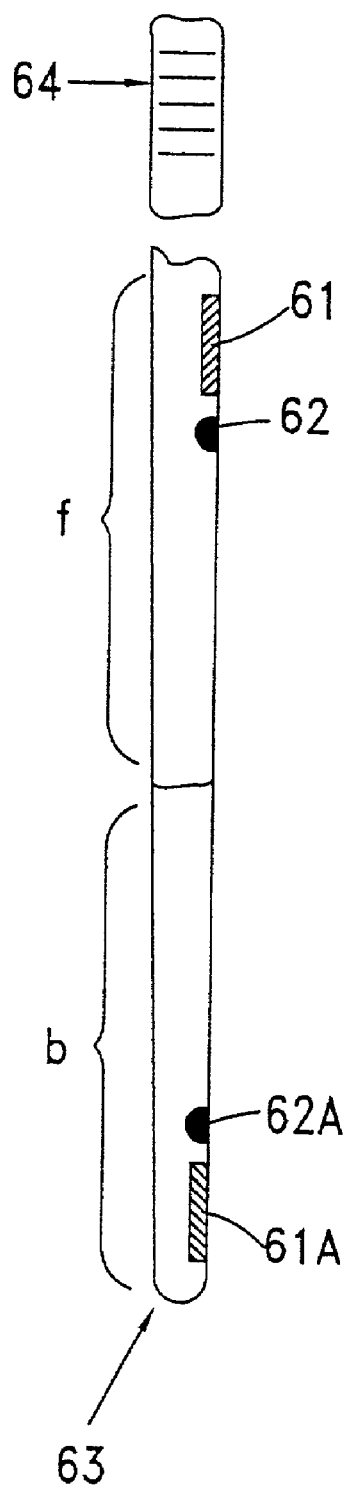
FIG. 5 schematically illustrates the fixed portion and the bending distal portion of the device of the invention.

Looking now at FIG. 5, the distal portion of the device of the invention is schematically shown. This portion comprises a bending section, indicated at "b", and a fixed, non-bending section, indicated at "f". The bending portion can be of any suitable type, e.g., as that shown in FIG. 4A, or as described in the aforementioned U.S. Pat. No. 5,787, 897. The fixed section, f, contains a first element of a stapling assembly, 61, the counterpart of which, 61A, is located near the distal tip 63 of the bending section, b. Stapling elements 61 and 61A, together, form the entire stapling assembly, to be discussed in greater detail below. Similarly, the fixed section f contains a first positioning element 62, which together with its counterpart 62A, located in this particular embodiment near the distal tip 63 form the entire positioning assembly, to be discussed in greater detail below. Positioning elements 62 and 62A can be located at any suitable location along the respective sections b and f of the device (e.g., either below or above elements 61 and 61A), provided that when the two elements 61 and 61A of the stapling assembly are in working positioned relationship, said two elements 62 and 62A are also in working positioned relationship.

Positioning markings 64 may be located on the device, at the extremity outside the patient, to provide information on the length of device that has been introduced into the patient. Endoscopic vision means (not shown) can also be provided, to image the fundus of the stomach and to determine the distance from introduction to the GE junction for each specific patient. These means are conventional of endoscopic apparatus, and are therefore not described herein in detail.

The device of the invention has three particularly important areas of operation: 1) the mechanical operation of the device, to bring it into the generally desired position; 2) the positioning operation, to position it in the exact desired location prior to surgical operation; and 3) the surgical operation which typically—but non-limitatively—involves the stapling of living tissue. These operations will now be described in detail.

Mechanical Operation of the Device

Figure 6A:
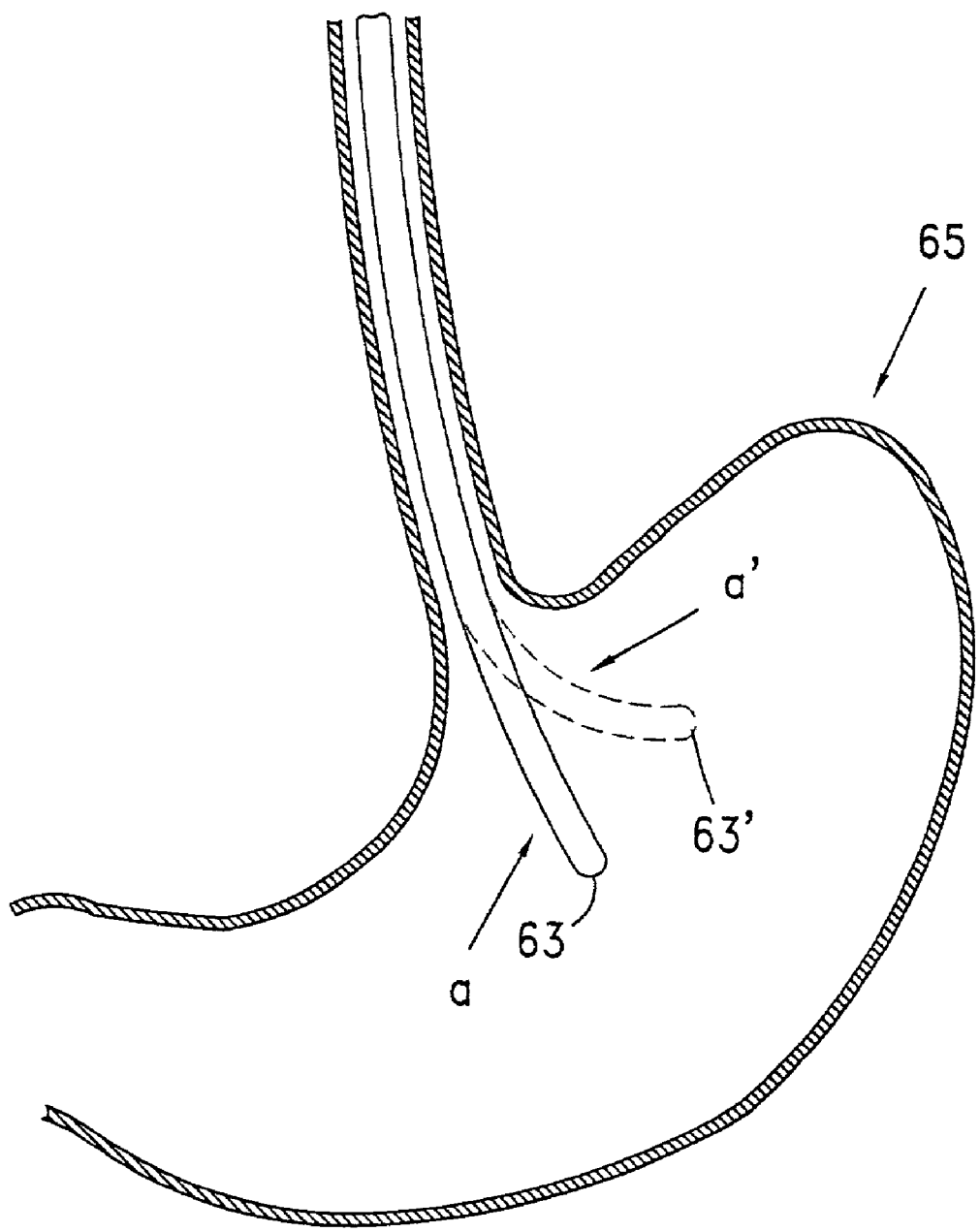
FIGS. 6A and 6B schematically illustrate the mechanical procedure involved in the fundoplication using a device according to the invention.

The mechanical operation of the device involves the bending of the bendable section of the device so as to engage the fundus of the stomach with the distal tip 63, and to move it toward the lower esophagus. This is schematically illustrated in FIGS. 6(A and B). In FIG. 6A two positions of the device are shown, a and a'. Position a is the initial position after the device has been inserted the whole of its desired length of insertion. Position a' illustrate the beginning of bending section b of the device, towards the fundus 65, the tip being indicated as 63'.

Figure 6B:
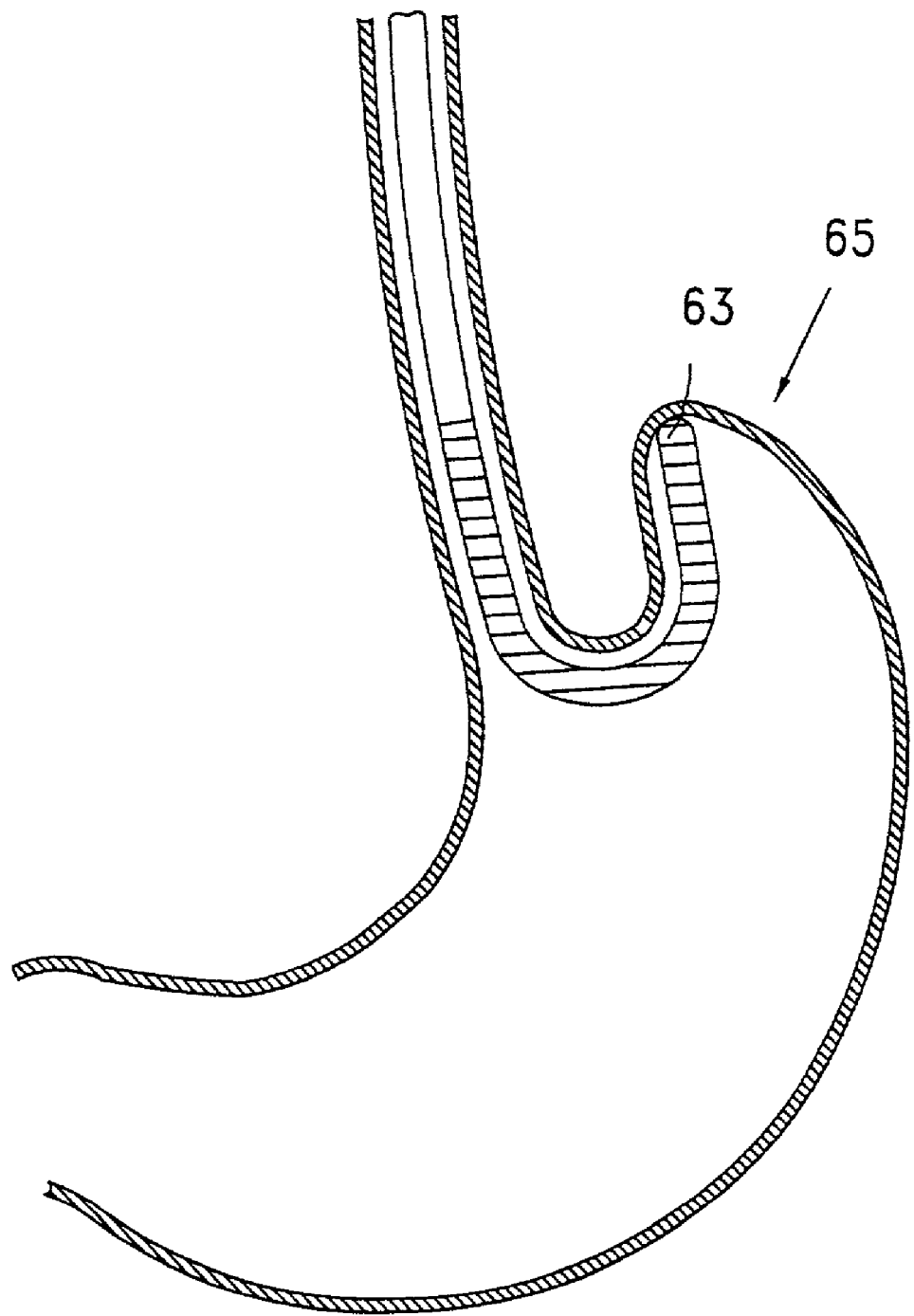

In FIG. 6B the situation shown is that in which bending of the device has been taken further, and the distal tip 63 has caused the fundus 65 to move from its original position to a position nearer the lower esophagus. In this position, or in a closer position, if the fundus is correctly positioned by tip 63, it is possible to carry out the stapling together of the fundus and esophagus. This procedure may have to be repeated once or more than once to achieve about 180° of fundoplication.

The Positioning Operation

The positioning operation is the most critical step in the procedure. This can be explained by looking at FIG. 7. In the figure, a device according to a preferred embodiment of the invention is schematically shown, in which a stapling assembly 61, 61A is shown, as well as a positioning assembly 62, 62A, located on the endoscopic device generally indicated at numeral 66. It should be noted that the order of these two assemblies is inverted, as compared to that of FIG. 5, to illustrate that the order is not critical.

In order to fasten the lower part of the fundus 65 to the lower part of the esophagus 67, by means of stapling assembly 61, 61A (the operation of which will be described below) it is imperative that element 61 and element 61A be brought into the correct working positioned relationship, so that the staples, when ejected, perform their required task. Failure to bring the parts of the stapling assembly into the correct positioned relationship may be fatal, as it will result in the staple not being correctly positioned or folded, and in a high risk of damaging the tissue where the stapling has been performed.

Figure 7:
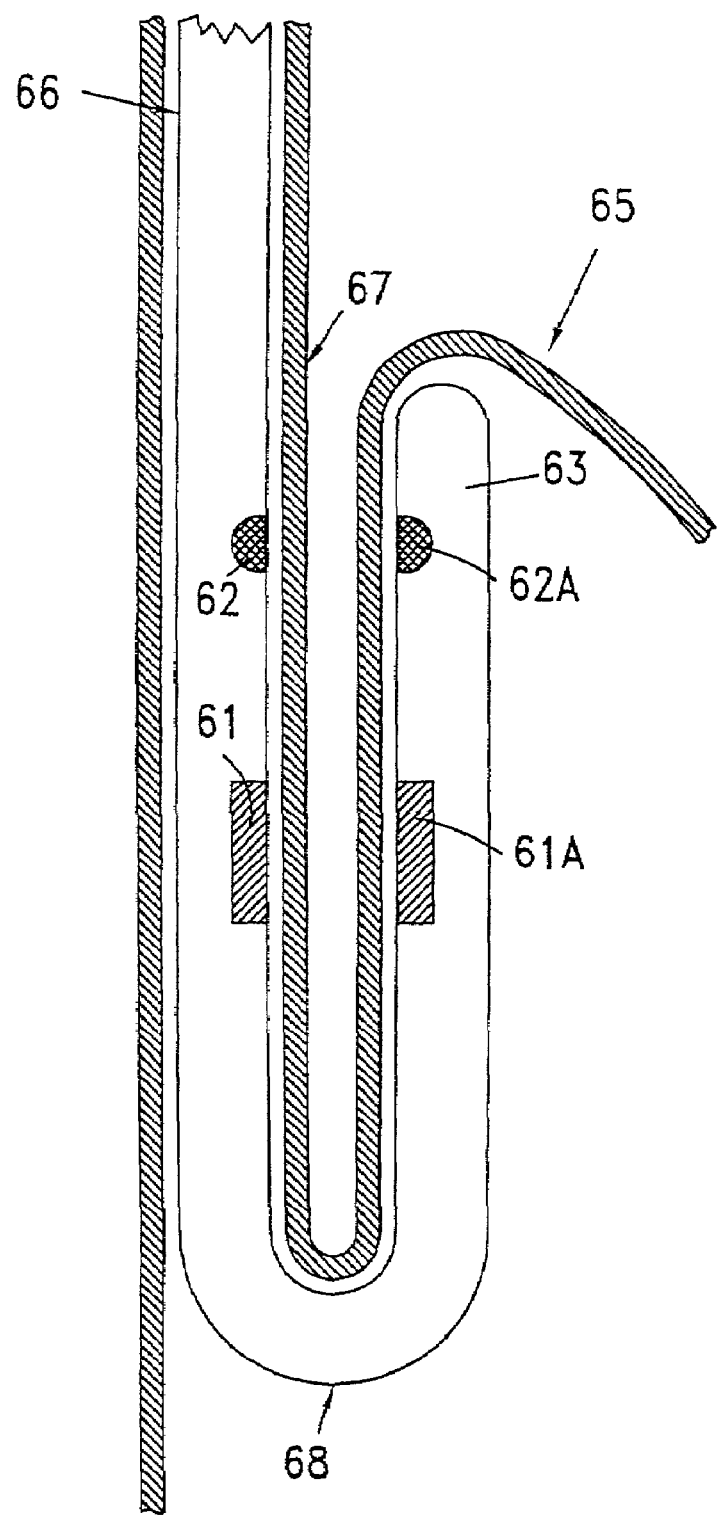
FIG. 7 schematically illustrates the positioning of the device prior to stapling.
Figure 8A:
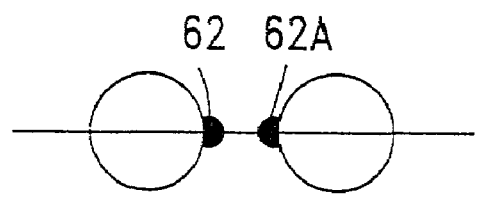
FIGS. 8A–8D illustrate the various possible mismatchings in the positioning of the device.

The possible mismatching of the sections of the device is illustrated in FIGS. 8A–8D. FIG. 8A shows the desired situation, in which the two elements, 62 and 62A, that form the positioning assembly, are aligned one with the other, thus bringing the device into working conditions. As schematically seen in FIG. 7, aligning of the positioning assembly results in a corresponding aligning of the stapling assembly.

Figure 8B:
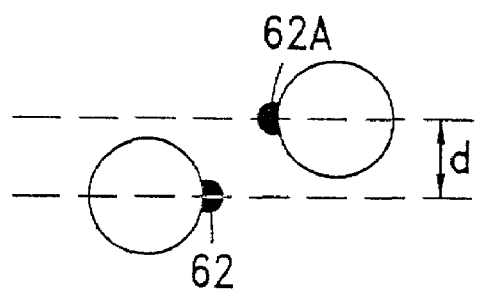
Figure 8C:
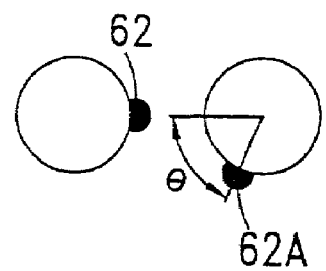
Figure 8D:
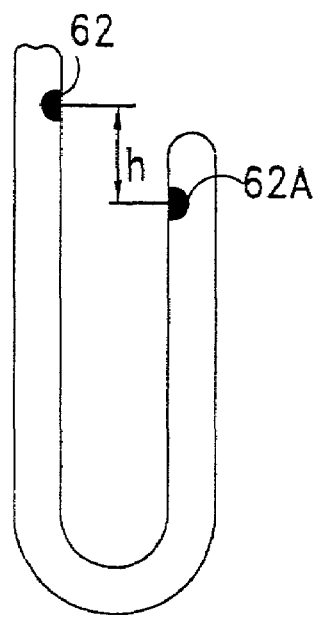

FIG. 8B shows a situation in which an angular movement has occurred at the elbow 68 of the device of FIG. 7, resulting in a misalignment of magnitude "d" between the positioning elements. In FIG. 8C a rotational mismatching is shown, in which the bending section of the device has also rotated along its axis by an angle θ, again resulting in a comparable misalignment of the stapling assembly. Finally, FIG. 8D shows the situation in which the distal tip 63 of the device has not been pushed up sufficiently, and a misalignment of height "h" has occurred. All these occurrences must be avoided, since any of them is hazardous and will not obtain the desired result.

According to the invention, therefore, the aligning assembly consists of two elements that, when brought into an alignment such that the elements of the stapler assembly are aligned, permits to actuate the stapler. According to a preferred embodiment of the invention the elements of the positioning assembly are ultrasonic elements, i.e., an ultrasound transducer and a receiver. A simple analysis of the ultrasound signal received at the receiver makes it possible to determine the maximal signal, which corresponds to the exact alignment. According to another preferred embodiment of the invention, one of elements of the positioning assembly emits light and the other is a photosensitive element that translates the received light into a signal. Again, the maximal intensity of the signal indicates the maximal alignment.

According to still another preferred embodiment of the invention, one of the elements of the positioning assembly is a piezoelectric transducer, and the other is a simple protrusion. Application of a pressure by the protrusion on the piezoelectric transducer, via the thin tissue, generates an electric signal which, again, can be analyzed to determine its maximal value.

It should be mentioned that, in certain types of positioning assemblies, e.g., if it were desired to employ an RF assembly, it is not at all necessary that the two elements, 62 and 62A, be physically aligned as shown in FIG. 8A, viz., such that their physical centers are essentially aligned. When the alignment procedure does not rely on a physical, center-to-center matching, elements 62 and 62A could be positioned differently on the two sections of the device, provided that when they generate an output signal representative of maximal alignment, elements 61 and 61A of the stapling assembly are indeed physically aligned.

As will be appreciated by the skilled person, many different alignment schemes can be devised, for instance, using RF signals to determine the alignment position, or using a magnetic field generator on the one side, and a magnetic field positioning sensor on the other.

Surgical Operation

The surgical operation will be illustrated herein with reference to the stapling of tissue, for the sake of simplicity. It should be understood, however, that the invention is by no means limited to stapling, and that any other operation capable of connecting tissue, so as to bring the fundus into juxtaposition with the lower part of the esophagus—e.g., suturing with a needle, can also be employed. However, stapling is the most convenient procedure in common use for this type of surgery, and therefore will be used herein to illustrate the invention.

Figure 9A:
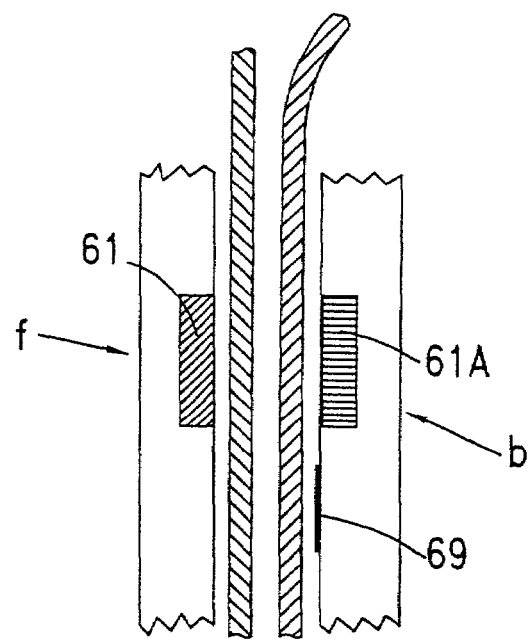
FIGS. 9A and 9B schematically illustrate the stapling procedure.
Figure 9B:
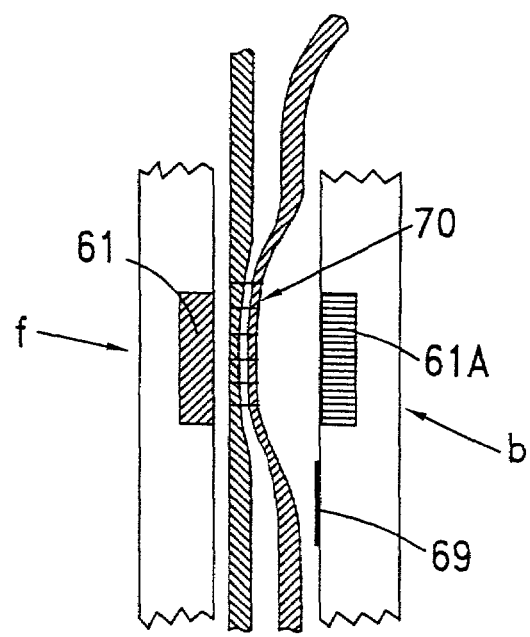

FIG. 9 shows the relevant part of the device and tissue. In FIG. 9A element 61, which in this case is the anvil, is aligned with element 61A, which in this case is the staple ejecting device. Of course, the two elements could be inverted since the operation of the stapler would be exactly the same in both cases. Stapler 61A may have been kept covered by a retractable cover 69, to avoid infiltration of foreign material, until the two elements are aligned and ready to use. Actuation of elements in an endoscope, such as that of cover 69, is well understood by the skilled engineer, and is therefore not discussed herein, for the sake of brevity FIG. 9B shows the situation after the stapling has been effected. Staples, collectively indicated at 70, have engaged between the fundus and the esophagus, at the specific location on which it was operated. It is now possible to move the device by rotating it to its next location (i.e., by moving it in a direction perpendicular to the plane of the cross-section of FIG. 6. When the next location is reached, the aligning procedure is repeated, and the stapling is effected again.

Surgical staplers are well known in the art. Examples of suitable surgical staplers can be found in the aforementioned U.S. patents, and a preferred stapler according to the invention will be described in detail hereinafter.

It should further be noted that anvil-less staplers can also be provided. This type of stapler is well known in the art and is manufactured, for instance, by Design Standards Corporation, USA. In such a case, of course, there is no need to align the stapler and the anvil, since no anvil is needed. However, it is still needed to position the two elements of the positioning assembly in the correct positioned relationship, since otherwise the wrong tissue portion may be stapled. Accordingly, all positioning operations described herein are relevant for both staplers with and without an anvil. Whenever reference is made in this description to either type of stapler it should be understood that the same applies, mutatis mutandis, to the other type, and the relevant part of the description will be not repeated, for the sake of brevity.

Figure 10:
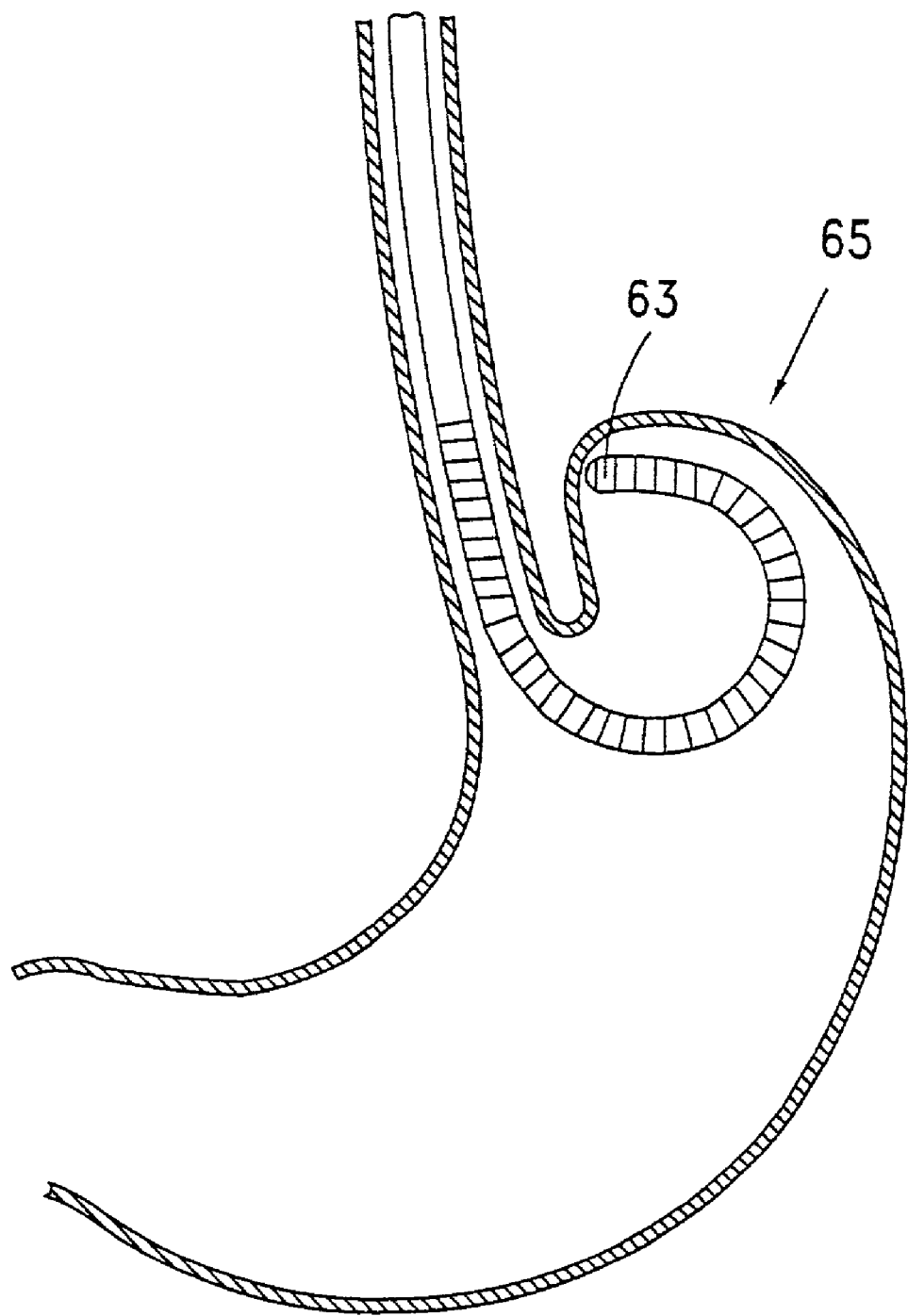
FIG. 10 schematically illustrates the operation of an endoscopic device according to another preferred embodiment of the invention.
Figure 11:
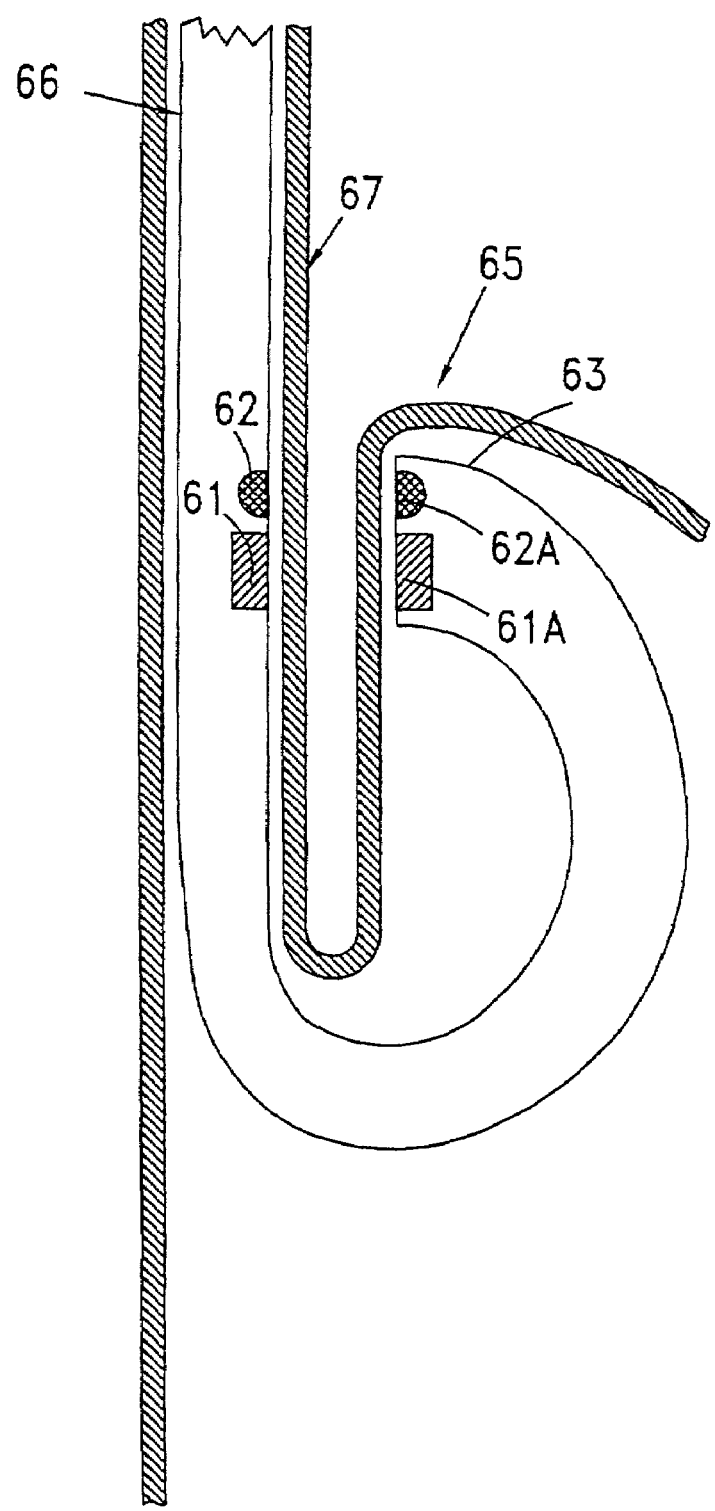
FIG. 11 illustrates the positioning of the device of FIG. 10.

Another preferred embodiment of the invention is described in FIG. 10, which represents the same situation as described above with reference with FIG. 6B, but when using a bending end made of joints which have a radius of curvature such that, when brought into the position shown in FIG. 11, the tip 63 of the end part of the bending portion of the device portion "b" of FIG. 5) is not parallel to the fixed portion (portion "f" of FIG. 5), as shown in FIG. 6B, but rather its tip 63 is positioned in front of elements 61 and 62 (FIG. 5). Such bending end and tip can be, e.g., similar to those shown in FIG. 4B.

FIG. 11 schematically illustrates the positioning of the device, according to this preferred embodiment of the invention. Positioning element 62A, located on tip 63, is brought into position in front of positioning element 62, located in the fixed portion of the device.

Figure 12:
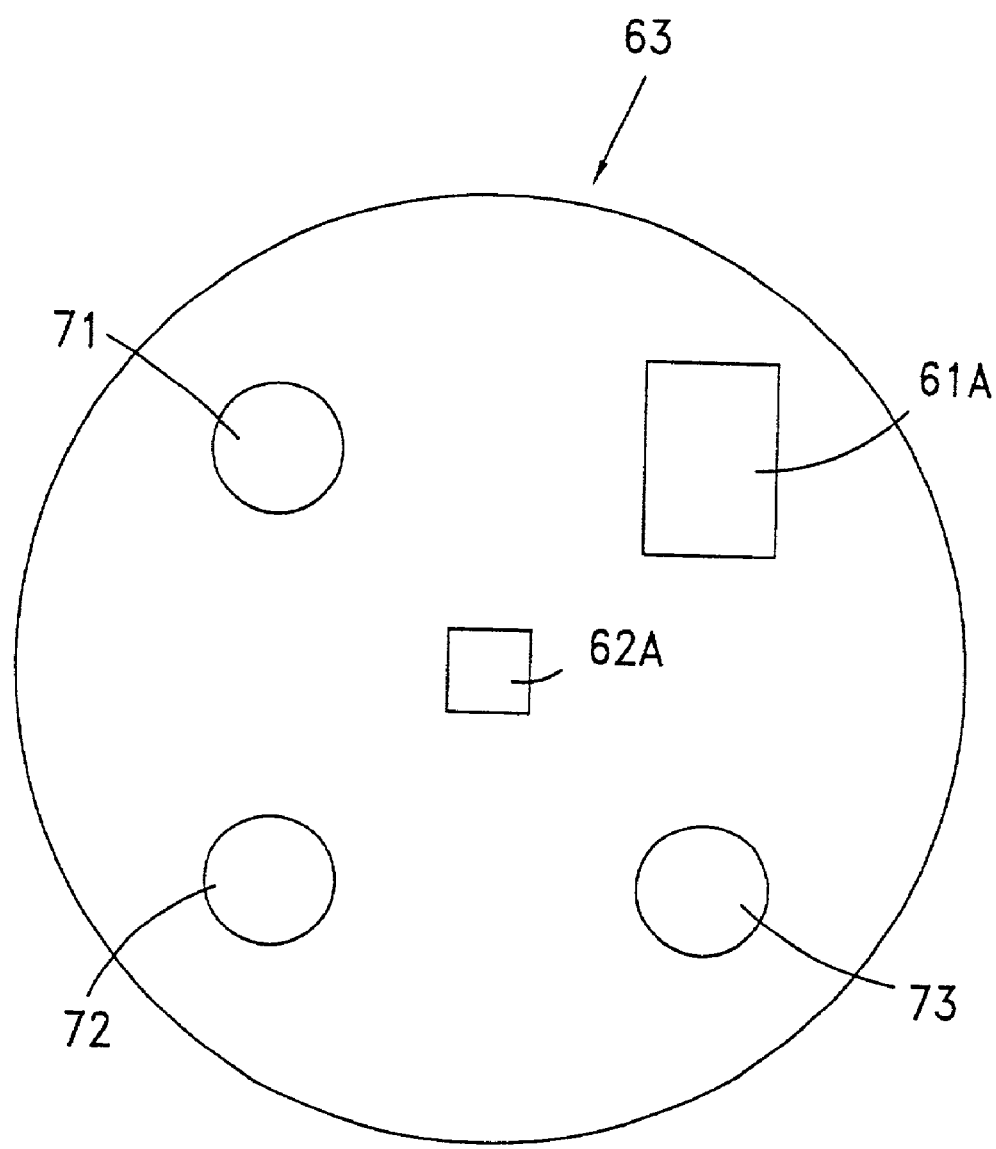
FIG. 12 shows the arrangement of the tip of the device of FIG. 11.

FIG. 12 schematically illustrates a tip 63, according to a preferred embodiment of the device of FIG. 11. The tip comprises positioning element 62A (positioned at the center in the figure, but which can be positioned elsewhere), element 61A of the stapling assembly, a lighting element 71, which may be, e.g., an optical fiber, air suction and/or water dispensing opening 72, and a video camera 73.

Introduction Procedure

Figure 13:
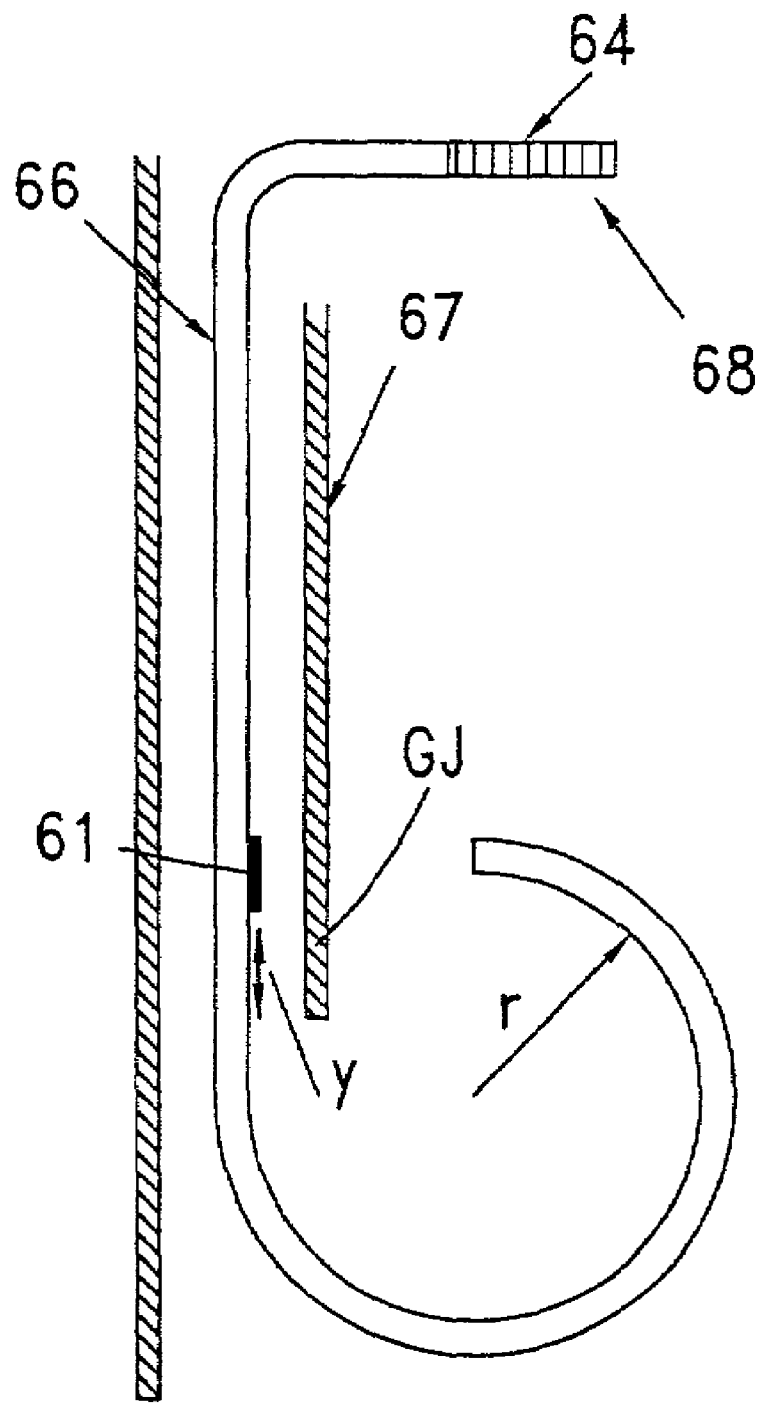
FIG. 13 illustrates the positioning procedure of the anvil in the esophagus, according to a preferred embodiment of the invention.

The procedure through which the endoscopic device is introduced and brought into a generally aligned position (prior to using the positioning assembly 62–62A of FIG. 7), will be briefly explained, using a simplified example, with reference to FIG. 13.

When in working position, stapling element 61 (referred to as the anvil in this example), must be located at a distance "y" from the gastroesophageal junction GJ which typically varies between about 5–6 cm, while the total length of the esophagus typically varies between about 35–50 cm, depending on the subject. In order to determine the exact length "y", the GJ is identified, when first introducing the device, by visual inspection, e.g., via video camera 73 of FIG. 12. The total length of the device introduced at this stage is determined by reading the value indicated on the positioning markings 64, as also explained with reference to FIG. 5. Knowing the total length of the endoscopic device, its radius of curvature, "r", and the exact position of the GJ, makes it possible to determine the exact position of the anvil 61 relative to the length of the endoscopic device.

Figure 14:
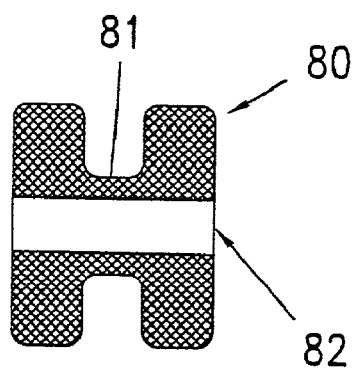
FIG. 14 is a biter, used in a procedure according to a preferred embodiment of the invention.

The endoscopic device 66 is then advanced to the desired position, and is then fixed using a constraining device, such as a biter illustrated in FIG. 14. The biter, shown in cross-section and generally indicated at 80, has a biting portion 81 which is held between the teeth of the patient. The endoscopic device (not shown) is introduced through the biter via an appropriate opening 82. When the device has reached the desired position the endoscopic device is caused to remain in its position by fixing it to the biter using conventional clamping means (not shown).

Figures 15A, 15B:
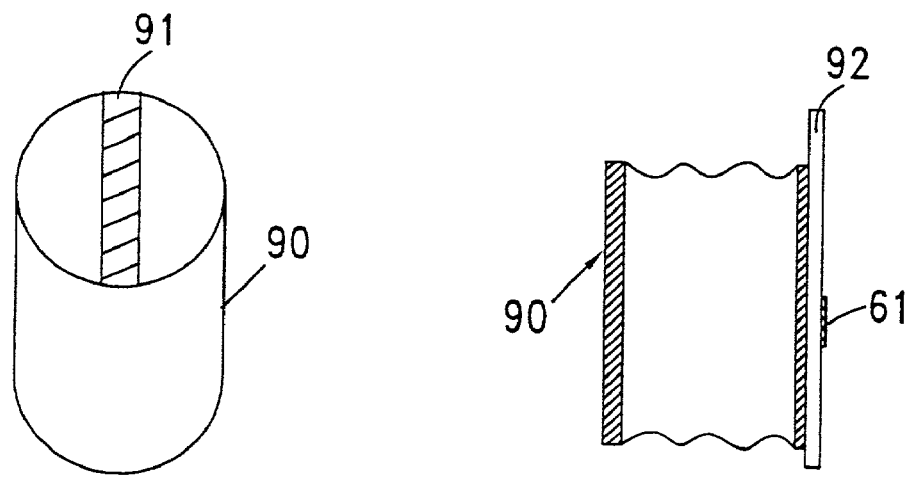
FIGS. 15A–15C illustrate the fine positioning of the anvil within the esophagus.
Figure 15C:
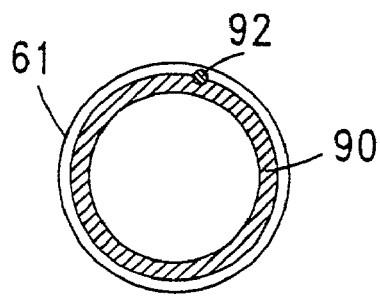

It is now necessary to move the anvil 61 so as to bring it into the desired position, i.e., 5–6 cm above the GJ. This is done, according to a preferred embodiment of the invention, using an arrangement such as that shown in FIGS. 15A to 15C. FIG. 15A shows a section 90 of the endoscopic device, which is provided with a slit 91 through which a threaded cable can be introduced. This is schematically shown in FIG. 15B, where the anvil 61 is mounted on threaded cable 92, coupled with a female thread located in anvil 61. Threaded cable 92, which is flexible, reaches a micrometric displacement assembly (not shown), positioned before the biter, at end 68 of the device. By actuating the micrometric displacement assembly, knowing the patient's esophageal length and the position of the GJ, anvil 61 can be exactly positioned 5–6 cm above the GJ, in general pre-aligned position with the other half of the stapling assembly, 61A. FIG. 15C is a top cross-sectional view, showing the body 90 of the assembly device, the threaded cable 92, and a circular anvil 61.

Figure 16A:
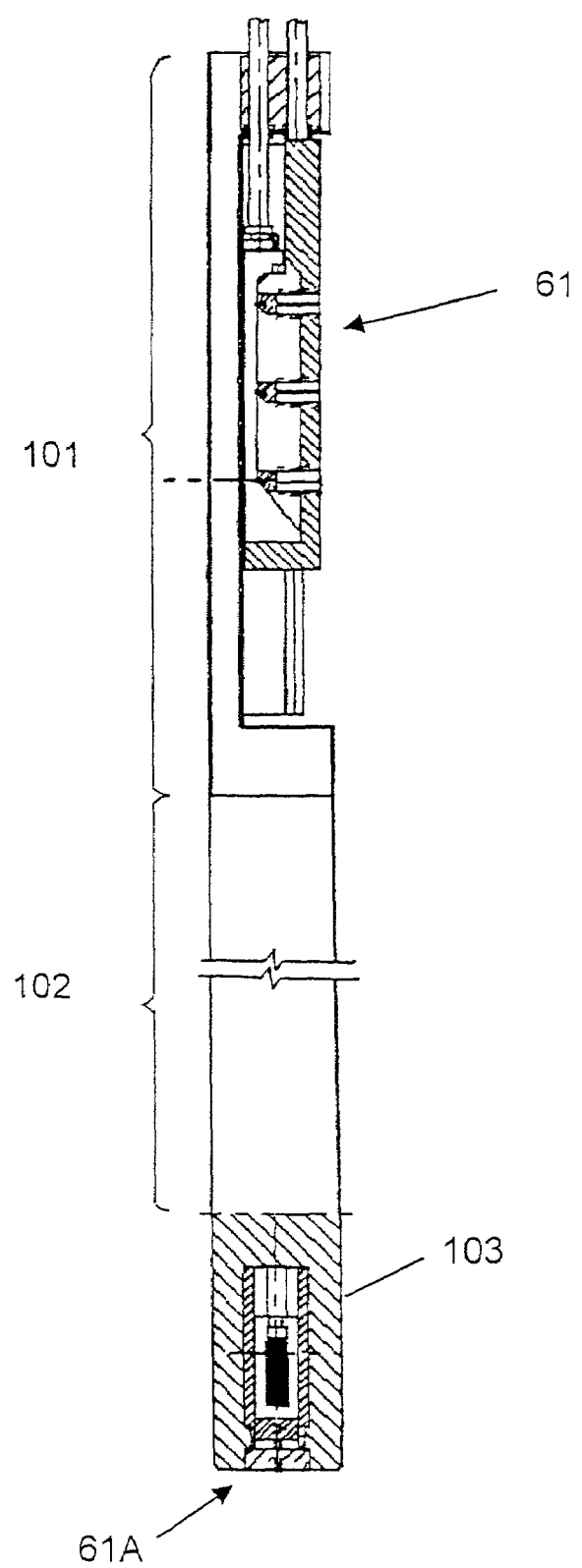
FIG. 16A schematically illustrates the fixed portion and the articulation distal portion of an endoscope, comprising a stapler according to a preferred embodiment of the invention.

Looking now at FIG. 16A, the distal portion of an endoscope, according to the preferred embodiment of the invention is schematically shown. This portion comprises a staple firing mechanism indicated at 101 and an articulating section 102, and the distal tip 103. The section 50 of FIG. 4A is composed of the sections 102 and 103.

Articulating section 102 is similar in design to that of conventional endoscopes, but possesses several unique features. In order to simplify the alignment procedure and at the same time achieve maximum accuracy, a two-way articulation design has been chosen for the preferred embodiment of the invention. This means that the articulating section is constrained to bend in one direction only (i.e. the tip of the endoscope can only bend from straight ahead to one side and back to a relatively fixed plane). Secondly, the device is able to bend up to 270° in order to carry out the required medical procedure, which is further than in conventional endoscopes. Finally, the articulating section is strong enough to provide a significant force against the tissues during fundus distension (described below with reference to the illustrative surgical procedure), clamping, and stapling.

According to a preferred embodiment of the invention, the stapler cartridge is positioned at the proximal end of the articulation section, 102. The stapler deployment system has a side firing design and requires an anvil which is located on the end of the distal tip. Both the stapler cartridge and the anvil module are preferably replaceable and fit into receptacles on the shaft and distal tip. These receptacles are labeled 61 and 61A respectively in FIG. 16A. The stapling elements at 61 and 61A, together, form the entire stapling assembly, to be discussed in greater detail below.

Figure 16B:
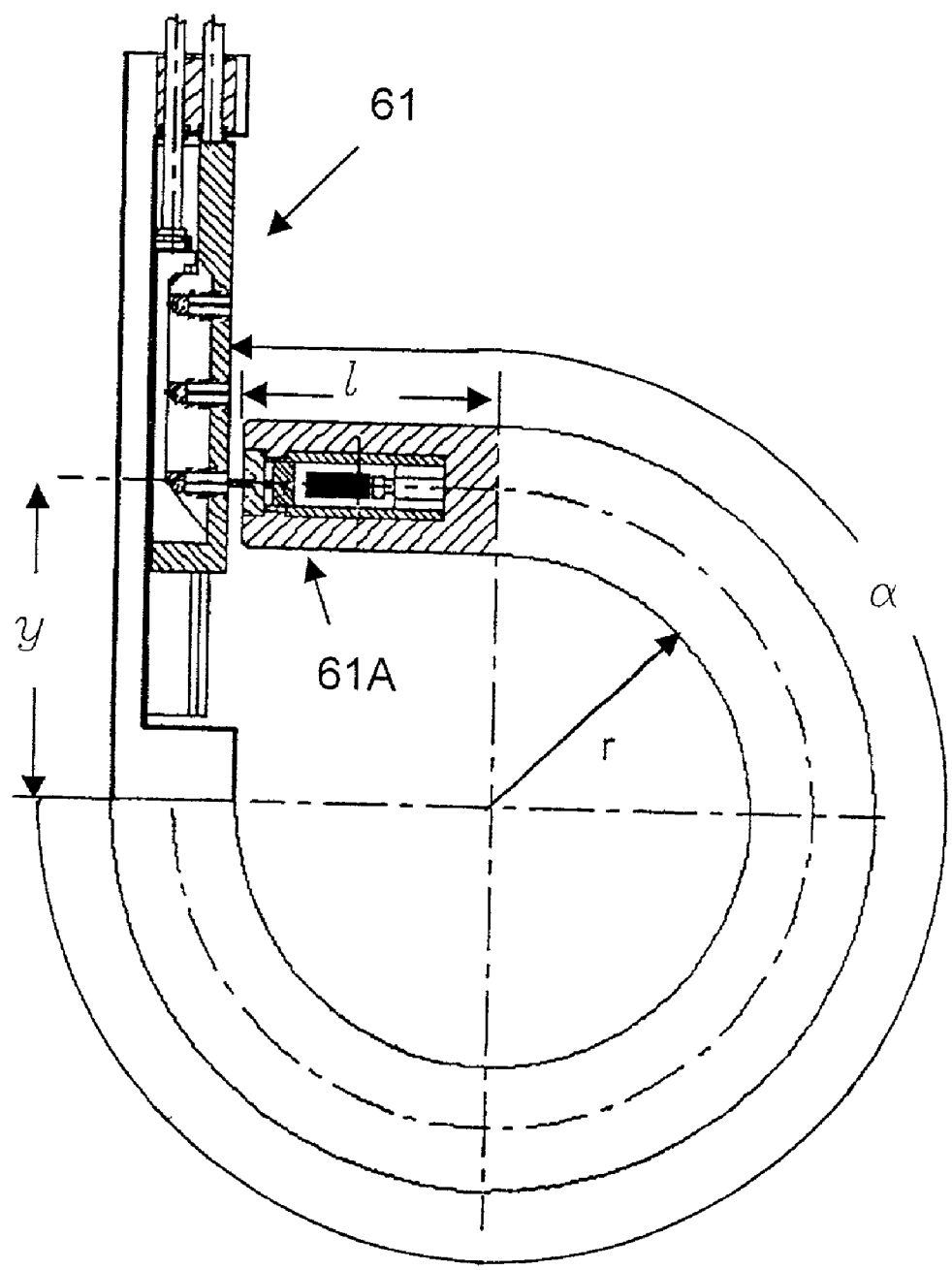
FIG. 16B schematically illustrates the articulation of the endoscope of FIG. 16A through its maximum bending angle.

FIG. 16B schematically shows the device of FIG. 16A in a fully articulated position. The articulation section 102 has been bent through bending angle α using fixed radius of curvature "r". The values of radius "r" and the length of the articulation section are determined by the fixed values "l" (length of the rigid distal tip) and "y" (the distance from the position at which the stapling is to be carried out to the proximal end of the articulation portion of the endoscope) in such a way that articulation of the device completely brings the two parts of the stapler assembly exactly into alignment.

Figure 17A:
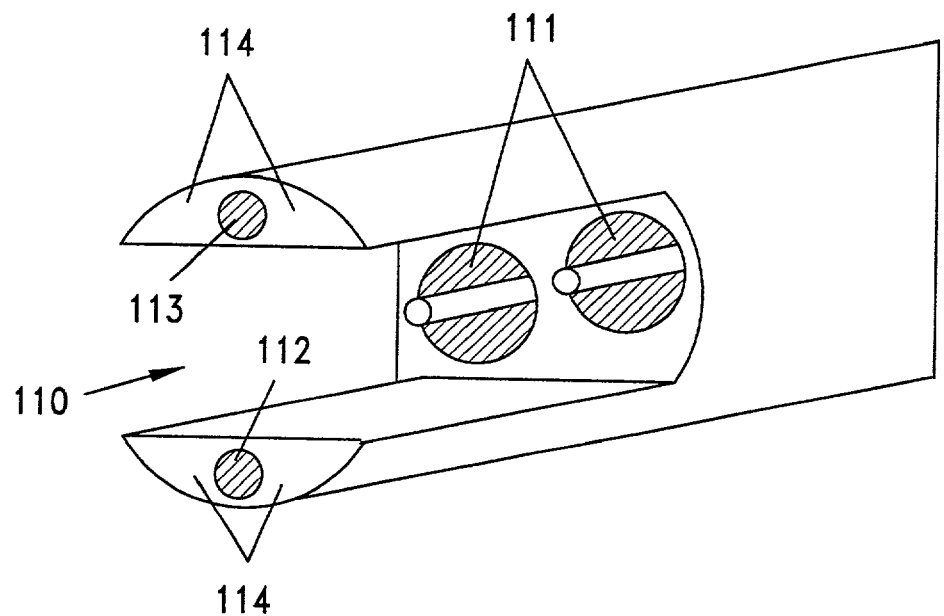
FIG. 17A schematically illustrates the distal tip of an endoscope, provided with a receptacle for the anvil section of a stapler, according to a preferred embodiment of the invention.

FIG. 17A schematically shows the distal tip of the endoscope (section 103 in FIG. 16A). The disposable anvil module of the stapler assembly goes into a receptacle indicated at 110. Two round reusable plungers and seals are part of the anvil holder and are shown at 111. A channel for suction, irrigation, or any other purpose is shown at 112. The imaging channel is 113 and 114 represents illumination fibers.

The skilled person will understand that other options can be provided and other configurations are allowed depending on the requirements of the endoscopic procedure to be performed. As one example, a transducer, receiver, or reflector can be placed at one of positions 114 for use in ultrasound positioning as described below.

Figure 17B:
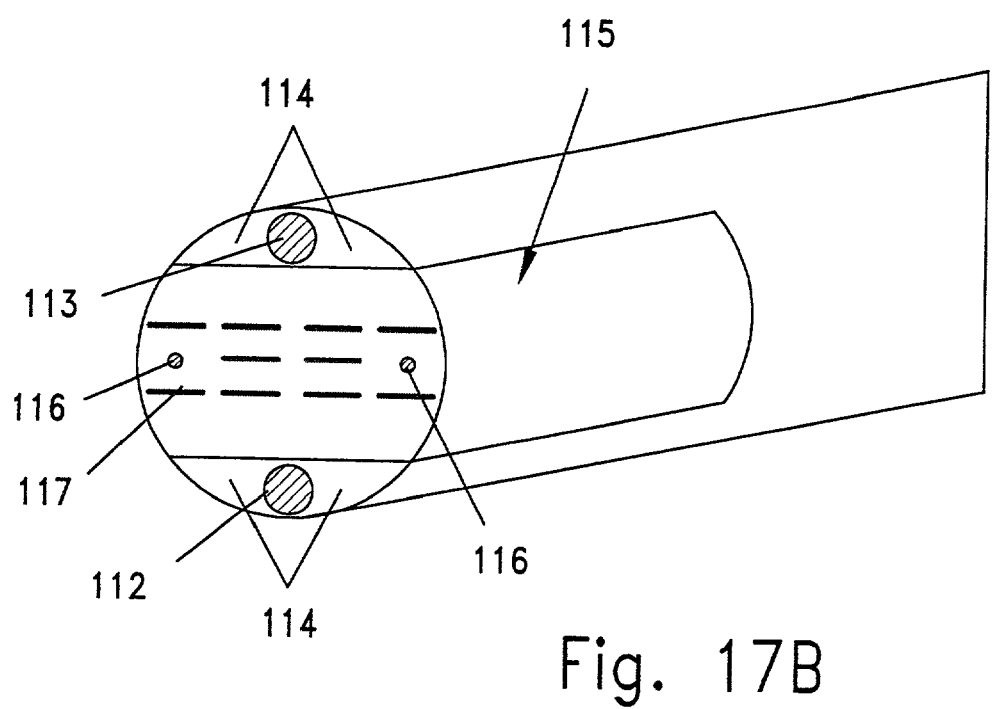
FIG. 17B shows the distal tip of the endoscope of FIG. 17A, with the anvil module of the stapler assembly in place.

FIG. 17B shows the distal tip of FIG. 17A with the anvil unit 115 in place. Numerals 112, 113, and 114 represent the same parts shown in FIG. 17A. Numeral 116 designates the holes through which the alignment/locking pins exit the anvil unit and 117 the depressions on the anvil unit face for curling the staples.

Figure 18A:
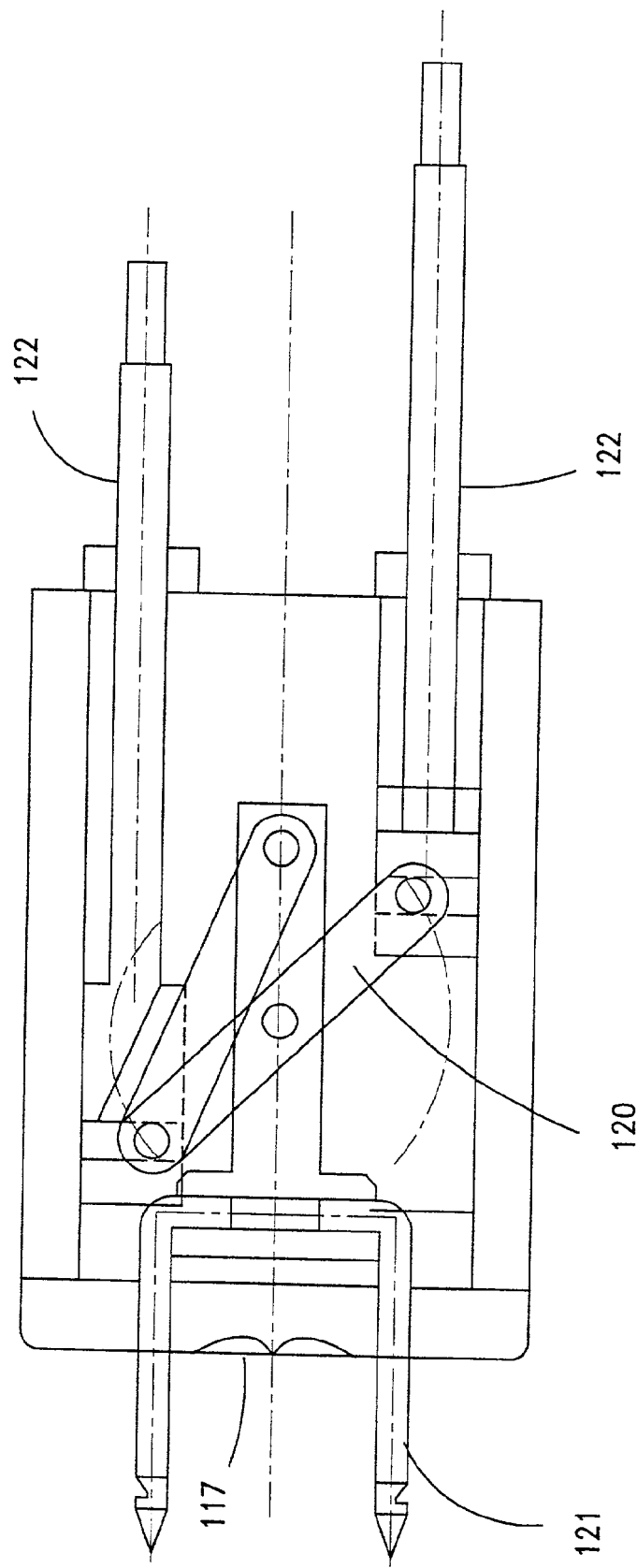
FIG. 18A is a cross-section showing the internal parts of the disposable anvil unit, according to an embodiment of the invention.
Figure 18B:
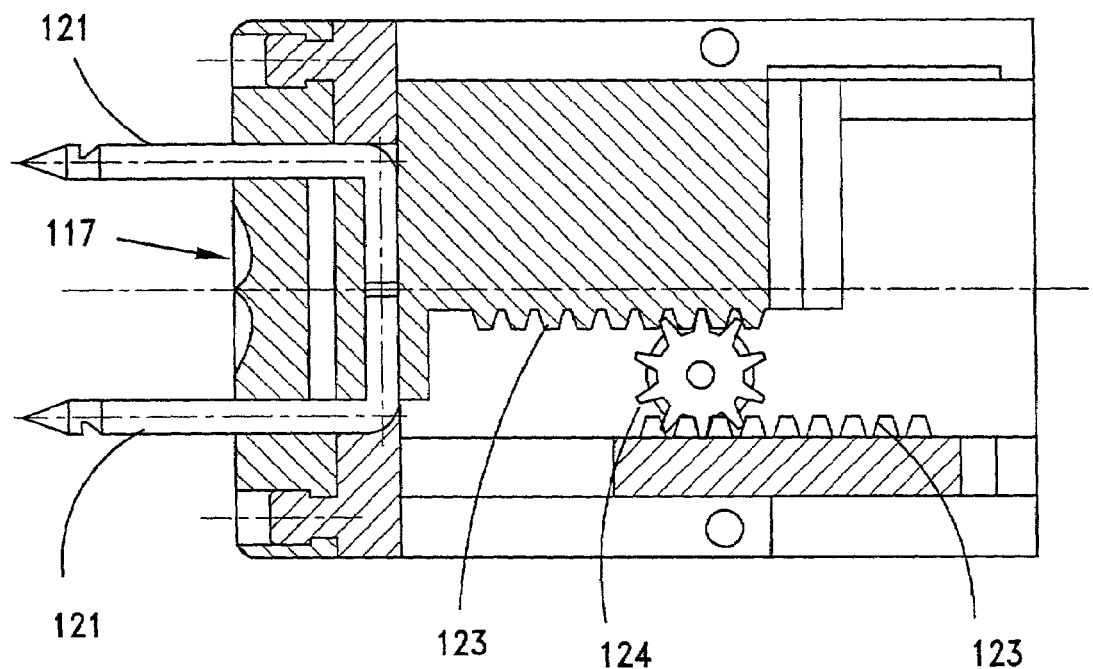
FIG. 18B is a cross-section similar to that of FIG. 18A showing the internal parts of the disposable anvil unit, according to another preferred embodiment of the invention.

FIGS. 18A and 18B are cross sections showing the internal parts of the disposable anvil unit that are needed to explain its operation. Two different systems are depicted in these figures.

Figure 18C:
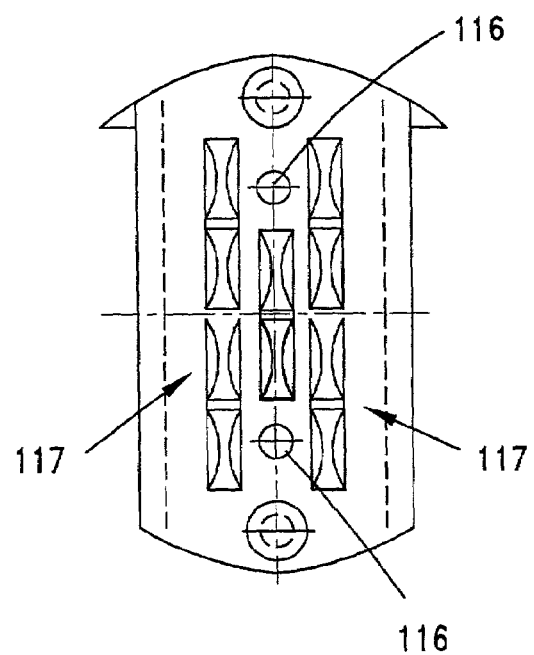
FIG. 18C shows the face of the anvil unit of FIG. 18A or FIG. 18B.

In FIG. 18A. the actuator mechanism 120 is employed to advance and retract the retention/locator pins. FIG. 18B depicts another preferred system. Within the support housing is located a dual rack 123 and single pinion 124 system to provide the desirable motion of the two retention/locator pins 121. Numeral 117 designates the depressions in the face of the anvil which cause the curling of the staples. The face of the anvil, showing the pattern of five staples used in the preferred embodiment of the invention, is shown in FIG. 18C. In this figure, 117 represents the depressions for curling the legs of the staples, and 116 are the holes through which the retention/location pins are projected. In FIG. 18A, numeral 122 designates the plungers that are part of the anvil holder and not of the disposable anvil unit.

Figure 19A:
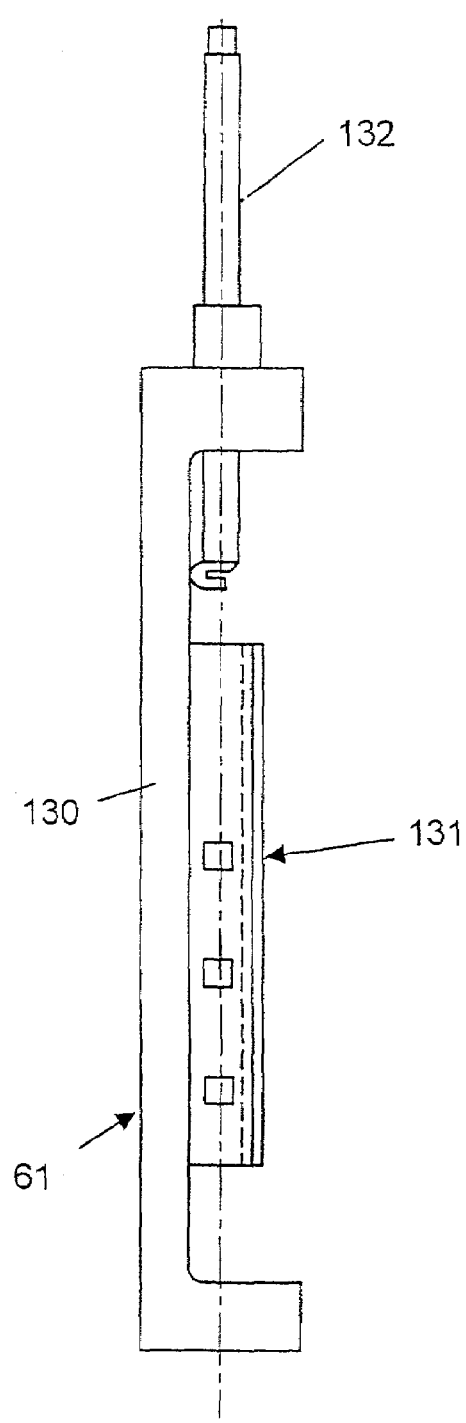
FIGS. 19A and 19B schematically show side and front views respectively of the staple cartridge holder, according to a preferred embodiment of the invention.
Figure 19B:
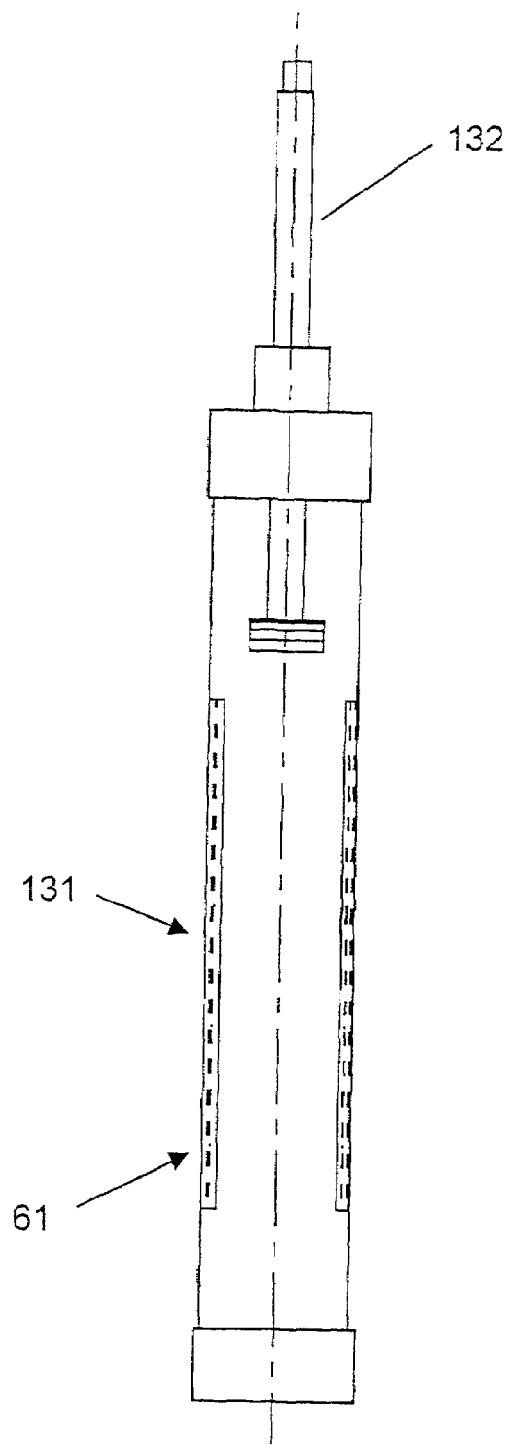

The second part of the stapler consists of a staple cartridge holder with disposable stapler cartridge located in the fixed portion of the endoscope shaft, proximate to the articulation section in the preferred embodiment of the invention. FIG. 19A is a side view and FIG. 19B is a front view that schematically show those parts that are located at 101 in FIG. 16A. The staple cartridge holder 130 consists of a tube of appropriate inside and outside diameters with a cutout in the profile. Within, the cutout is fitted with a piece of formed sheet metal (not shown) that forms a hermetic seal and retains the disposable staple cartridge 131 in the appropriate location with accurate index locations for the transfer of the staple cartridge for subsequent firings.

Attached to the tube and sheet metal subassembly is a plunger guide complete with a seal fitted with a plunger (collectively designated by the numeral 132). The plunger fires an array of staples when pulled in a proximal direction and then indexes the staple cartridge to the next position by a push motion in the distal direction.

Figure 20B:
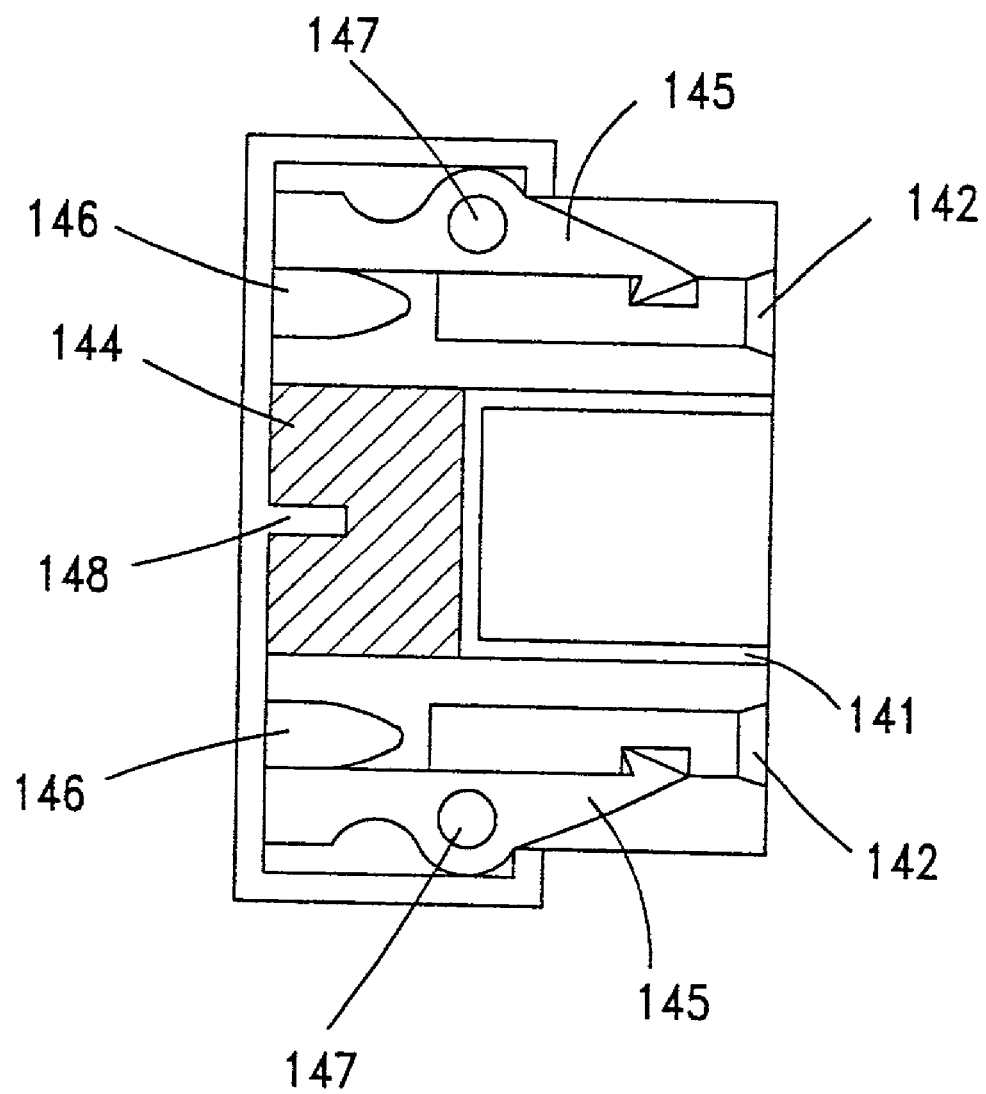
FIG. 20B is a cross-section taken along the A—A plane of the cartridge holder body of FIG. 20A.
Figure 21:
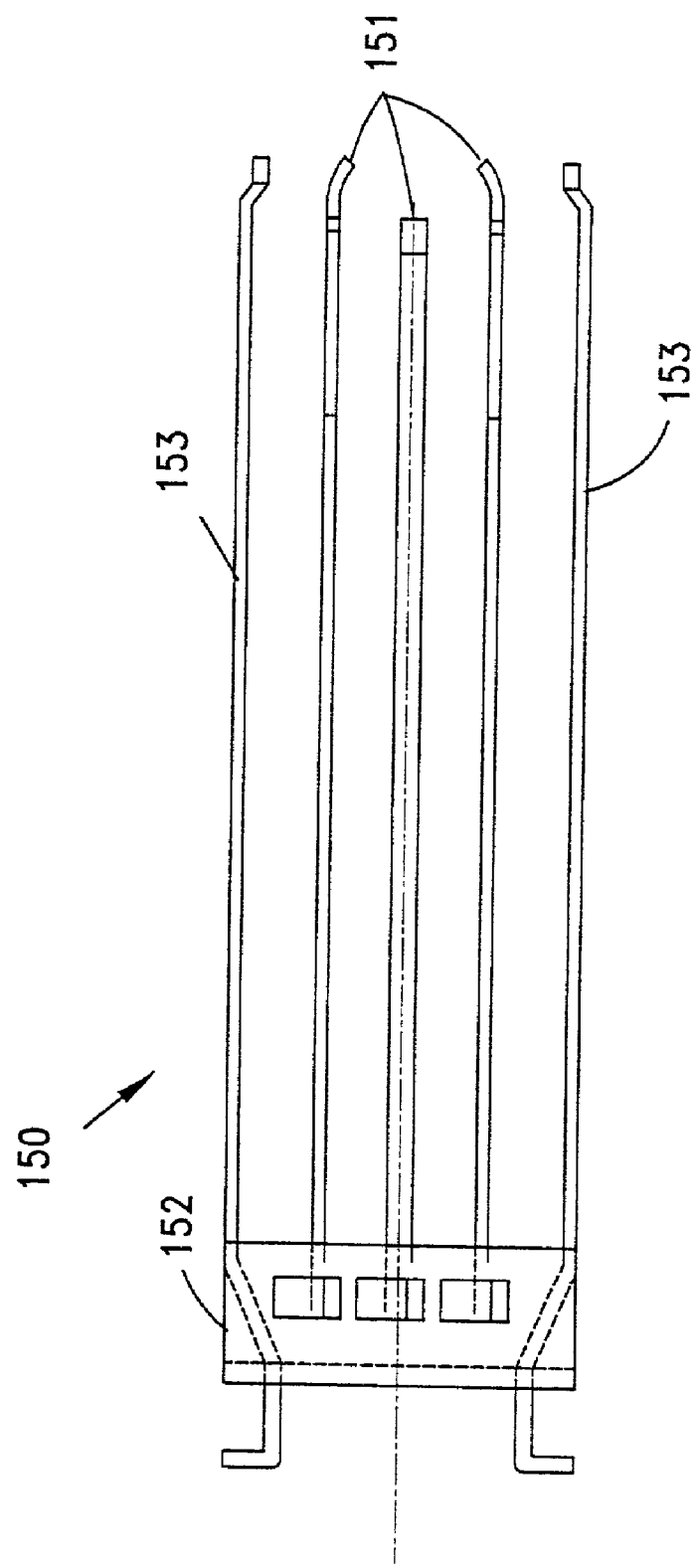
FIG. 21 shows the activation cam subassembly of the stapler cartridge of FIG. 20A.

The disposable cartridge case contains two subassemblies, the cartridge body that is illustrated in FIGS. 20A and 20B and the activation cam subassembly that is illustrated in FIG. 21.

Referring to FIG. 20A, the staple cartridge is made of stainless steel or other suitable material such as a suitable plastic and consists of the cartridge body (generally indicated at 140) that, in the preferred embodiment of the invention shown in this figure, retains three arrays each composed of five staples 141 and their respective pushers (shown in FIGS. 20B and 22A–22D) at an appropriate distance. With each array of staples are two holes 142 complete with latches and springs, to bias the latches in the desirable direction for latching onto the location/retention pins that protrude form the anvil. Three windows 143 in each side of the cartridge body, that are needed for indexing the cartridge are also present.

Figure 22A:
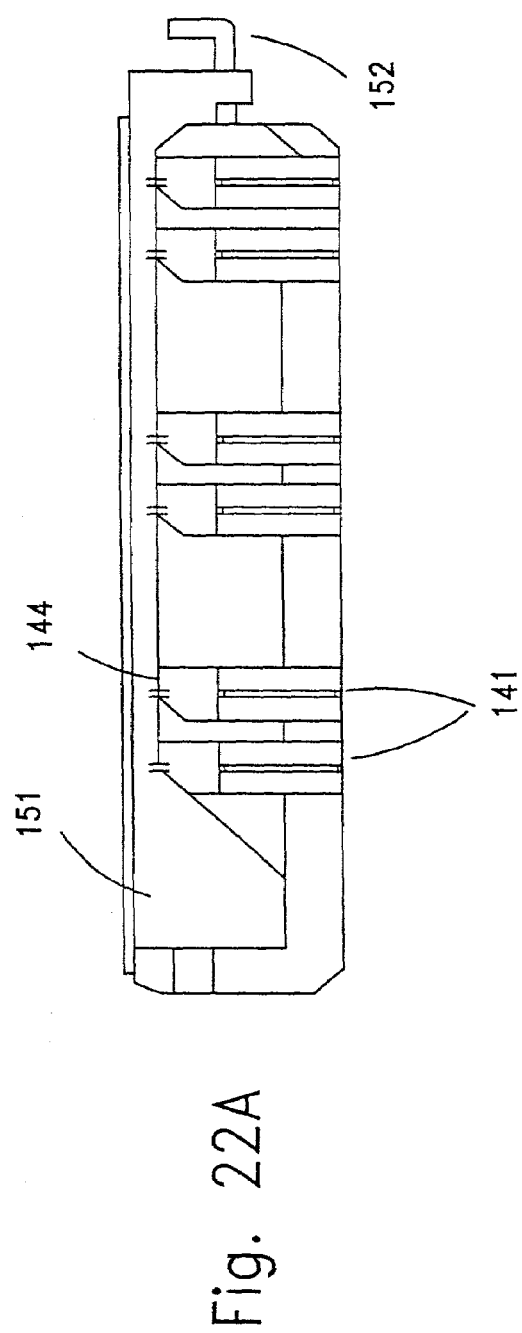
FIG. 22A is a side view of the cartridge body of FIG. 20A showing an activation cam.
Figure 22B:
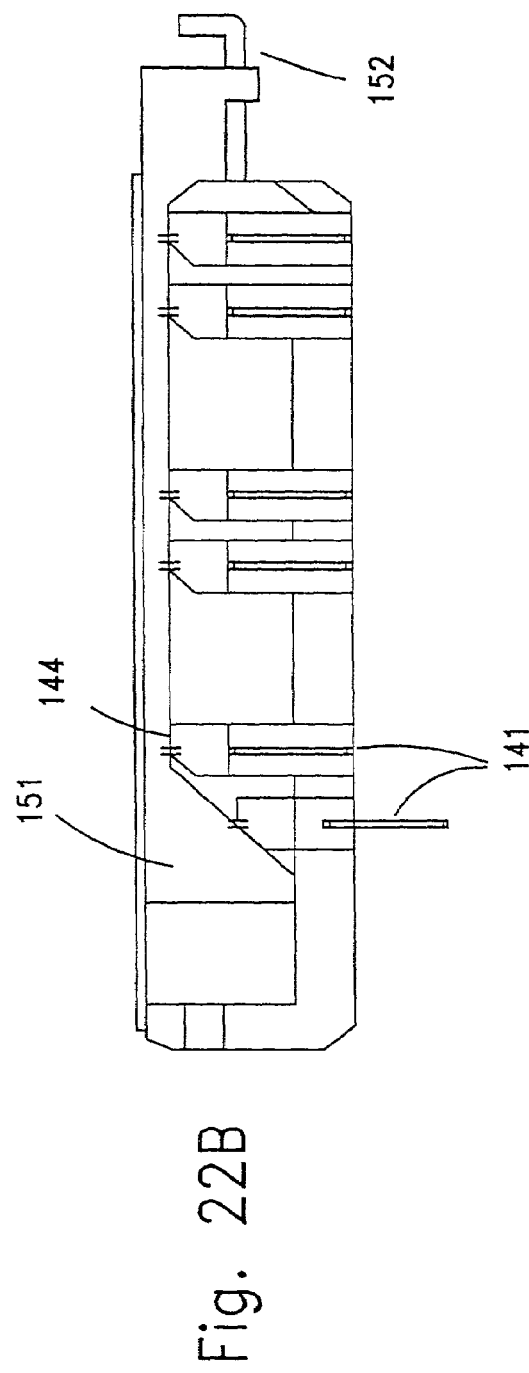
FIGS. 22B, 22C, and 22D illustrate the firing of the staples.
Figure 22C:
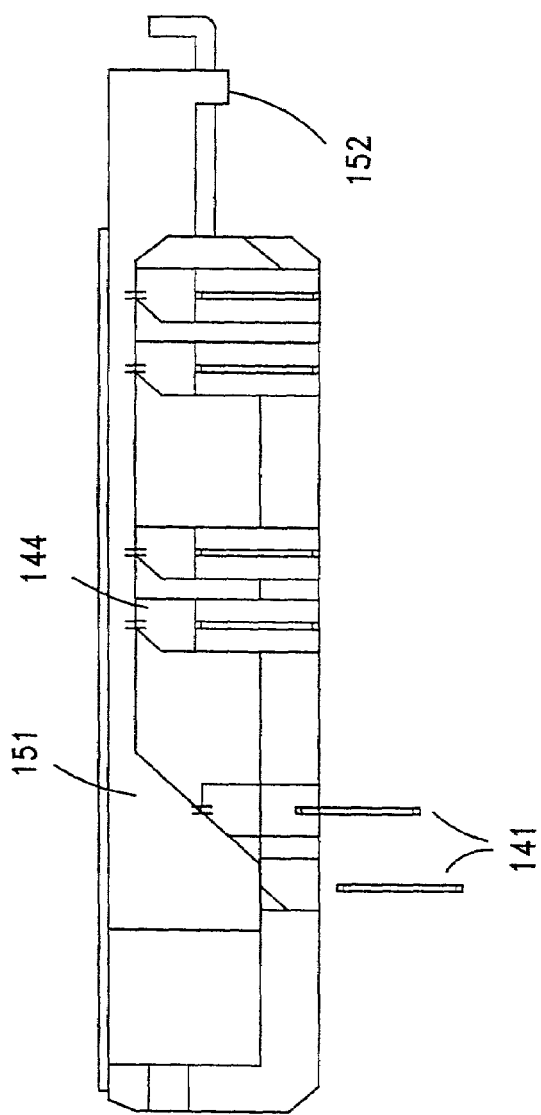
Figure 22D:
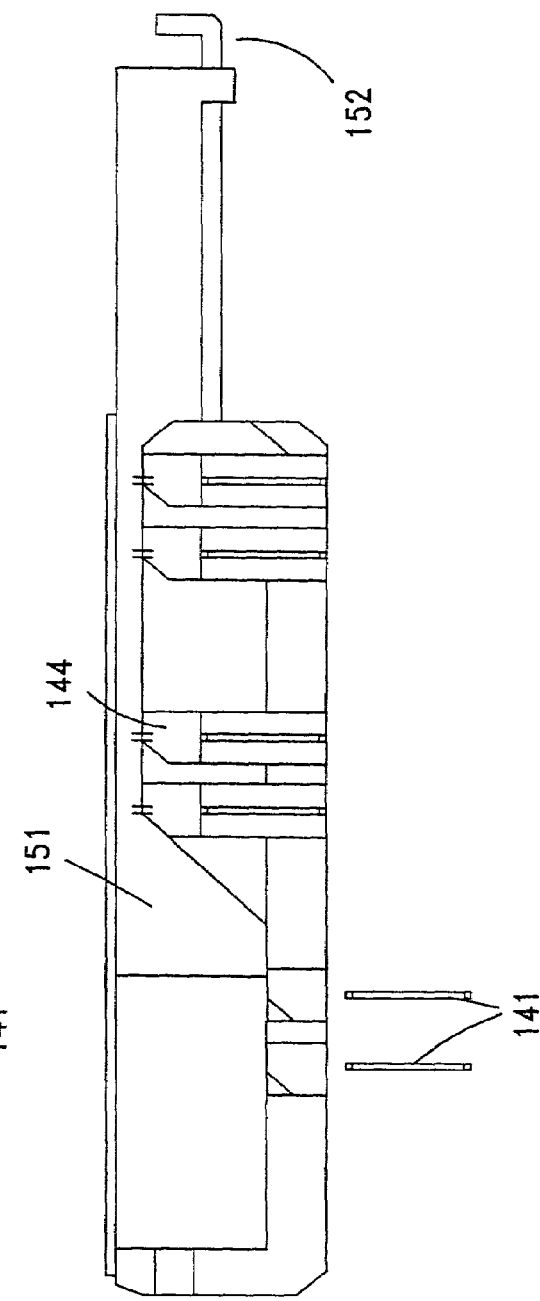

FIG. 20B is a cross-section of the cartridge body of FIG. 22A, taken along the A—A, plane, that schematically shows the major elements of this subsystem. In the figure, the numeral 142 designates the holes shown in FIG. 20A. This view shows schematically the beveled entrance to each hole, that allows for easier entrance of the pin into the hole and therefore pulls the two portions of the stapler into exact alignment as the pin enters the hole. The middle staple of the array is designated 141, and its pusher is indicated by the numeral 144. Numeral 145 designates the pawl and numeral 146 the leaf spring the function of which is to lock the location/retention pin in place during the firing of the staples. In FIG. 20B, the numeral 147 designates the pivot of the latching pawl and a cutout in the pusher for the cam is shown at 148.

The cartridge has a sheet metal housing that encases it on the three sides and holds the cartridge together and keeps all the activation cams in place. The housing is shown in a side view in FIG. 23A and in a top view in FIG. 23B. It has two angled portions 149 that lock into one set of windows on the cartridge housing, to prevent the cartridge from moving proximally while the cams fire an array of staples, and which are then used for accurate location to the next position when indexing distally.

The activation cam subassembly, shown generally in top view at 150 in FIG. 21, consists of three angular cams 151 that activate the staple pushers 144 (FIG. 20B) that fire the staples 141 in FIG. 22A. FIG. 22A is a side view that shows the relationship between these elements. The three cams 151 are welded or otherwise retained to a cross member 152. The outside two of those cams also have tails that are formed slightly to ratchet into position in the cartridge for indexing into the next position.

Two other components 153, in FIG. 21, exist on the extreme outside. These are devices the function of which is to release the locking pawls and thus free the alignment/retention pins after firing of the array of staples. They are not welded to the cam assembly due to space constraints and because a dwell is required prior to initial movement. They are activated by the cross member 152 that is part of the cam assembly.

While in the above description of the preferred embodiment of the invention, a staple cartridge containing three pairs of windows for indexing and three cams for firing three arrays of five staples each is described, it should be clear that other arrangements can be provided containing different numbers of arrays and different numbers of staples per array, depending on the requirements of the procedure that is to be performed.

It should also be clear to the man of the art that the positions of the stapler deployment system and the anvil can be interchanged, and that the elements of the stapler can be located at different positions along the long axis of the endoscope. For example, one part of the stapler system can be located proximally from the connection between the articulation and flexible sections within the flexible shaft of the endoscope. It is even possible, in certain cases, to reduce the radius of curvature of the device by placing the staple cartridge on one of the links of the articulation section, for example, if only one array of staples is to be fired.

Figure 24A:
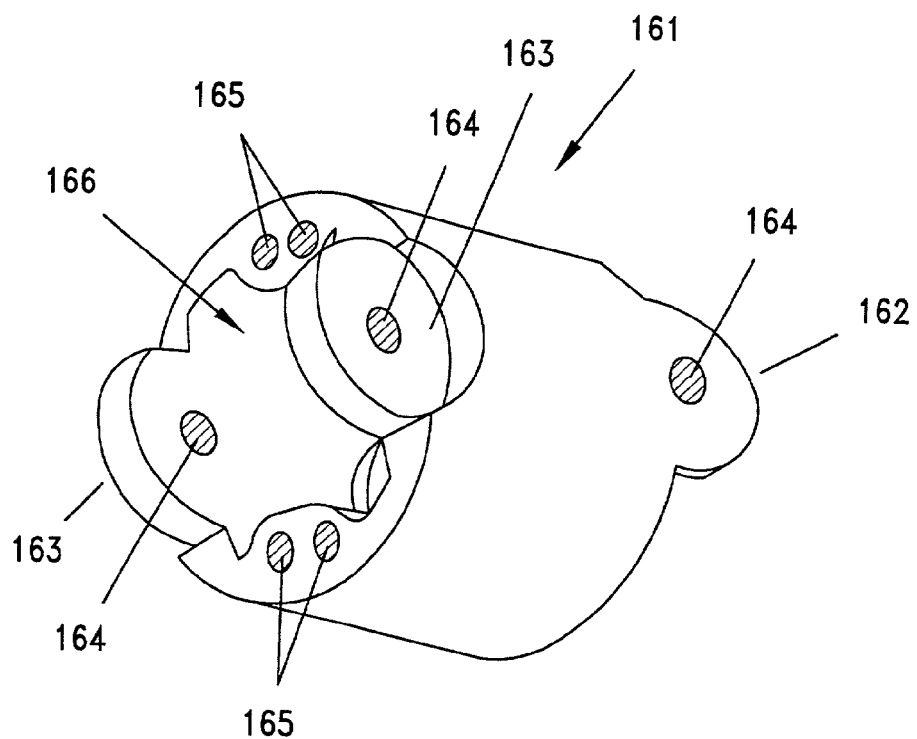
FIG. 24A shows a link of the articulation section of the endoscope.
Figure 24B:
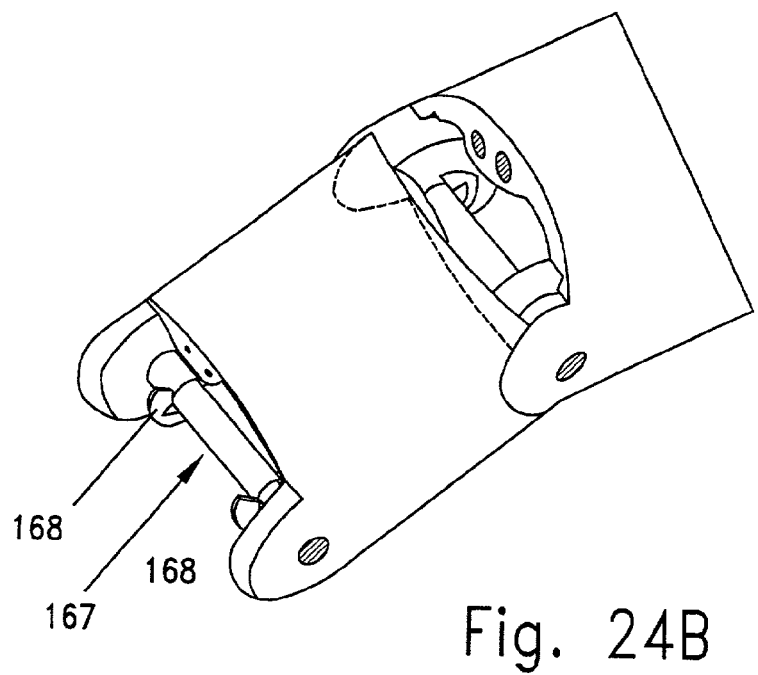
FIG. 24B shows the connection between two of the links shown in FIG. 24A.

The main features of the articulating section of the endoscope according to one preferred embodiment of the invention are shown in FIG. 24A and FIG. 24B. A typical link of the articulation section is generally shown as 161 in FIG. 24A. Each link is fabricated with a pair of circular lugs 162 with outer surfaces flush with the outer surface of the link at one end and a second pair of lugs 163 that are recessed by the thickness of lugs 162 at the second end. Each of said lugs is pierced by a hole 164. Four holes 165 are drilled in the link walls for the cables that are needed for articulation. A hollow region 166 through the center of each link allows the passage of optical, illumination, suction, etc. channels to the distal tip of the endoscope.

FIG. 24B shows the connection between two of the links of FIG. 24A. The pair of lugs 162 of the first link is slipped over the recessed lugs 163 of the second link. A swivel pin 167 is inserted through holes 164 in the lugs and retaining clips 168 may be added to complete the assembly. In another particular preferred embodiment of the device shown in FIG. 24B, retaining clips 168 are not provided.

Design parameters such as the length of the links, clearance (maximum bending angle) between links, and radius and maximum angle of curvature of the entire section determine the number of links that are joined together to form the articulation section. The outside ends of the first and last links are designed to interface with the rest of the endoscope and its distal tip, respectively.

The swivel pins contain cross-holes for the cables which must pass through them. These cross-holes and cables are not shown in FIGS. 24A and 24B.

In the preferred embodiment of the invention, the articulation section uses one pair of cables (or a single cable wrapped around a wheel located at the proximal end of the endoscope) for actuating the articulation. One cable passes through the hole in the link wall on the inside of the bending arc, and bends the endoscope into the bent position. The second cable is located opposite the first one, and unbends the section. The actuation mechanism is well known to persons skilled in the art, and need not be described here.

In another embodiment of the invention, a four-way articulation system is employed. In a four-way system the tip of the endoscope can be moved in two mutually perpendicular planes. This gives more degrees of freedom of movement, but complicates the alignment procedure and necessitates the use of one of the alignment systems to be described below. Four-way systems are well known in the art and therefore will not be described here for the sake of brevity.

The detailed description of the way in which the stapler system functions will be given below with the schematic description of a typical surgical operation that can be performed using the device of the invention, i.e. the fundoplication operation designed for the treatment of GERD.

Positioning markings 64 may be located on the device (as indicated in FIG. 5), at the extremity outside the patient, to provide information on the location of the device that has been introduced into the patient.

Endoscopic vision means can also be provided. FIGS. 17A and 17B schematically show the distal tip of the endoscopic device. Regions 114 are the illumination channels, 113 is the image channel, and 112 is the irrigation/suction/ultrasound channel. Placement of imaging means at the distal tip assists in guiding the device to the desired position in the body lumen and allows imaging of the area during the performance of the surgical procedure. A second optical image can be provided. This image will be a view through a clear portion of the stapler and will show the staples as they are passed through the tissue and bent closed. These optical systems of conventional endoscopic apparatus can be employed. The endoscope may contain two or more separate optical channels that produce two or more distinct views. Preferred endoscopic optical systems according to an embodiment of the invention, will be described hereinafter. However, many different optical systems may be provided by persons skilled in the art, and used together with the apparatus of the invention.

In the preferred embodiment of the invention described above, the alignment of the two separated parts of the stapler is accomplished by strictly mechanical means made possible by the use of a fixed radius of curvature and precise design and manufacture of the stapler and articulation section of the endoscope. In some alternative embodiments of the invention, however, it may be necessary to provide an aligning assembly of the kind described above.

In other preferred embodiments of the invention that use four-way endoscopes, one of such means must be used to align the two sections of the stapler. The surgeon is able to verify the positioning, the proper distention of the fundus towards the esophagus, and the results of the stapling, by using the visual means provided at the distal tip of the endoscope. If the endoscope is furnished with an optical system according to the preferred embodiment of the invention described below, a second independent optical path is provided. Thus the surgeon can view the site from the side of the staple firing portion before and after the firing has been accomplished. Further as the two parts of the stapler are pressed together, the tissue is pressed between them and it is possible to see through the tissue allowing visual confirmation of proper positioning and alignment of the device.

Final alignment is accomplished by deploying the locking pins that are located in the anvil portion of the stapler. The method of accomplishing the deployment of the location/latching pins, in a preferred embodiment of the invention, was described with reference to FIGS. 18A, 18B, and 20B.

The techniques used to activate the plungers in the anvil section and also the firing plunger in the staple cartridge holder are well known to the man of the art and therefore will not be discussed here for the sake of brevity. As the pins advance into the holes in the staple holder, they are engaged and locked by the pawls (145 in FIG. 20B). The cable that advances the pins is now relaxed and the other cable is then activated to confirm the locking by the pawls, clamp the tissue, and provide the desired tissue gap.

Figure 26A:
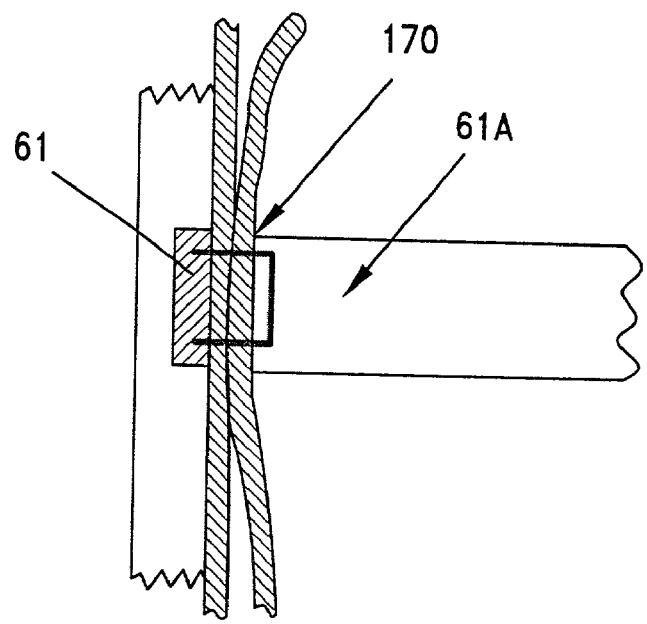
FIG. 26A schematically illustrates the stapling procedure showing the locking needles deployed from the anvil and locked into the staple cartridge.

FIG. 26A illustrates the situation at this stage of the surgical operation. The locking pins (collectively indicated at 170), that were stored in the anvil assembly 61A, have been deployed through the tissue of the fundus and esophagus walls, and have been locked into the sockets in the stapler cartridge 61. The locking pins not only assure proper alignment, but also maintain the desired tissue gap during the stapling. The locking pins (or similar or equivalent locking means) are the reason that the stapler of this invention can function with a totally flexible connection between its two sections as opposed to the rigid or semi-rigid connection between the anvil and staple container/ejector parts of the staplers of the prior art.

To fire an array of staples, a cable attached to the firing plunger (132 in FIG. 19A and FIG. 19B) is then pulled proximally. This pulls back the cross member (152 in FIGS. 21 and 22A to 22D) with the attached cams. The process of firing the staples can be understood from FIGS. 22A to 22D. As the cam (151) moves proximally, its angled surface engages the angled surface of the staple pusher (144) forcing the pusher to move sideways towards the wall of the cartridge and forcing the staple (141) out of the side of the cartridge through the tissue of the walls of the esophagus and stomach. The legs of the staple engage the depressions on the face of the anvil and start to curl. FIGS. 22A through 22D show various stages in the firing of one array of staples. After all staples of the array are fired, the release cams (153 in FIG. 21) exert force on the proximal end of the pawls to release the latching of the pins. The distal cable that activated clamping is pulled to withdraw the pins into the anvil and this phase of the surgical operation is completed.

Figure 26B:
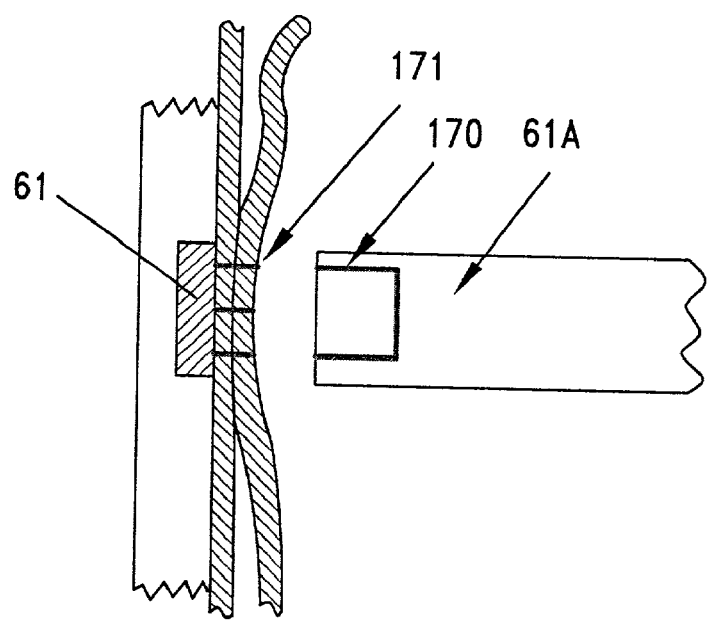
FIG. 26B schematically illustrates the stapling procedure showing the situation after the staples have been fired and the locking needles withdrawn.

FIG. 26B shows the situation after the stapling has been effected. Staples, (collectively indicated at 171), have engaged between the fundus and the esophagus, at the specific location on which it was operated.

The tiny holes in the tissue, that result from the action of the alignment/locking pins, are similar to holes produced by hypodermic needles, and seal themselves. The holes can be protected by the staple above and below it. In a preferred embodiment, a configuration consisting of three rows of staples with the pinholes aligned with the middle row (such as that illustrated in FIG. 18C) is chosen to achieve this end.

Figure 25A:
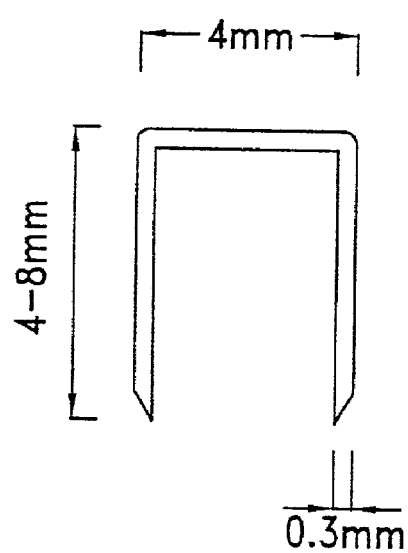
FIG. 25A shows the staple configuration before firing, typical dimensions being also indicated.
Figure 25B:
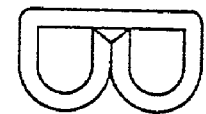
FIG. 25B shows the staple configuration after firing.

FIG. 25A shows a staple before firing. FIG. 25B shows the configuration of the staple after the legs are curled in the anvil.

After inspecting the staples the surgeon now releases the articulation section as needed and removes all clamping of tissue inside the stomach. The device is now rotated to the next location and the articulation/aligning procedure is repeated.

The outer two of the three firing cams have spring biased tails that allow the cams to move in one direction only. The firing plunger is now pushed distally and since the cams cannot move in that direction, this causes the whole cartridge to index forward to position the second array opposite the anvil. As the cartridge moves distally, the angled portions on the housing slide out of the first set of windows on the side of the cartridge. Indexing is completed when said portions snap into the second set of windows.

The process of final alignment, deploying and locking the location/locking pins, and firing the second array of staples is repeated. The whole process as described above is repeated a third time to complete the partial fundoplication (although the number of firings may vary, according to medical considerations).

In a preferred embodiment of the invention, the alignment/locking pins and/or the locking pawls are made of a suitable material such as stainless steel as a safety measure. This material is strong enough to allow the parts to function as described in normal operation, but the pin tips can be broken by the force exerted by unbending the articulating section in the event that the release cams fail to unlock the pins.

After many repeated operations of the endoscope, it is possible that wear of the parts, especially in the articulation section, will lead to difficulty in properly aligning the anvil on the distal tip with the stapler cartridge in the endoscope shaft. This difficulty can be overcome by displacing said portion of the stapling assembly along the axis of the endoscopic device by various means. According to a preferred embodiment of the invention this is achieved by the action of a flexible threaded cable coupled with a female thread located in said portion of the stapling assembly. In one preferred embodiment of the invention the flexible threaded cable is located within the endoscopic device, and is in contact with the female thread through a slit provided in the wall of the body of the endoscopic device. In another alternative preferred embodiment of the invention the flexible threaded cable is embedded in the external wall of the endoscopic device, and is in direct contact with the female thread of the portion of the stapling assembly.

In one preferred form of the invention the flexible threaded cable is rotated using a micrometric assembly, thereby to displace the portion of the stapling assembly positioned within the esophagus by a controlled distance.

Multiple Views

Figure 27:
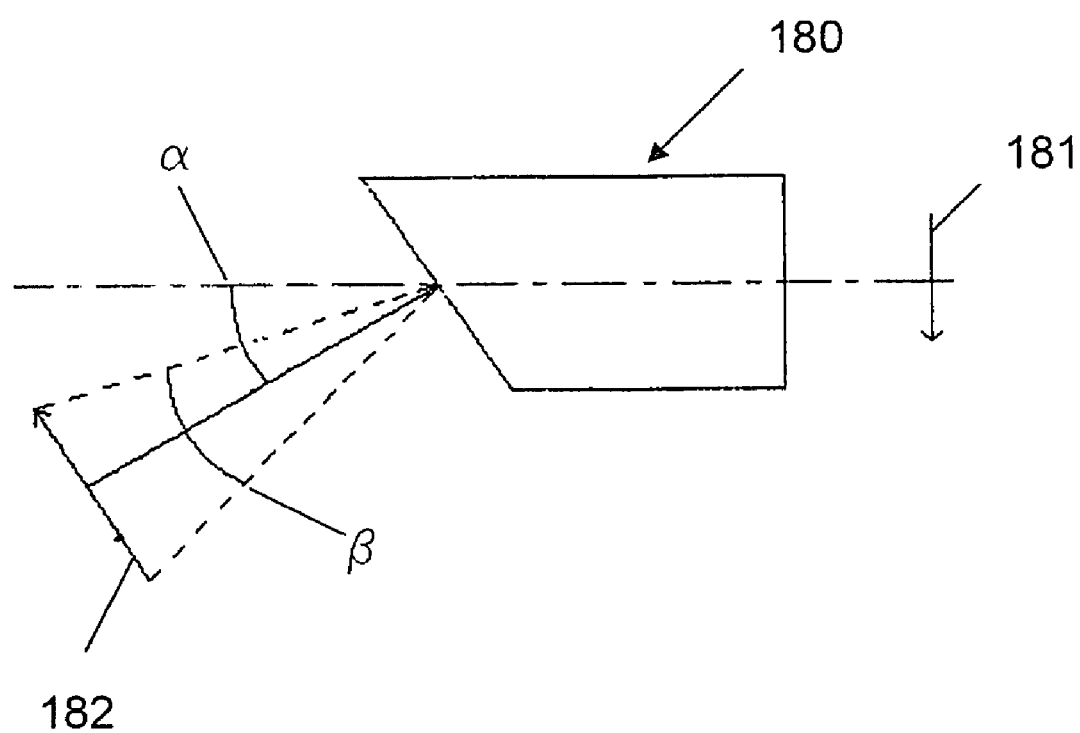
FIG. 27 schematically shows a typical endoscope objective.

Each of the multiple views of the invention is formed by an objective lens. FIG. 27 shows the configuration of a typical endoscope objective (180) and illustrates some of its properties. The angle between the mechanical axis of the distal tip of the endoscope and the optical axis as it enters the endoscope objective ($\alpha$) is the "angle of view". This angle of view refers only to the relationship between the optical and mechanical axes at the distal tip and does not take into account the variable direction of view provided by articulating (FIG. 6A) the distal tip of the endoscope. Typical values for angle of view may range between 0 and 120 degrees. Non-zero angles of view are usually achieved by the use of prisms or mirrors in the objective optics. The field of view ($\beta$) of the endoscope objective describes the angular extent in object space that the lens can image. Field of view can be very narrow, approaching zero degrees, or may range up to 180 degrees. For example, a telescope will have a very small field of view with high magnification, while wide angle lenses (also know as "fish-eye" lenses due to the curved appearance of the image) have large fields of view with low magnification. The larger the field of view, the smaller the details will appear in the image. The image (181) of the object (182) can be located at or behind the last surface of the objective lens.

Figure 28A:
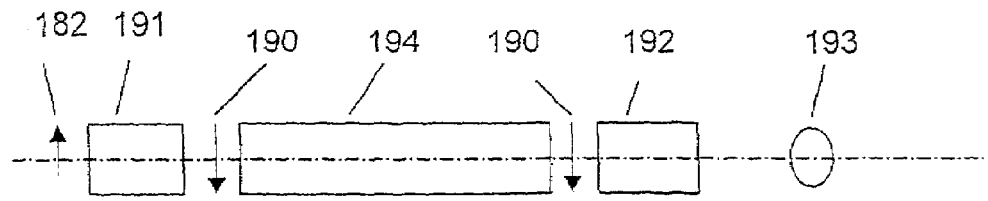
FIG. 28A through FIG. 28E schematically show endoscope configurations with a single optical channel.
Figure 28B:
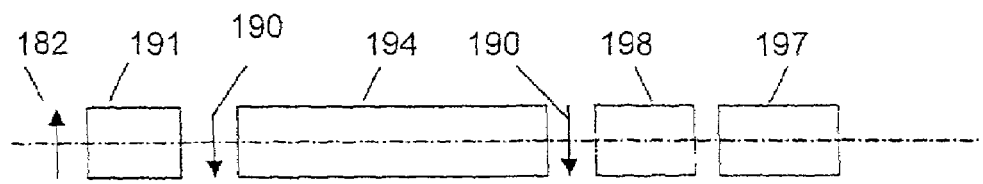
Figure 28C:
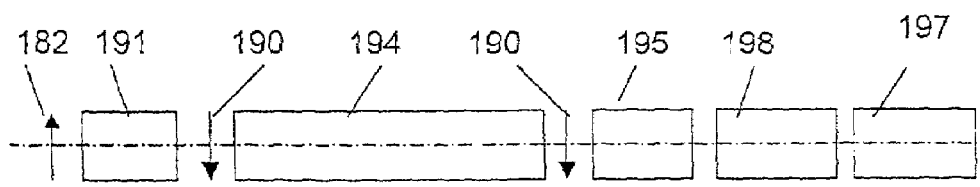
Figure 28D:
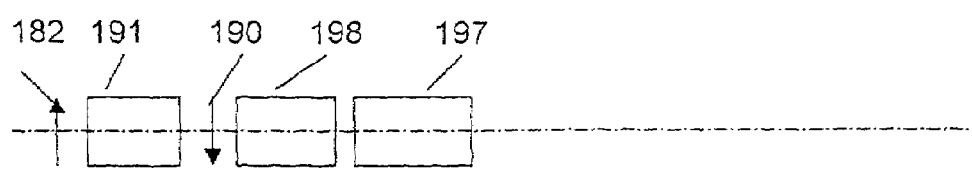
Figure 28E:

Looking at FIG. 28A through FIG. 28E, the image (190) formed by the objective lens (191) must be transmitted to a detector for viewing at the proximal end of the endoscope. An ocular (192) may be employed for direct viewing by the human eye (193), or the image may be formed on an opto-electronic sensor (197) (such as a CCD or CMOS sensor) that transforms the optical image into electronic signals. The electronic signals are then sent to a display, such as a video monitor, flat panel display, head-mounted display, or liquid crystal display, where the image can be viewed by one or more people. FIGS. 28A–E show several configurations for each individual viewing channel of the present invention. FIG. 28A shows an objective lens (191) coupled to an ocular (192) by a relay optical system (194). A relay is an optical subsystem of the endoscope that transmits an image from the objective image plane to another location. Since an endoscope is usually much longer than the distance from the first surface of the objective to the objective image plane, relays are used to bring the image up to the proximal end of the endoscope, where it can be accessed by the viewing optics. Relays may consist of lenses or other optical imaging elements, or alternately a coherent (ordered) fiber optic image guide may be employed to transmit the image. Fiber optic image guides are usually used for flexible or semi-flexible endoscopes, while rigid endoscopes typically include a relay made up of a series of glass rods and lenses. FIG. 28B shows an objective lens (191) and relay (194) used in conjunction with an image sensor (197) connected optically via a coupling lens (198). The coupling lens images the relay's proximal image plane onto the surface of the sensor, where it is converted to an electronic signal and sent to the display for viewing. FIG. 28C shows an option in which an endoscope objective lens configured as shown in FIG. 27 is coupled to an image sensor (197) by a coupling lens (198) that clips or attaches onto the ocular (195) mount. FIG. 28D shows a configuration where the relay system is not used, and the image (190) is coupled directly from the objective image plane to the sensor surface (197) by a coupling lens (198). FIG. 28E is a similar option wherein the sensor surface may be placed directly in the objective image plane. This type of endoscope is sometimes referred to as a "chip-on-a-stick", and the sensor is imbedded in the distal end of the shaft instead of being located externally or at the proximal end.

If an image sensor is utilized, there are many options for displaying the multiple views provided by the invention. Single or multiple displays may be used, with single or multiple views on each display. Options include, but are not limited to those shown in FIGS. 29A–29C. In each scenario, the display may also convey other information such as status of built-in surgical tools, status of the articulation, or readouts from vital signs monitors for example. FIG. 29A illustrates having multiple views 200 and 201 arranged on a single display. The views may take on any shape and do not need to be of equal size. FIG. 29B shows multiple views 200 or 201 that are accessed on a single display by toggling between the views as needed. In another preferred embodiment of the present invention, a multiplicity of displays may provide visual access to a multiplicity of views. Each display may contain one or more views that can be accessed simultaneously, singly, or by toggling between views. One or more of the displays may also show status indicators or other information. As shown in FIG. 29C, one display is showing view 200 individually, a second display is toggling between views 201 and 205, and the third is presenting views 202, 203, and 204, simultaneously with status indicators 206.

Figure 30A:
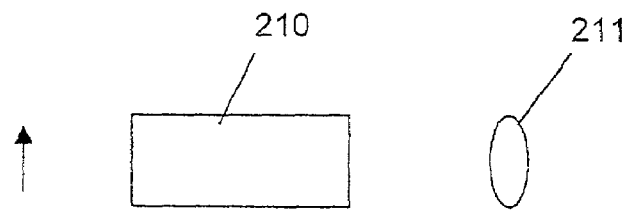
FIG. 30A schematically shows the ocular types for monocular viewing.
Figure 30B:
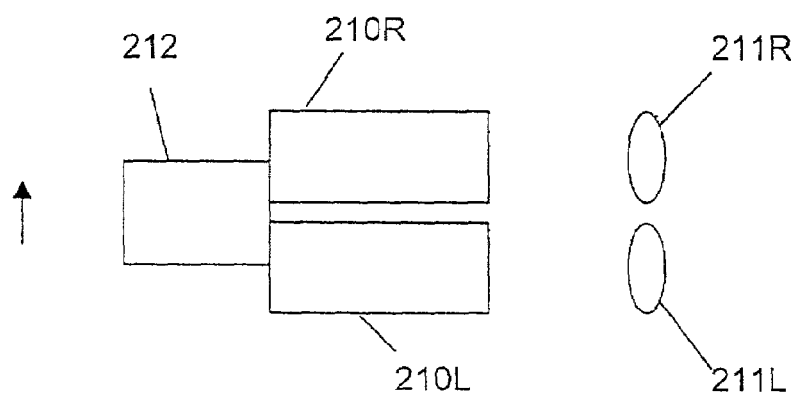
FIG. 30B schematically shows the ocular types for biocular viewing.
Figure 30C:
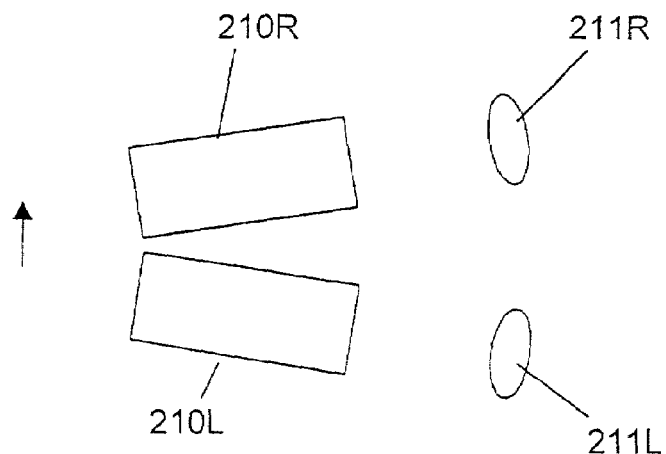
FIG. 30C schematically shows the ocular types for stereoscopic viewing.

FIGS. 30A–30C show different ocular types for monocular, binocular, and stereoscopic viewing. It is important to note that while stereoscopic viewing may be provided for one or more of the multiple views, the optics used to provide a stereoscopic view do not present "multiple views" as defined with reference to the present invention. Key differences are that stereoscopic optical channels provide slightly offset images of the same object area; while in the present invention the optical channels that provide multiple views have substantial linear or angular offsets, or both, and do not provide images of the same object area. FIG. 30A illustrates the schematic for monocular viewing, which is typical of most endoscopes that include an ocular. One ocular 210 provides access to the image for a single eye 211, which can be either the left or the right eye. Biocular optics use splitting optics 212 to provide the same exact image to both eyes via two oculars, one for each eye as shown in FIG. 30B. Here the addition of the letters "L" and "R" designate left and right for both the oculars 210 and the eyes 211. The stereoscopic ocular arrangement shown in FIG. 30C provides a slightly offset view of the image to each eye (211L and 211R) via two oculars (210L and 210R) that are offset. This simulates normal human vision where each eye captures a slightly offset view and allows for some depth perception.

Figure 31A:
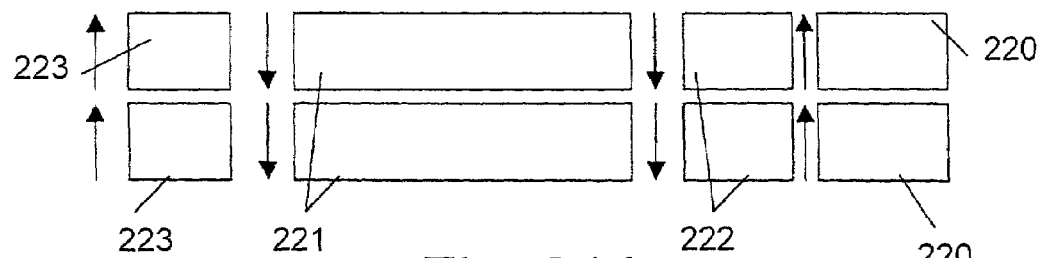
FIG. 31A through FIG. 31D schematically show different configurations for the dual optical channels for dual views.
Figure 31B:
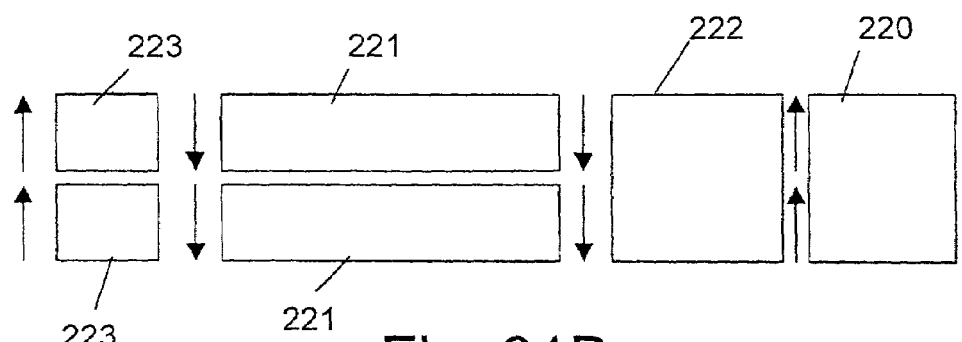
Figure 31C:
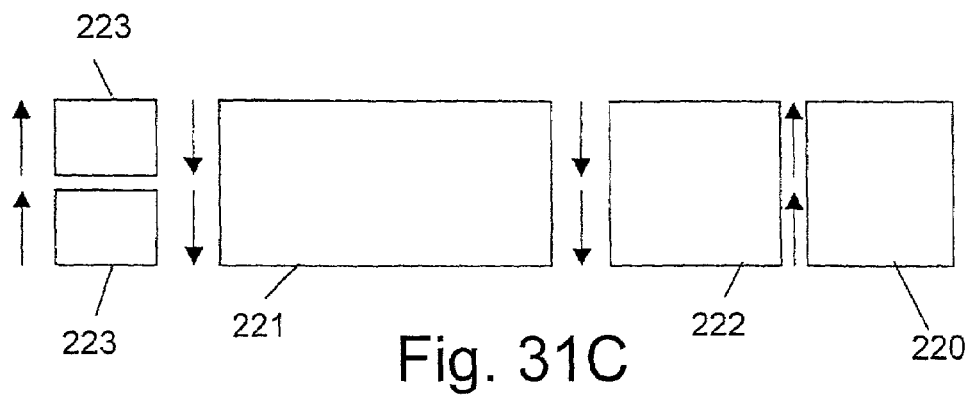
Figure 31D:
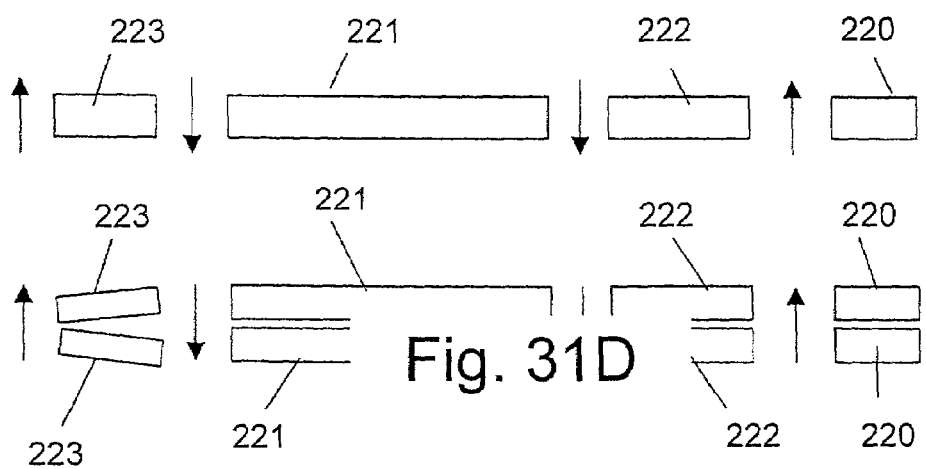

According to a preferred embodiment of the present invention, each of the multiple views is formed by a unique objective lens (or pair of objective lenses for stereoscopic viewing). This means that at the distal end, there will be one optical channel per view (or two for stereoscopic viewing). These separate optical channels may continue through the entire endoscope as shown in FIG. 31A. This figure shows an endoscope having two views. Each view is carried to a separate image sensor 220 by its own unique optical channel. Since there are two views, there are two objectives 223, two relays 221, two coupling lenses 222, and two sensors 220. In FIG. 31B, an alternative is shown where the endoscope has two views, that have unique objectives 223 and relay optical channels 221, and a single coupling lens 222 and image sensor 220 captures both views. The coupling lens and sensor may image the views together, or one at a time by switching between them actively or passively. A third alternative, shown in FIG. 31C, has two unique objectives 223 that capture two views, with a single relay system 221, coupling lens 222, and sensor 220 providing access to the views. As in the system shown in FIG. 31B, the access may be simultaneous or one at a time. FIG. 31D illustrates an endoscope having two views, one of which provides stereoscopic imaging. The upper (non-stereo) view is carried by a single optical channel. The lower (stereo) view contains a set of two optical channels that are slightly offset at the distal end. The two optical channels present images of the object that originate from slightly different locations. This simulates normal human vision in which each eye views a scene from its own unique location and the brain integrates the differences in the image on each eye to formulate depth cues.

Figure 32:
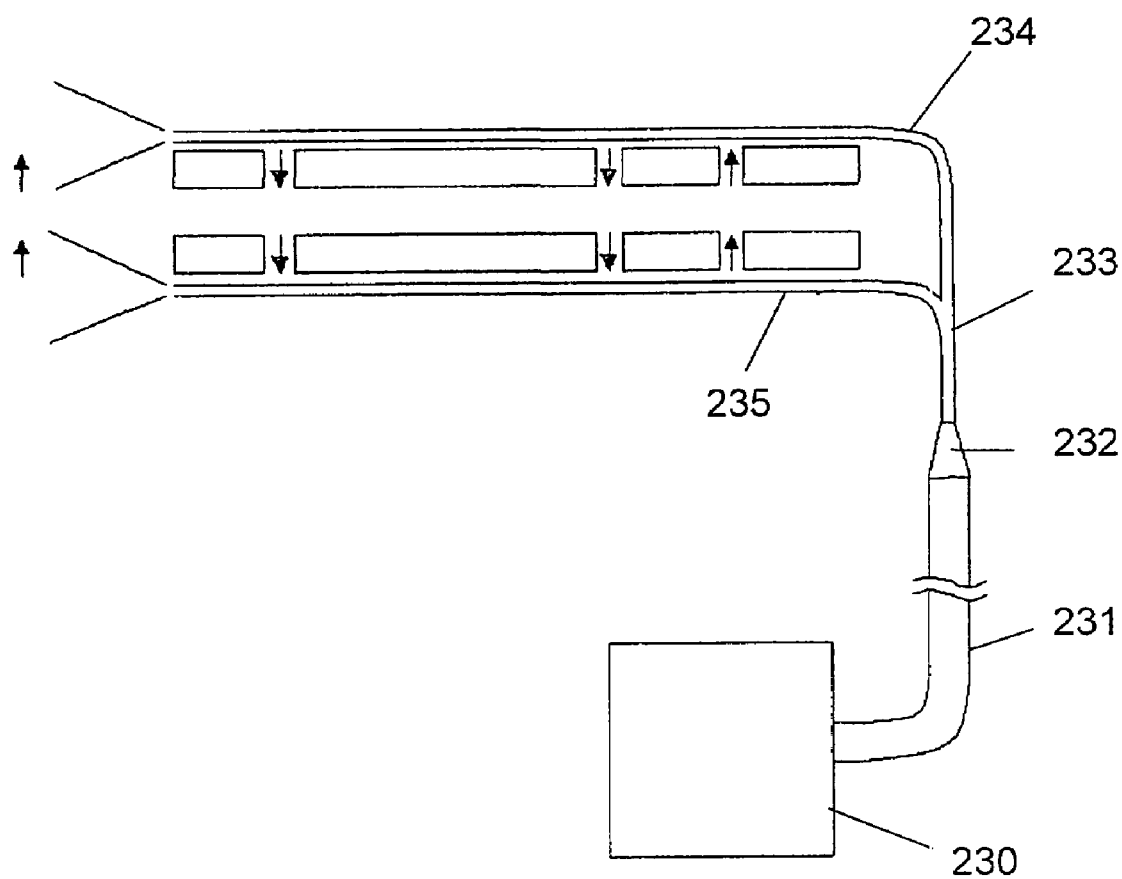
FIG. 32 schematically shows a typical endoscope illumination system.

According to another preferred embodiment of the present invention, the endoscope provides illumination to the views via single or multiple illumination channels. FIG. 32 shows one such configuration where an endoscope with two views (as illustrated in FIG. 31A) has a separate illumination channel for each view. Light from an external source 230 is transmitted to the endoscope via liquid-filled or fiberoptic cable 231. Coupling optics 232 at the interface insure that the light is efficiently coupled into the internal illumination fibers 233. The illumination fibers are split into two channels 234 and 235 internally within the endoscope to provide light to each view individually.

An illustrative preferred embodiment of the invention may consist of the following elements:
  Multiple optical channels;
    An optical channel at the distal tip to visualize insertion and stapling from the distal end (which also contains the stapler anvil);
    A second optical channel located at the stapling backstop on the endoscope side wall to visualize staple penetration inside the esophagus from the "stapler side";

A stapler module located intermediately along the endoscope shaft that may contain components of the optic system. This module is preferably disposable, but may be resposable or reusable;

A stapler anvil module at the distal tip that may contain components of the optic system. This module is preferably disposable, but may be resposable or reusable;

A robust, one-way articulating section e.g. capable of up to about 270° articulation to distend the fundus of the stomach and position the stapler; and A single display showing both views simultaneously, with optional status indicators for the endoscope articulation, stapling operation, or both.

Figure 33A:
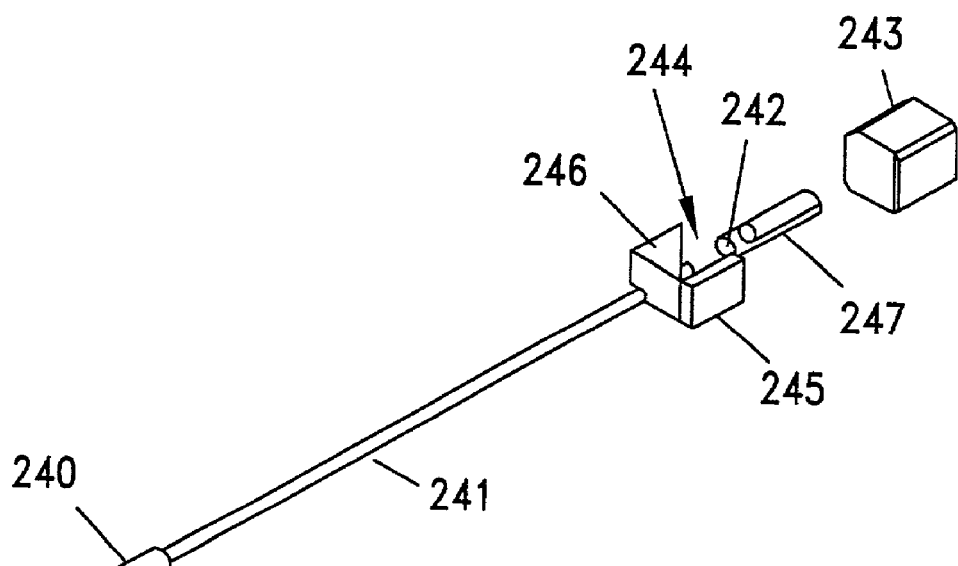
FIG. 33A is a schematic view of an optical assembly showing dual optical channels.

In order to see both sides of the staple as it is placed, and to assure proper joining of both fundus and esophageal tissues, a preferred embodiment of the invention employs the use of two optic channels (FIG. 33A). In this embodiment, an objective lens 240 captures the image from the tip of the scope (the "distal view"). A flexible fiberoptic image guide 241 carries the image about 12 cm proximally where it is focused by a coupling lens 242 onto a CCD sensor 243. This view fills the main part of the video monitor (251 in FIG. 34), and is always displayed, since it is used during insertion, distention, and stapling. A "stapler view" (252 in FIG. 34) is simultaneously projected onto one corner of the CCD and thus appears in one corner of the monitor. This is a view from the endoscope shaft, looking sideways from the vicinity of the stapler which is located at position 244 in FIG. 33A. The optical path of this image starts with an object perpendicular to the axis of the endoscope. The optical path travels through the stapler backstop 245 and clear portions of the stapler module and with the aid of right angle prism 246 and objective lens 247 an image is produced on the CCD 243. This view may only be activated during the stapling process. After stapling, the distal view shows the closed staple(s) from the stomach side, and the stapler view shows the staple(s) from the esophageal side. These multiple views provide confidence that each staple is properly placed before repositioning the instrument for the next shot.

The display may have the option of switching the second view off when it is not needed by controlling illumination to each view. The first view will typically be active continuously but also may be switched off.

Figure 33B:
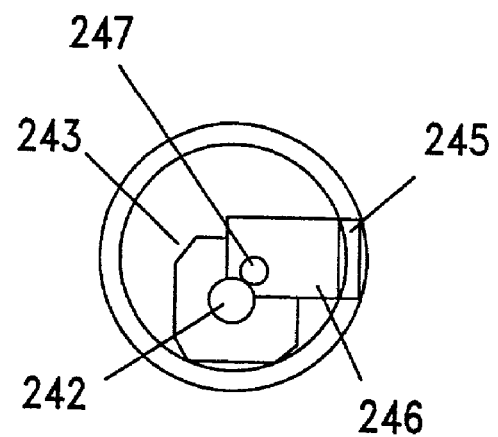
FIG. 33B is a cross-sectional view of the assembly of FIG. 33A looking from the distal end.

FIG. 33B is a cross-sectional view of the optical system of FIG. 33A showing how the various optical elements are arranged within the sheath of the endoscope.

Figure 34:
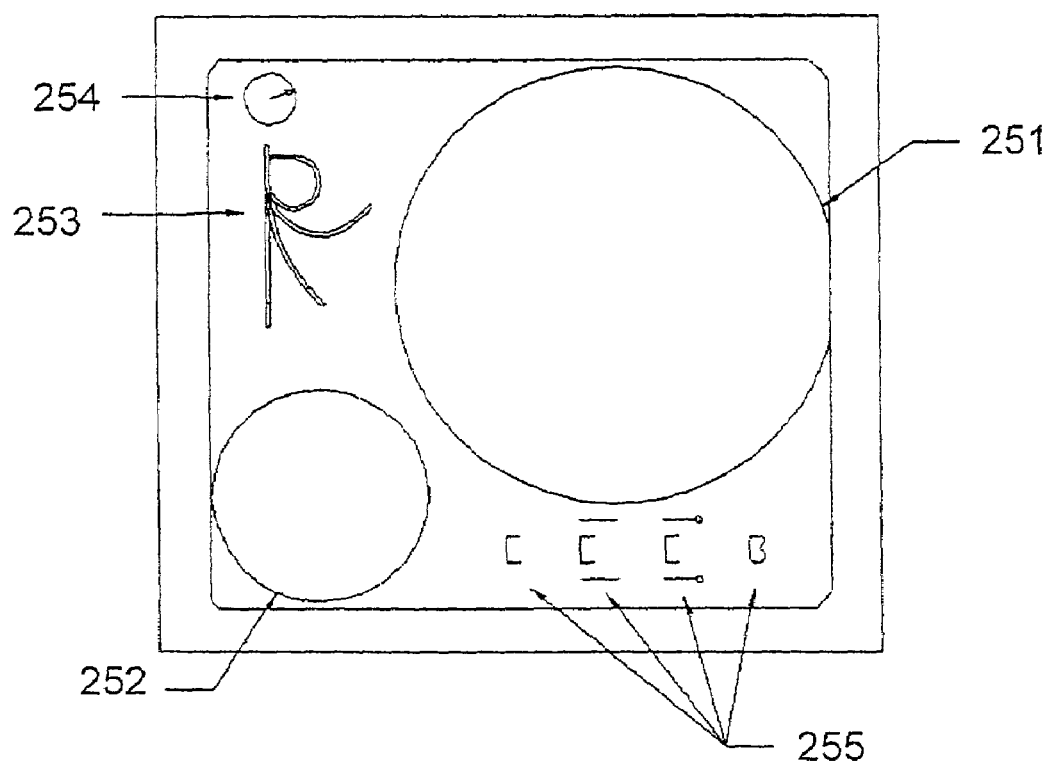
FIG. 34 shows a display layout for a preferred embodiment of the invention.

The display may incorporate status indicators relating to the various functions of the endoscope. For example in FIG. 34, 253 shows the status of the articulation of the distal end, 254 shows the rotation of the endoscope around the long axis, and 255 shows the stapler status.

Ultrasound Positioning Assembly

The navigation and the positioning of the distal tip in front of the cartridge requires two types of information:

1. Distance measurement (3–4 mm between the distal tip and the cartridge).
2. Alignment (defined here as the position and orientation of the object in some coordinate frame, i.e., three translations and three rotations; the desired tolerance is 0.5 mm).

Distance measurements are carried out most simply by various methods that are based on measurement the time of flight. These methods assume that the mean average velocity of an ultrasound wave propagating in a tissue has a constant value, for example 1500 m/s. By making this assumption, it is possible to estimate the distance by measuring the time of flight. There are basically two approaches that are used and they will be described with respect to the preferred embodiment of the endoscope described above.

In the first preferred embodiment of the invention employing a time of flight method, a single transducer is used for transmitting the ultrasound signal and receiving the echo that returns from a reflector. The distance is then calculated by measuring the time of a round trip, i.e. the time of a pulse that is emitted by the transducer (mounted, for example, on the cartridge), penetrates the tissue, is reflected back by the anvil, passes through the tissue again, and is received by the transducer. In this case the distance between the transducer and the reflector, d, is found from $$d = \frac{v_c \times t}{2}$$

Where, $v_c$ is the sound velocity (Approximately 1500 m/s) and the deviation by 2 denotes the fact that the pulse actually propagates twice the measured distance. In order to accomplish high resolutions, this method requires using very short pulses at high frequencies.

Another preferred embodiment of the invention, employing a time of flight method, makes use of two transducers. One is mounted on the distal tip and the other on the stapler cartridge. In this case the distance is calculated from, $$d = v_c \times t$$

The time of flight is measured by several different methods. The first and simplest preferred embodiment of the invention is based on energy detection. According to this method a clock is started simultaneously with the start of transmission and stopped when the energy input from the returning signal rises above a predefined threshold.

In another preferred embodiment of the invention, the time of flight is measured by transmitting a pulse and sampling the received signal in order to carry out a cross-correlation with a reference signal that is stored inside the computer memory. The cross-correlation method is more accurate than directly measuring the time of flight by the use of the threshold method. This is because the cross-correlation method compares the shapes of the received signal and is independent of the amplitude of the signals. The amplitude is constantly varying as a result of distortions caused by the electrical system and the medium through which the signal is propagated. Further, the cross-correlation method is based on integration of the signal, thus high-speed noise is filtered out and good results can be obtained even when the return signal is very weak.

The accuracy of the measurements in the second method can be improved by transmitting a random sequence of pulses, instead of a single pulse, and performing a correlation between the received sequence and a stored reference sequence. By modulating the random sequence with a digital modulation such as the well-known pulse shifted keyed (PSK) modulation, the reliability can be even further improved. Modulating a random sequence of pulses will help in detecting a weak signal that is immersed in noise. Further this type of correlation will reduce the measurement uncertainties that result from multipath and depth echoes.

In both methods, the velocity that is used is only an approximation and the resolution of the measurement is determined by the properties of the counter or the sampling rate clock that is employed.

The above methods of the time of flight measurements present some practical drawbacks. On the one hand, using only one transducer limits the minimal possible measuring distance to the length of the transmitted pulse; therefore, it is necessary to use very short pulses, which results in reduced accuracy. Also, the use of high frequencies will cause large attenuation of the propagating signal. On the other hand, use of the system that relies on two-transducers requires more space and increases the cost of the system.

As explained above, one of the most preferred types of positioning assemblies is based on ultrasound waves. This is because of the relative simplicity of use of ultrasound transducers, which are used in several medical uses, and the safety of use that can be attained under appropriate conditions. It should be appreciated that the desired precision of the positioning of the mechanical elements described above is not less than 0.5 mm, to ensure that the stapler and its anvil are correctly positioned in a facing position, and this precision is within the scope of ultrasound equipment.

A preferred embodiment of the invention, comprising an ultrasound positioning assembly, will now be described for the purpose of illustration.

Reference is made to FIG. 5, in which the two parts of the positioning assembly are indicated as numerals 62 and 62A. For the sake of this description we shall assume that the transmitter is element 62A, and the receiver is element 62. The transmitter transmits at any physiologically acceptable frequency. An illustrative example of suitable frequencies are those in the range 3–20 MHz. The beam of ultrasound energy should be focused. This can be done by adding an ultrasonic lens, or by using a phase array.

The receiver 62 is positioned on the other side of the tissue, as shown in FIG. 7. This receiver consists of a directional transducer, or an array of transducers, or a combination of both. The signal received at receiver 62 from transmitter 62A is analyzed, and its value is determined, as is also the distance between elements 61A and 61. A typical distance before stapling takes place is 0.5–1.5 cm. When scanning with transmitter 62A the space in front of receiver 62, a maximal signal is received when the two elements are at the maximal alignment position. When the maximum is attained, this signifies also that the stapler and its anvil are aligned, and stapling may take place. It should be noted that the anvil (or the stapler, depending on which of the two elements has been positioned on fixed portion "f" of FIG. 5) has been previously positioned so as to be at the correct location with respect to the tissue to be stapled. Thus, at this point the anvil, the stapler and the tissue between them are all correctly positioned. It should further be noted that the distance between the stapler and the anvil is also known, by measuring the time needed for the pulse to travel from one portion of the positioning assembly to the other.

The ultrasound assembly may be built in two alternative forms:

1. An assembly in which the antenna is common to both transmitter and receiver; and
2. An assembly in which each of the receiver and the transmitter has its own antenna (hydrophone for receiver and projector for transmitter).

Both assemblies are the same for the purposes of the invention, but each presents different technological advantages that will be discussed briefly below. In the second case lower energy of transmission is required, as compared with the first case. In the first case, on the other hand, an ultrasonic reflecting material, such as an ultrasonic mirror, can be positioned on the receiving side of the positioning assembly, so as to permit to reduce the energy of transmission.

The attenuation of the ultrasonic wave is directly dependent upon the frequency. An ultrasonic wave passing through a living tissue decays approximately according to the ration 1 dB cm$^{-1}$ MHz$^{-1}$ [*"Physical Principles of Medical Ultrasonics"*, Editor, C. R. Hill, Ellis Horwood Series in Applied Physics, John Wiley & Sons, NY 1986; G. S. Kino, *Acoustic waves: devices, imaging and analog signal processing*, Prentice-Hall Inc., New Jersey, 1987]. Taking into account the above, it is seen that when operating at a frequency above 10 MHz and distances above 50 mm, as may be found when operating according to the invention, a decay of 50–200 dB is expected.

Measurement of Distance

The following will illustrate a method for measuring the distance between the two elements 62 and 62A of the positioning assembly, according to the two above-mentioned preferred embodiments of the invention.

a. Using a separate transmitter and a receiver. When a separate transmitter and a receiver are used, the following two methods will exemplify the measurement of distance:

Counter Method

According to this method when transmission of the ultrasound pulse begins a counter is actuated, which stops its counting when the signal is received in the receiver. While, theoretically, any resolution of the time measurement is possible, very high resolutions require unnecessarily expensive and complicated equipment. For instance, in order to obtain an accuracy of distance measurement of 1μ, if the wave travels in the tissue with a mean speed of 1540 m/s, the frequency of the counter clock should be:

$$T_{clk}=1\text{Melanie}/1540 \text{ m/s}=1/6.5\times 10^{-10} \text{ s}=1.5 \text{ GHz}$$

However, much lower resolutions can be employed, of the order of 10–100μ, with a counter frequency of 15–150 MHz.

Correlation Method

The travel time of the wave can also be measured by sampling the signal received and correlating it to the transmitted signal. On the basis of this calculation it is possible (at the sampling resolution) to measure when the pulse reached the receiver. This is a more precise method, as compared with the counter method, and is therefore preferred for most devices.

b. Using a Transmitter-Receiver. In this case a pulse is transmitted from the transmitter-receiver positioned on either side of the device. For this example we will assume that the transmitter-receiver is positioned on the stomach side (portion "b" of FIG. 5), and at the other side (part "f" of FIG. 5) an "ultrasonic mirror" plays the role of portion 62 of the positioning assembly. At the same time the pulse is transmitted a counter is actuated, which is stopped when the reflected signal is received back by the transmitter-receiver. The distance is calculated as the time measured by the counter, divided by 2 and multiplied by the speed of travel of the wave in the tissue.

This mode has the disadvantage that since the same hardware is used for transmitting and receiving, as long as the transmission of the pulse is not completed no receiving is possible. Accordingly, all reflections reaching the receiver during transmission are not used. Thus, the minimal measurable distance is determined by half the transmission time.

Figure 35:
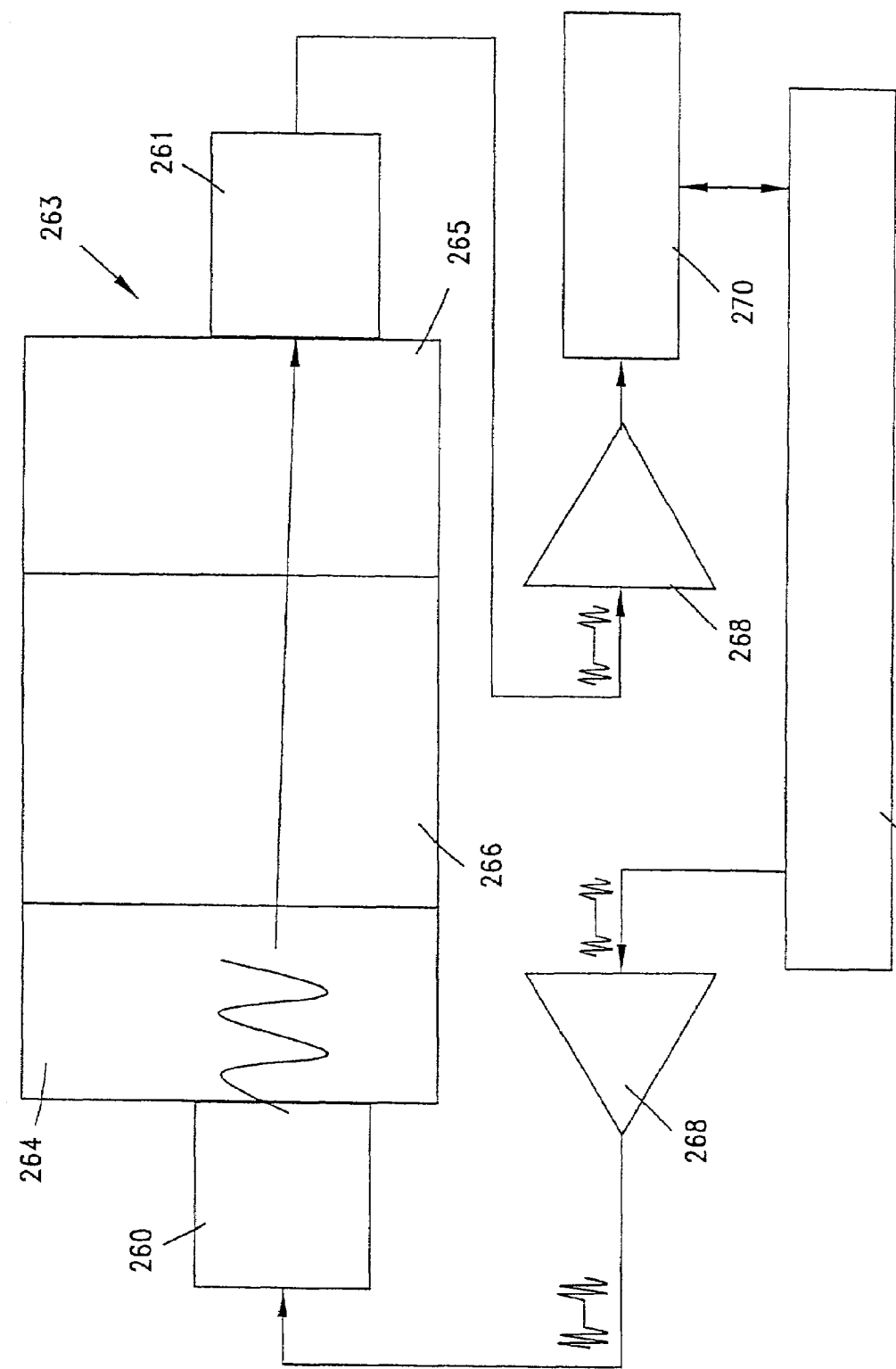
FIG. 35 is a block diagram of an ultrasonic positioning assembly, according to a preferred embodiment of the invention.

FIG. 35 is a block diagram of an ultrasonic positioning assembly, according to a preferred embodiment of the invention. Existing ultrasound equipment operates either in the so-called "C-MODE" (C-scan), or "A-MODE" (A-scan) (see *"Acoustic Waves"*, Gordon S. Kino, Prentice-Hall, 1987). In the example of FIG. 35 a C-MODE ultrasound is illustrated, although the same principles can be applied, mutatis mutandis, to A-MODE.

A transmitter transducer (or array of them) 260, and a receiver transducer (or an array of them) 261, are separated by tissue 263, consisting of three separate layers: the boundary 264 of the esophagus, the boundary 265 of the fundus, and the fat tissue 266 between them. The timing and control system 267 generates pulses of a frequency of, e.g., 10 MHz, with a pulse repetition frequency (PRF) of 100 Hz and a pulse width of 8 μsec. The pulses are amplified by the amplifier 268 and reach the transducer 260, where the electrical signal is transformed into an ultrasonic wave. The average size of a suitable ultrasonic transducer is 2–10 mm. Directional transducers are preferred.

The ultrasonic wave passes through tissue 263 and reaches the receiver 261, that translates it into an electric signal which is amplified in amplifier 269. The amplified signal is fed to a signal analysis circuit 270 that performs the following functions:

a. It determines whether the transducers are aligned transversally. This can be achieved by scanning transversally, either manually or automatically, using a servo motor, and determining the maximum in the signal, or in an array by using phase difference.
b. It measures the distance between the two transducers, as previously described, or in any other suitable manner.

The operation of the various elements of FIG. 35 is well known to the skilled person, and is therefore not described herein in detail, for the sake of brevity.

Figure 36:
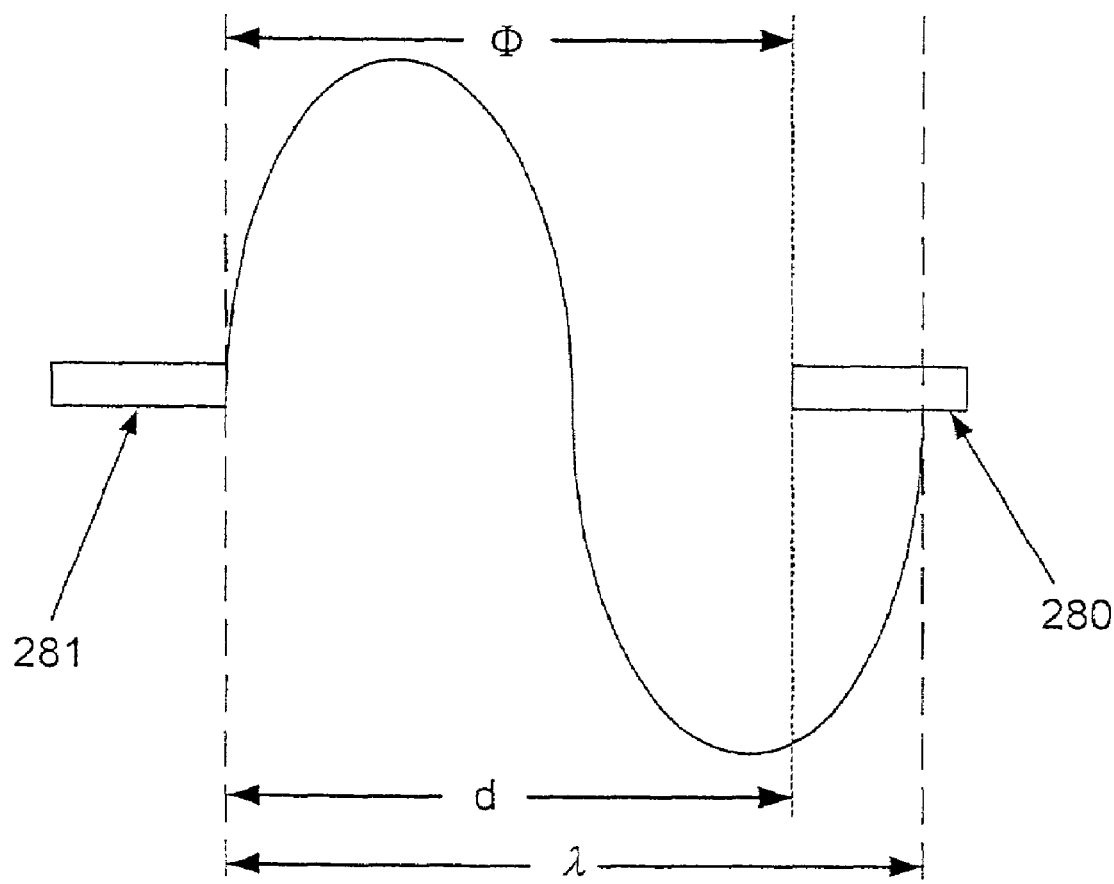
FIG. 36 schematically illustrates the spatial phase difference of measuring distance.

Another method for measuring the required distances is employed to overcome some of the above-mentioned difficulties of the time of flight measurements. In this preferred embodiment of the invention, the spatial phase difference between the transmitted and the received wave is measured. FIG. 36 illustrates the method. If the measured phase angle is Φ and the wave length of the ultrasound signal is λ, and the distance between the transmitting transducer (numeral 281) and the receiver (numeral 280) is d, then:

$$d = \frac{\lambda \cdot \Phi}{360}$$

As can be seen from FIG. 36, A(d)=A₀ sin(Φ), where A(d) is the measured signal and A₀ is a known value determined from a previous calibration measurement. Thus Φ can be calculated from the arcsine function and the distance is therefore determined from $$d = \frac{\lambda \cdot \arcsin\left(\frac{A(d)}{A_0}\right)}{360}$$

Since the arcsine function leads to two possible solutions for the distance, it is necessary to make at least two measurements from two adjacent spatial points in order to determine the direction of the slope and therefore the correct solution of the equation.

This method is restricted to low frequencies only, because the measuring distance is limited to only one wavelength (ambiguity will occur when the distance is greater than a single wavelength). In order to measure distance of 4–20 mm, for example, dictates working at frequencies in the range of 75–375 kHz.

The advantages of this method are that the precision is rather high in comparison with the time of flight method (since it is possible to extrapolate the distance from any measurement) and using low frequencies decreases the attenuation of the propagating signal. However, this method also assumes that all the tissue in the propagating path is the same. In addition, it is necessary to use at least two transducers; therefore the cost and space requirements are increased.

In another preferred embodiment of the invention, the time of flight and spatial phase difference methods are both used by commencing measurement from a relatively far distance by using the former method, and then when the distance is equal to or less than one wavelength, to begin measuring the phase difference. In order to use this approach for the purposes of the present invention, it is necessary to use an efficient transducer with a short diameter, such as 1–2 mm, that is capable of supporting two different frequencies, e.g., 150 kHz and 2 Mhz.

The complexity of manufacturing a transducer with two different frequencies that are very far one from the other is overcome by measuring the acoustical transmission at two wavelengths, as follows: The received signal, $S_1$, derived from the acoustic signal of the transducer aperture is given by:

$$S_1 = R_1 \cdot A \cdot I_{t1} = R_1 \cdot A \cdot I_{01} \cdot e^{-a_1 \cdot z}$$

where, index 1 refers to wavelength 1, R is the transducer responsivity, A is area of the "illuminated" aperture that is seen by the transducer aperture, $I_t$ is the acoustic intensity that has traversed the medium, $I_0$ is the intensity $$Z = \frac{1}{a_1 - a_2} \ln\left(\frac{R_1}{R_2}\right) \times \frac{I_{01}}{I_{02}} \bigg/ \frac{S_1}{S_2}$$

that is radiated by the transmitting transducer, a is the absorption parameter, and Z is the distance that the beam travels through the absorbing medium. The second wavelength yields a similar equation, with index 2 replacing the index 1. The distance Z can be extracted from the quotient $S_1/S_2$.

In the last expression, the term ($I_{01}/I_{02}$) is unknown, but could be recovered from a calibration measurement. The calibration measurement is a replica of the actual measurement; however the medium between the apertures has known absorption e.g., water. Denoting the signals from the absorption-free medium by $S_1'$ and $S_2'$ $$\frac{S_1'}{S_2'} = \frac{R_1}{R_2} \cdot \frac{I_{01}}{I_{02}}$$

hence, $$Z = \frac{1}{a_1 - a_2} \ln\left[\frac{S_1'}{S_2'} \bigg/ \frac{S_1}{S_2}\right].$$

As opposed to the phase measurement method, it is necessary to use only one transducer for both transmitting and receiving. In addition, although it is necessary to use a dual frequency transducer in both methods, in the last method described above, the difference between frequencies used does not have to be as great as in the phase measurement, making it easier and less costly to produce the transducer.

As in the case of the distance measurements, several methods can be proposed to enable the alignment of the endoscope. The simplest embodiment of the invention uses imaging by phase array to accomplish the distance measurements and alignment. Many small transducers comprise the array that is used for imaging as in the prior art. A conventional catheter transducer can be mounted on the distal tip and used to image the cartridge to carry out the alignment and distance measurements. Although this method is in principle based on existing techniques and easy to implement, the size of the transducer and accompanying electrical wires, as well as the cost, prevent this from being an embodiment of the invention that is preferred for most applications.

Figure 37:
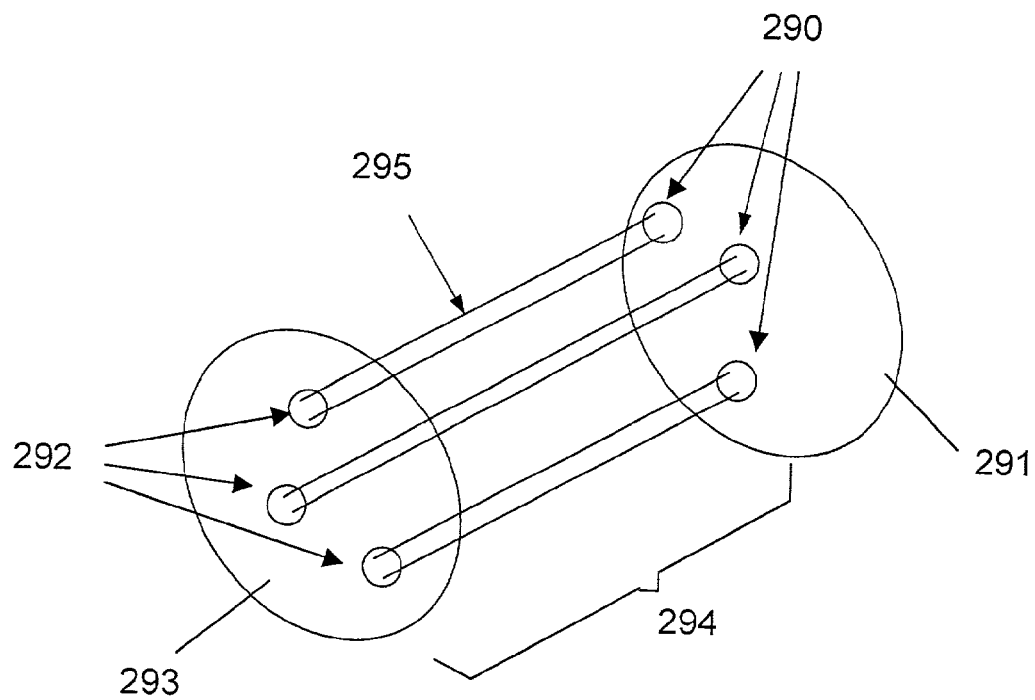
FIG. 37 schematically illustrates an alignment method based on intensity methods.

In another preferred embodiment of the invention, use is made of intensity measurements. This method is shown in FIG. 37 and requires the use of at least three transducers (designated by numeral 290) on the distal tip 291 and three (numeral 292) on the cartridge 293. To reach alignment, it is necessary to position all the three transducers on the distal tip in front of the three transducers on the cartridge. At first the distal tip is located somewhere in front of the anvil. The distal tip scans a spatial angle of 180° or less and the angle where the maximum amplitude was measured is stored. The distal tip is displaced according to the stored angle and the scanning recommences. This procedure is repeated until the maximum amplitude is measured, at each receiver when its mating transmitter-is active at 0°.

There are several possible situations that could arise in the alignment procedure that must be taken into account when developing the methods that are used to process information on the position of the distal tip in front of the cartridge and then displace the distal tip in the direction of closer alignment according to this information. As an example, the distal tip is located above or below the cartridge, thus transverse scanning might not detect anything, but the up-down scanning will detect a signal (actually it might detect two signals, from the lower and the upper receiving transducers). Another example is when the upper transducer of the distal tip is located in front of (or close to) the two lower transducers of the cartridge. In this case transverse scanning will detect two positions and up-down scanning might or might not detect any signal.

In order to achieve maximum precision, it is necessary that the transmitting beams be as thin as possible. There are two ways of satisfying this requirement. A first embodiment, illustrated in FIG. 37, relies on the fact that in the Fresnel zone (designated by numeral 294) the beam (designated by numeral 295) is somewhat collimated and thin. Thus to maximize precision, the method is employed at distances less than the Fresnel distance=$r^2/\lambda$, where r is the radius of the transducer, $\lambda=v/f$ is the wavelength of the transmitted beam, f is the natural resonance of the transducer, and v is the speed of sound in the medium.

Figure 38:
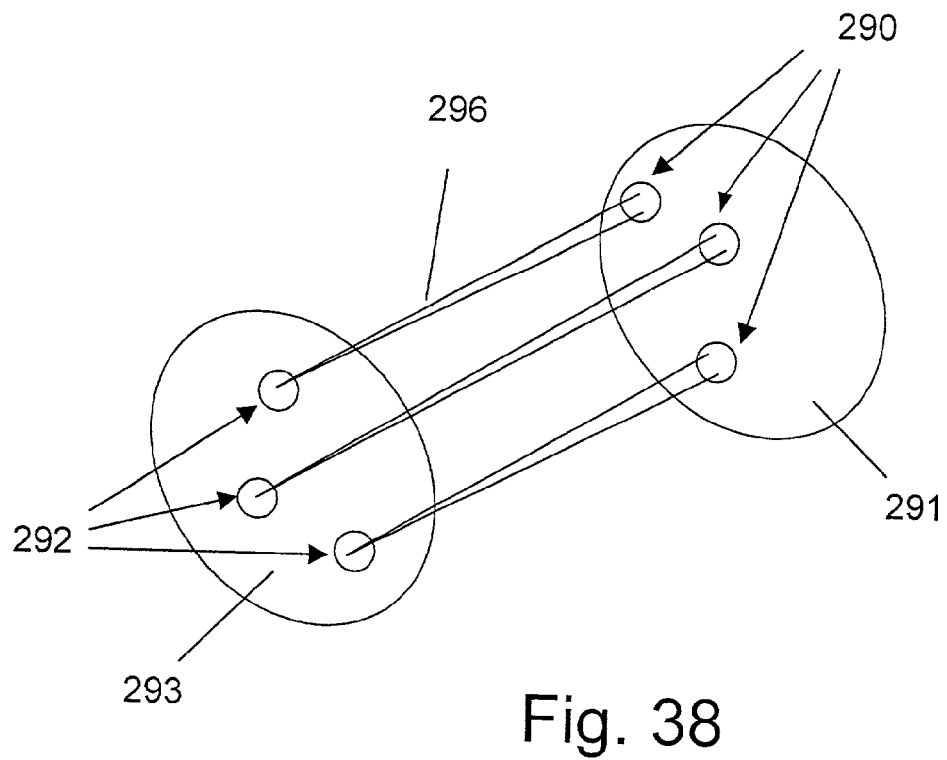
FIG. 38 schematically illustrates another alignment method based on intensity methods.

The second embodiment is shown in FIG. 38. Here, as in FIG. 37, the transducers are designated by numerals 290 and 292, the distal tip by 291, and the staple cartridge by 293. In this embodiment, the set of transducers that act as the transmitters, for example those on the distal tip, are focused transducers. This results in focused beams (numeral 296). For better precision, it is also possible to use focused transducers as receivers.

The desired resolution dictates that in both embodiments, optimal precision will be obtained at high frequencies (e.g., 10 MHz and above for a 1 mm radius transducer). It should be noted that in the Fresnel zone the transmitted intensities contain irregularities therefore, although the distal tip is moving towards the anvil there are points where the intensity will decline instead of increasing. This difficulty must be taken into account in designing the process referred to above.

Although in principle the above embodiments have the advantage of simplicity, the scanning procedure can consume a lot of time and also requires that the endoscope have scanning capabilities for the distal tip. In addition, the large number of transducers and the electrical wires that connect them require a large volume of a very limited amount of space and also increase the cost of the system.

If the transmitting and receiving transducers are located symmetrically, then the system will appear to be aligned even if a rotation of 120° in either direction takes place. This potential error can be avoided by, for example, using an asymmetric arrangement of the transducers or by causing each transmitter to generate a unique sequence of pulses.

Figure 39B:
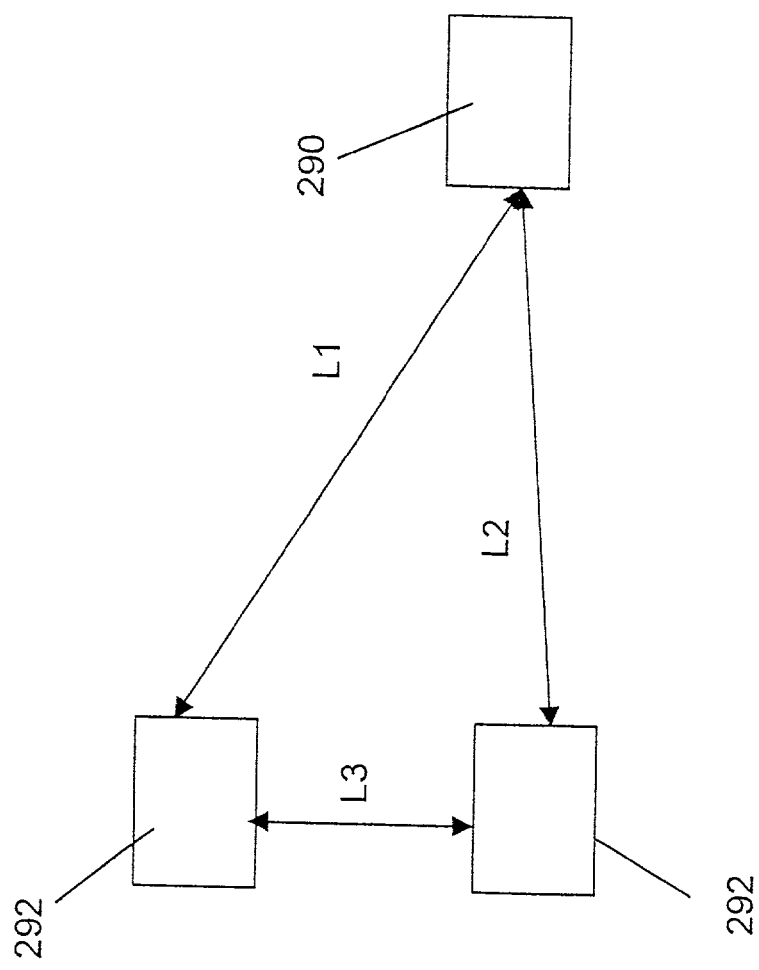
FIGS. 39A and 39B schematically illustrate a triangulation method of alignment.
Figure 39A:
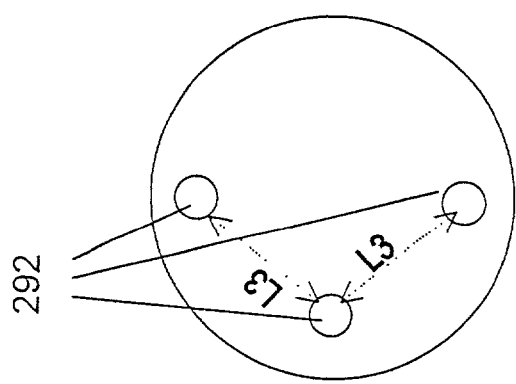

Embodiments of the invention, which improve on the above-described embodiments primarily by reducing the number of transducers required, are based on the principle of triangulation. The basic configuration employed comprises one transmitter and three receivers (or three transmitters and one receiver). FIG. 39A shows the array of three receivers (designated by numeral 292) located on, for example the stapler cartridge. The distance between every two receivers $L_3$ is known, since it is precisely defined at the production stage. Every two receivers and the transmitter create a triangle, thus alignment is achieved when the three triangles have equal sides, as determined by the desired distance between cartridge and tip. The distal tip is displaced until all the measured distances are equal. The displacement direction is evaluated from the differences between the three measured distances. It is also possible to construct the triangle asymmetrically such that for alignment detection the triangle will have unequal sides.

Limiting the number of degrees of freedom of the endoscope will reduce the amount of transducers, e.g., with a two-way endoscope, only one transmitter and two receivers will be used. The situation for a two-way endoscope is shown in FIG. 39B. In FIG. 39B, numeral 292 designates a transducer used to receive the signal transmitted by the transducer designated 290. As explained above, transducer 290 is moved until $L_1=L_2$, at which point the two parts of the stapler are aligned, and the distance is determined by one of the methods described previously.

The embodiments employing the triangulation method are improved upon by using transducers built from an array of elements instead of single element transducers. In this case multiple triangles are created and the measurements are therefore more precise.

Another difficulty that arises in using triangulation methods is that the beam in the Fresnel zone is sometimes very thin thus, it is impossible to illuminate two adjacent receiving transducers with only one transmitting transducer and vice versa. To overcome this difficulty a diverging transducer is used or an aperture is placed before the transmitting transducer causing the beam to be divergent and therefore assuring that the signals from the transmitter will reach the receivers. The use of diverging beams results in weaker signals and reduced alignment accuracy.

In another preferred embodiment of the invention, some of the difficulties encountered in the previously described embodiments are overcome by a special arrangement of the transducers employed in the triangulation measurements.

Figure 40:
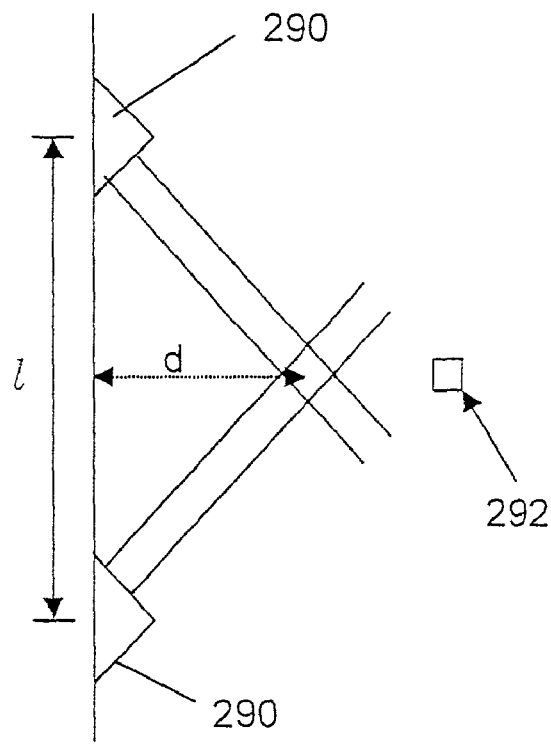
FIG. 40 schematically shows a triangular construction for use in an alignment method.

The following description is given for a two-way endoscope, for the sake of simplicity, but can easily be expanded to a four-way endoscope by adding another triangulation construction. The triangulation construction shown schematically in FIG. 40 comprises two transmitters 290, with a distance L between them, and one receiver 292. The transmitters are mounted on the stapler cartridge at such an angle that the two transmitting beams meet at a distance "d" from the axis that is perpendicular to the cartridge. The distal tip scans the cavity until it locates (by intensity measurement) one arbitrary beam. Then the distal tip follows this beam by gentle scanning until it reaches the point where the received amplitudes from the two transmitters are equal. The transmitters transmit sequentially with a time interval. This method is limited to using thin beams and thus works in the range of a couple of MHz to insure that the meeting point will be in the Fresnel zone. Instead of working in the Fresnel zone it is possible to use focused transducers with focal length of the desired distance.

Figure 41:
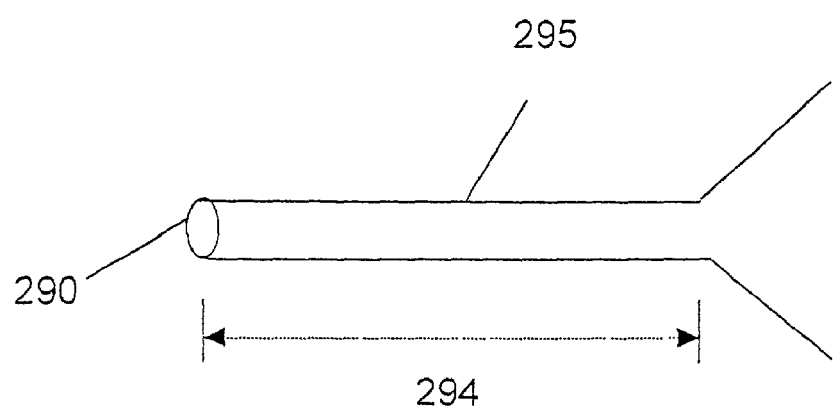
FIG. 41 schematically illustrates the shape of an ultrasonic beam.

The fact that after the Fresnel zone or after the focal point the beams are divergent is useful in initially locating one of them from a distance where the cross section of the beam is larger than it is when close to alignment. FIG. 41 schematically shows the behavior of the beam 295 transmitted by the transducer 290. Within the Fresnel zone 294, the beam is essentially collimated; while beyond the zone, the beam diverges.

The following specific example illustrates possible dimensions used for building the triangle construction for the above-considered endoscope containing a stapler:

The distance between the distal tip containing the anvil and the stapler cartridge=d=4 mm.
The distance between the transmitting transducers=l=10 mm.
The radius of the transducer=a=1 mm.
Using the requirement that the Fresnel distance (=$a^2/\lambda$ for d>>a) should be longer or equal to d leads to the result that $\lambda$=0.25 mm, i.e. the frequency F=6.16 MHz. At 3 dB, the half beam angle $\theta$ is determined from, sin $\theta$=0.51·$\lambda$/2a, yielding $\theta$=3.65°. The angle is measured with respect to the perpendicular to the transducer surface, therefore the total angle 7.32°.

It should again be mentioned that, within the Fresnel zone, the intensity of the transmitted beam is described by a Bessel function and is therefore not uniform. This fact must be taken into account when using embodiments of the invention that are dependent on measurements taken within the Fresnel zone.

As discussed above, in an alternate embodiment focused transducers with a 4 mm focal point are used. In this case it is possible to carry out the measurements at higher frequencies.

The major advantage of this embodiment is that it omits the need for distance measurement, because the distance is a priori known from the special construction.

A further embodiment of the invention that reduces the complexity of building the precise triangulation construction and omits the mechanical scanning employs a phase array. This embodiment comprises a transducer mounted on the distal tip and two or more transducers mounted on the cartridge (or vice versa). The transducer on the distal tip is built from an array of elements (the ones on the cartridge can be built from one element or an array of elements). The array produces a beam that can be steered by electronic means. The steered beam scans the cavity until it is received by one of the transducers. The angle of the steered beam suggests the displacement direction of the distal tip. The alignment is achieved when the measured angles are equal (or can be pre-manufactured with known non-equal angles) to both transducers. In this embodiment the distance can be measured by time of flight or triangulation calculation. Another way of implementation is imitation of the triangulation construction described above with reference to FIG. 40. In this case mounting the transducers at an angle to the surface of the cartridge is not necessary since the steerable beam from the array replaces this feature.

Figure 42:
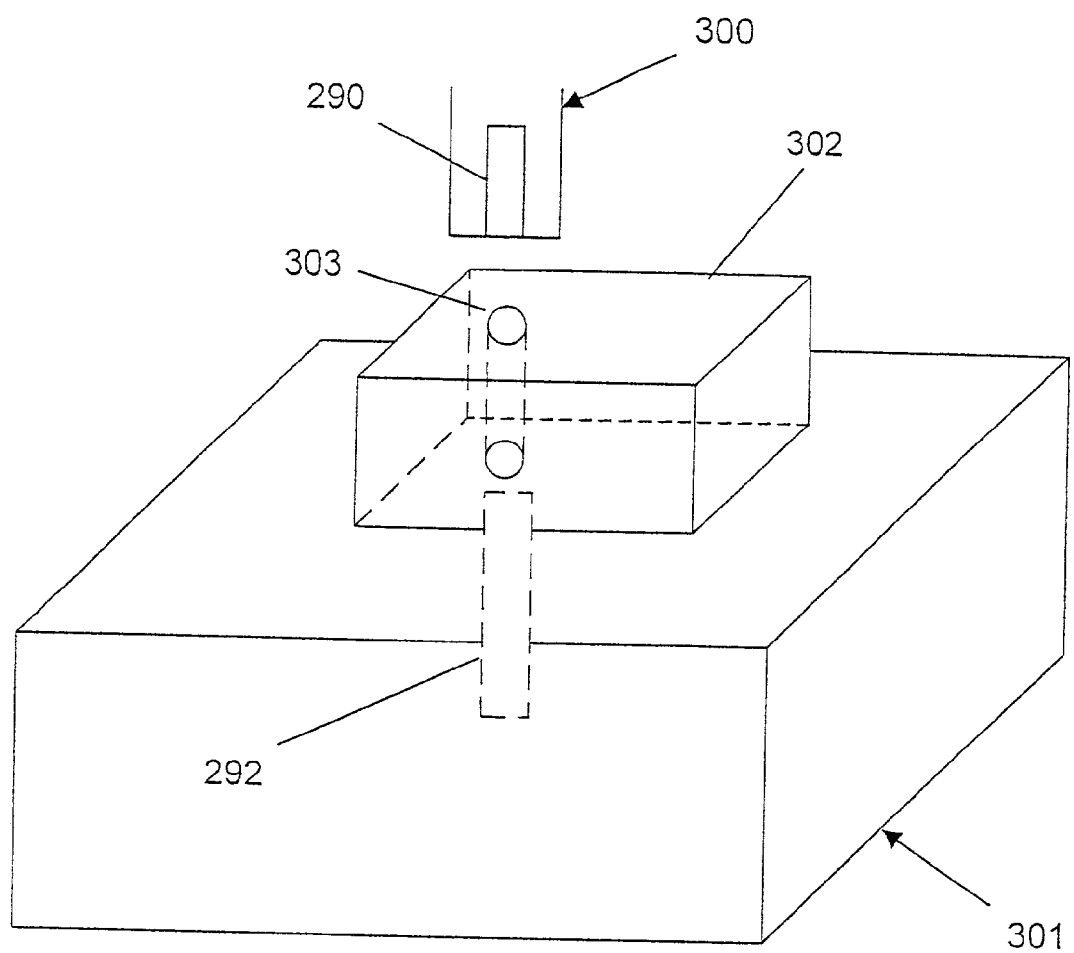
FIG. 42 schematically illustrates the wave-guide positioning method.

An alignment method based on intensity measurements, which is a greatly simplified version of the first alignment method described above, is illustrated schematically in FIG. 42. This embodiment employs two transducers. The transducer 290 on the distal tip 300 is the transmitter. The receiving transducer 292 is mounted on the cartridge holder 301 below the movable staple cartridge 302. A channel 303, which is created throughout the entire height of the cartridge, guides the signal to the receiver. The channel has a small diameter of about 0.5–1 mm. This configuration detects alignment only when the distal tip is positioned in exactly the right position in front of the cartridge.

The preferred embodiments of the invention are based on systems that comprise one transducer and either a single reflector or a plurality of reflectors. The transducer is used both for transmitting and receiving. The reflector is built from a special construction that reflects back a pattern that can be translated into the position and orientation of the transmitter relative to the reflector. The transducer can be mounted on the distal tip or on the staple cartridge or vice versa. Mounting the reflector on the cartridge is usually preferred, since this eliminates the electrical wire connections for the transducer that would interfere with indexing of the cartridge. The following are representative, but not limitative, examples of the many possible configurations that can be derived from this model.

Figure 43A:
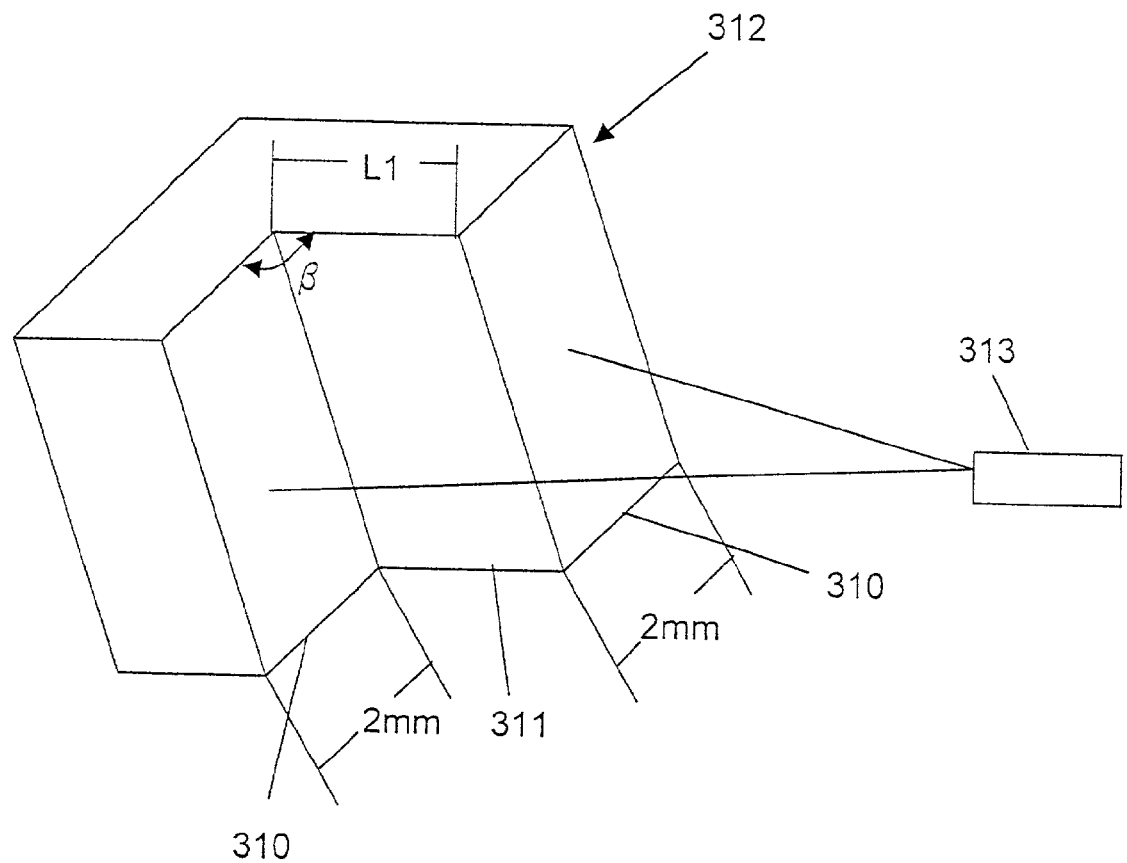
FIG. 43A schematically illustrates a one-step reflector.
Figure 43B:
FIG. 43B schematically illustrates the signal reflected from the reflector of FIG. 43A.

The basic configuration (including representative dimensions) of these embodiments is shown in FIG. 43A. Two parallel reflecting planes (designated by numeral 310) are separated by a distance $L_1$ by a planar surface 311 that intersects the reflecting surfaces at an angle $\beta$ such that $\beta \leq 90°$. The resulting step construction (generally indicated by numeral 312) is irradiated by the beam from the transmitting transducer 313. If the transmitted beam impinges on both layers, then the reflected signal comprises two consecutive echoes, one from the front layer and the second from the rear layer as shown schematically in FIG. 43B.

Figure 43C:
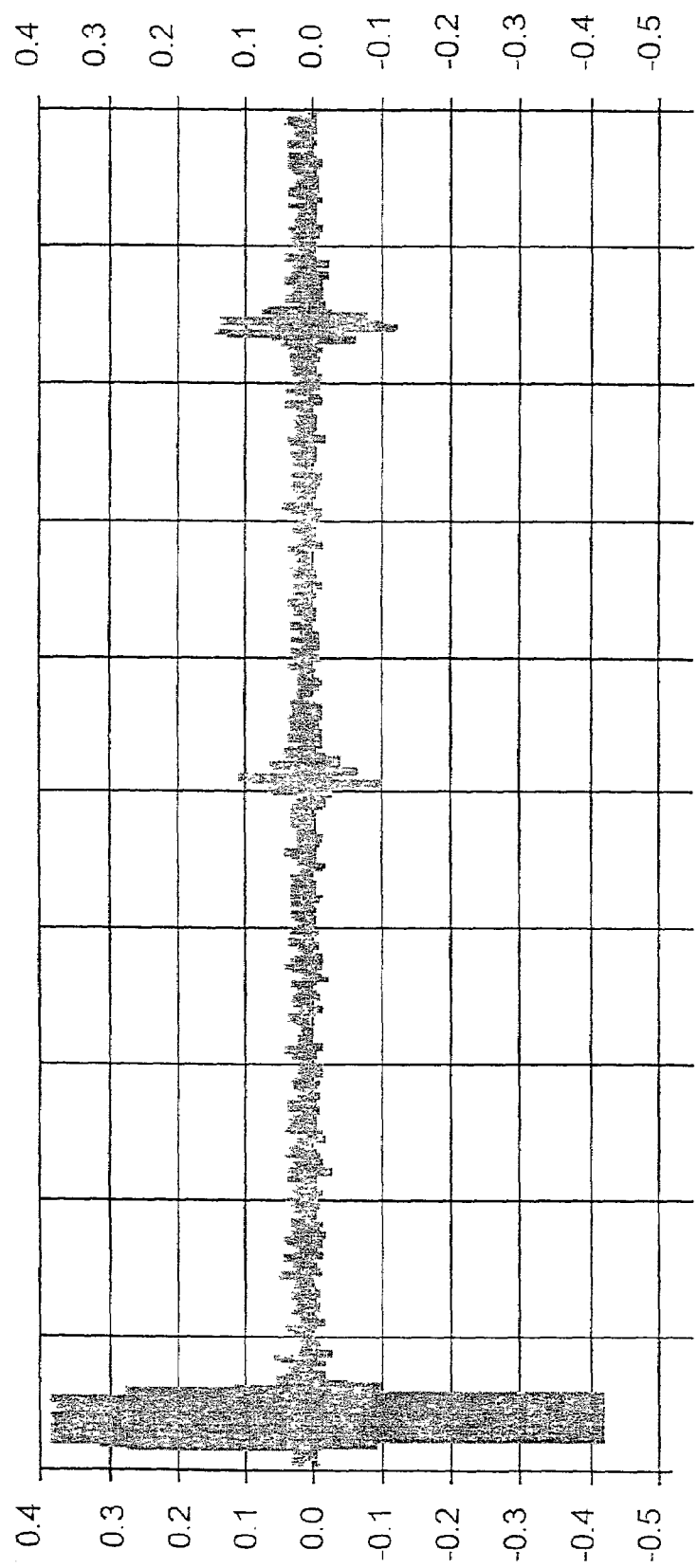
FIG. 43C is a reproduction of an oscilloscope screen showing the reflections from a reflector of the type shown in FIG. 43A.

FIG. 43C is a reproduction of a photograph of an oscilloscope screen showing the results of an experiment carried out using a one-step reflector of the type shown in FIG. 43A. The large pulse on the left of the screen is the transmission pulse and the two smaller pulses are the echoes from the reflector. On the horizontal scale, representing time, each division is 1.2 μsec. In this example, the reflector is positioned such that the nearest reflecting surface is 4.3 mm from the emitting transducer and the depth of the step $L_1$=3 mm. The measured time between the pulses is 4.08 μsec, thus the measured depth of the step is found from $$L_1 = d = \frac{v_c \times t}{2} = \frac{1500 \text{ m/s} \times 4.08 \text{ μsec}}{2} = 3.08 \text{ mm}$$

The agreement between the measurement and the actual depth is determined by the measuring system performance.

Methods of improving the agreement will be discussed below in conjunction with the descriptions of the software and the electrical module.

When the transducer is aligned with the reflector then the measured distance between the layers must be $L_1$ and the measured pulses must have an amplitude relation that is relative to the depth of the step. This relation can be evaluated from the well-known attenuation relation of an ultrasound wave propagating in soft tissue (G. S. Kino, Acoustic waves: devices, imaging and analog signal processing. New Jersey: Prentice-Hall Inc., 1987.)

$$\frac{A_{rear}}{A_{front}} = -2 \times 0.8 \text{ dBcm}^{-1}\text{MHz}^{-1},$$

Where $A_{rear}$ is the echo amplitude from the rear layer and $A_{front}$ is the echo from the front layer. Other influences on the signal amplitude are the step cross-section and the spatial angle between the distal tip and the reflector face. For example, consider the two-echoes reflector described with relation to FIG. 43C that reflects back a signal emitted from a transducer with a natural frequency of 10 MHz (a 100 nsec pulse). The relation $A_{rear}/A_{front}$ yields approximately 4.8 dB or $A_{rear}=0.707A_{front}$. Referring to FIG. 43C, the front echo amplitude is smaller than the rear echo suggesting that alignment has not been achieved. Furthermore if for instance the path of the transducer on the distal tip dictates that it should irradiate the front reflective layer first and then, after, the rear layer then it is obvious that the distal tip should be moved back in order to achieve alignment.

The detection procedure that is used to implement the alignment is based on the following criteria:
1. Alignment is accomplished only when the echoes are received at a certain time difference and with a certain amplitude relation (within predefined, reasonable tolerances).
2. The reflector and the transducer are not aligned whenever:
   a. no signal is received, or
   b. only one echo is received, or
   c. the amplitude relation is not satisfied, or
   d. the time between the consecutive echoes is different (i.e. a different distance is measured).

This procedure will be discussed hereafter in more detail.

Figure 44A:
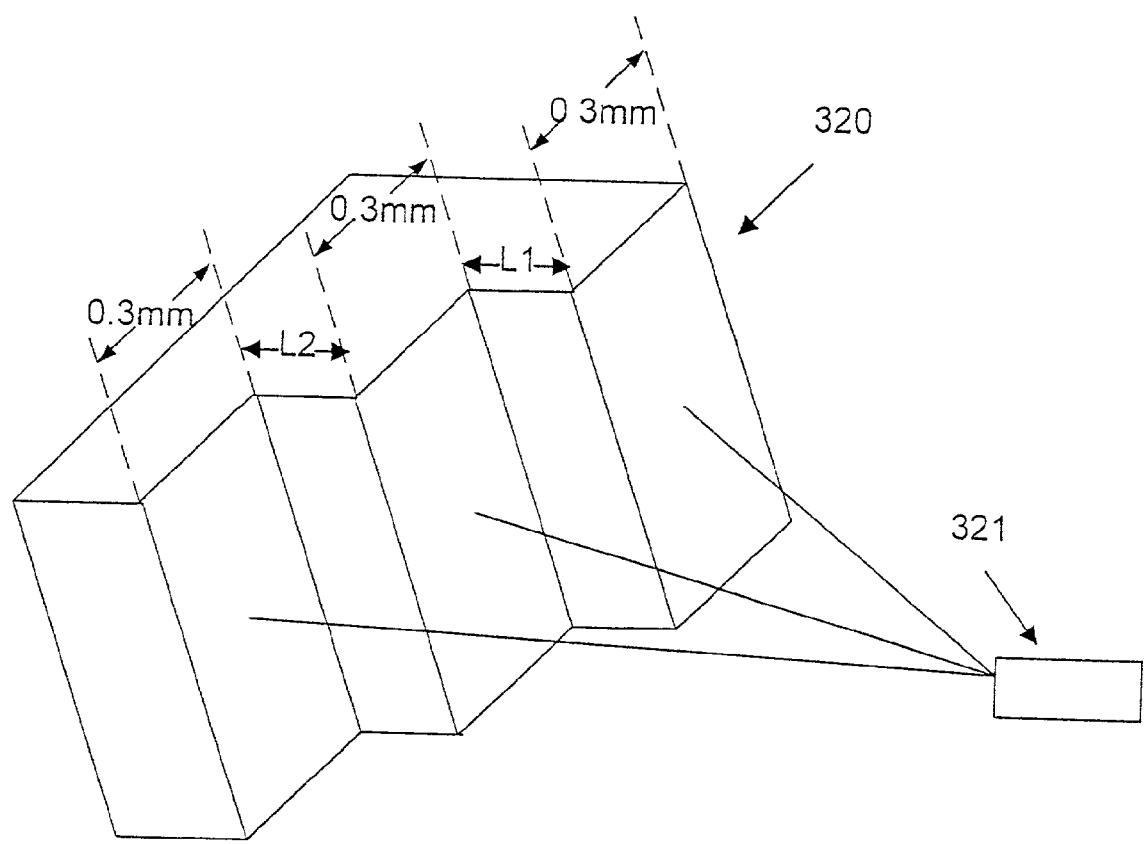
FIG. 44A schematically illustrates a two-step reflector.
Figure 44B:
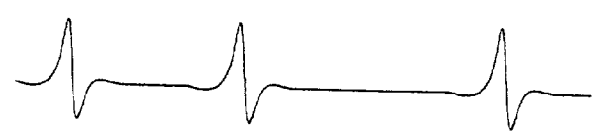
FIG. 44B schematically illustrates the signal reflected from the reflector of FIG. 44A.
Figure 45A:
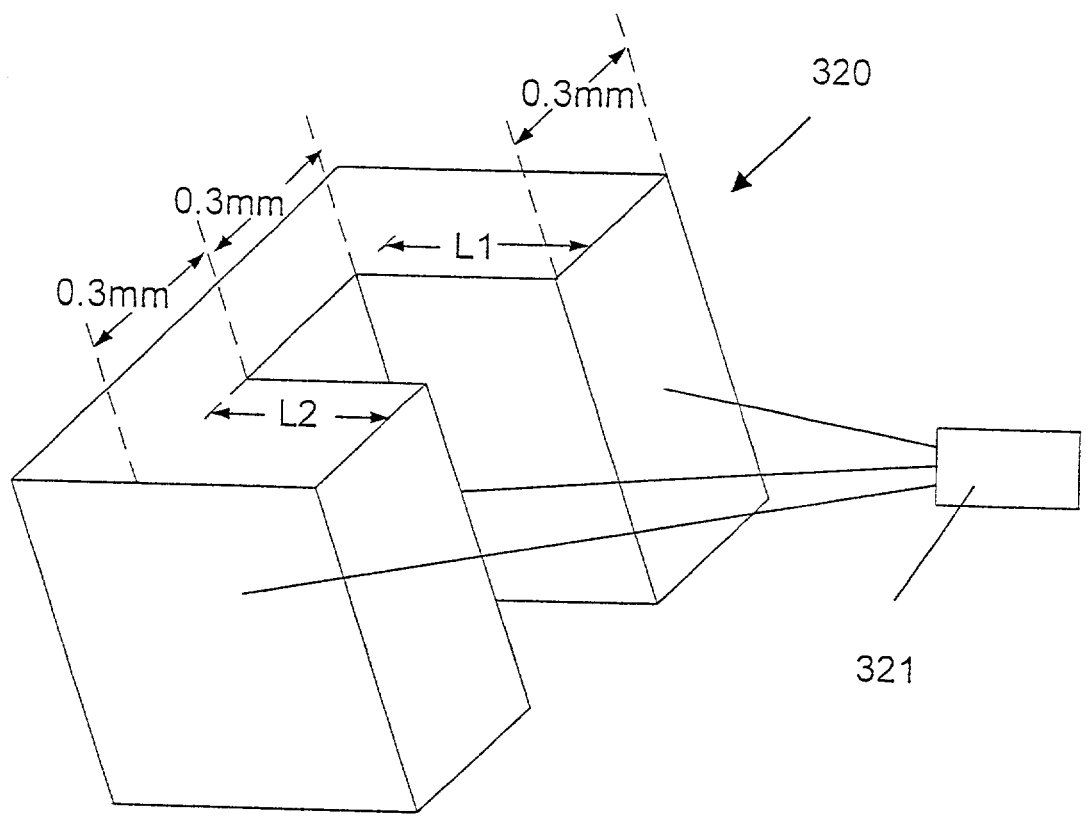
FIG. 45A schematically illustrates another two-step reflector.
Figure 45B:
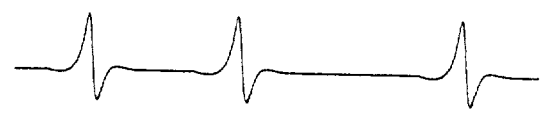
FIG. 45B schematically illustrates the signal reflected from the reflector of FIG. 45A.
Figure 46A:
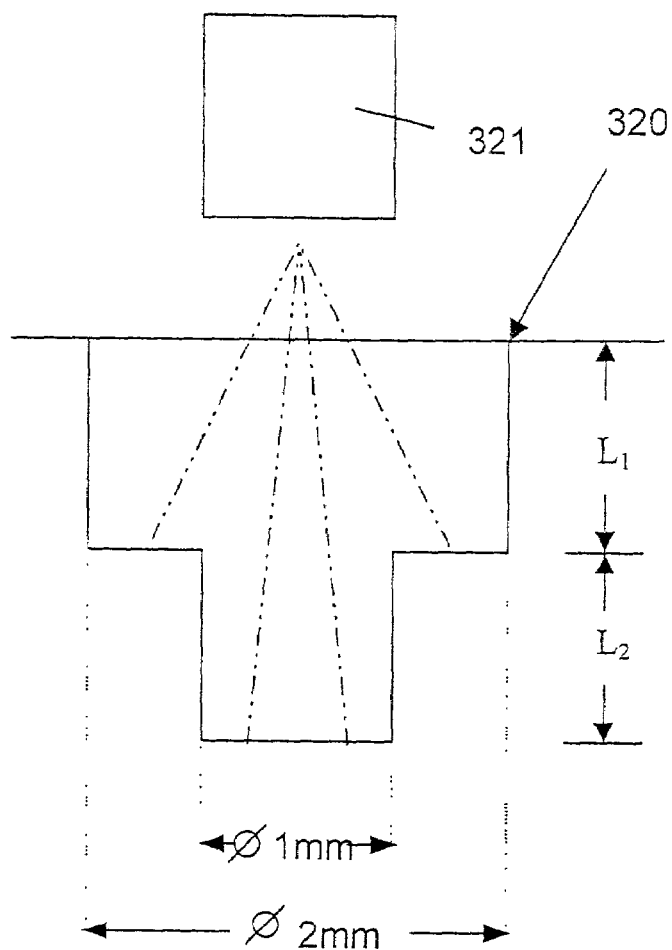
FIG. 46A schematically illustrates a cylindrical reflector.
Figure 46B:
FIG. 46B schematically illustrates the signal reflected from the reflector of FIG. 46A.

In a preferred embodiment of the invention, the reflector is constructed with two or more steps. FIGS. 44A, 45A, and 46A illustrate a few of the many possible two-step (three echoes) constructions that can be used. In these figures, the reflector is generally designated by numeral 320, the transducer by 321, $L_1$ and $L_2$ are the heights of the two-steps, and typical dimensions are shown. In these cases the reflected signal comprises three echoes with certain time differences and amplitude relations between them that correspond to $L_1$ and $L_2$ respectively. The reflected signals that correspond to 44A, 45A, and 46A respectively are schematically shown in FIGS. 44B, 45B, and 46B.

Using different values of $L_1$ and $L_2$ assists in completing the alignment. If for instance, only two of the three echoes are received, it is possible to determine on which pair of steps the beam of the transducer is falling by the distance between the echoes. This information is then used to determine the position of the distal tip relative to the reflector and to steer it closer to alignment.

FIG. 46A shows a two-step reflector made from a cylinder with two bores drilled inside. One bore is 2 mm diameter and in the center of the 2 mm bore another 1 mm bore is drilled. This construction when almost, but not exactly, aligned will reflect back three consecutive pulses; one from the face of the reflector one from the peripheral area of the 2 mm bore and the third pulse is from the bottom of the 1 mm bore. There will be two-echoes when the parts are exactly aligned or if the displacement is such that the bottom of the 1 mm bore is not irradiated by the transmitted beam. To distinguish between the possibilities when only two-echoes are measured, the reflector is constructed with steps of unequal depth.

Figure 46C:
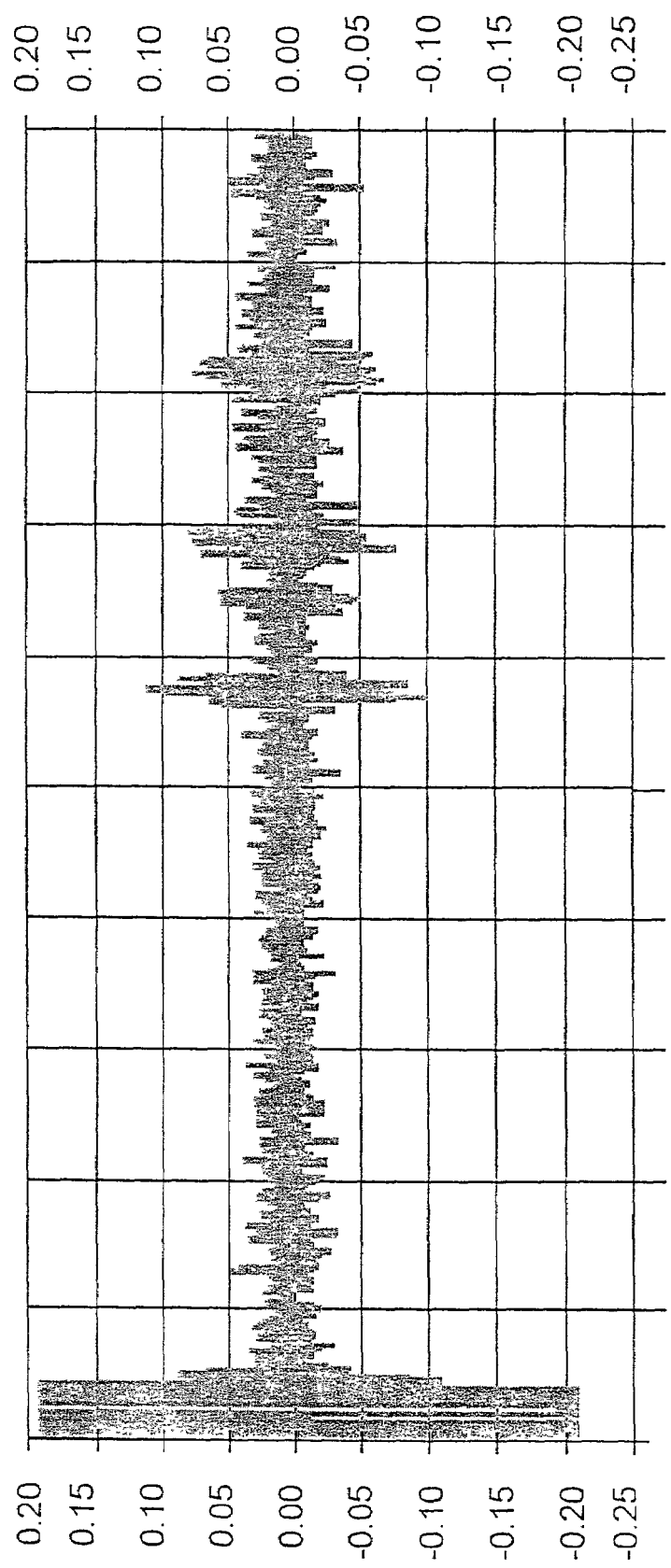
FIG. 46C is a reproduction of a photograph of an oscilloscope screen showing the reflections from a reflector of the type shown in FIG. 46A.

FIG. 46C is a reproduction of a photograph of an oscilloscope screen showing the results of an experiment carried out using a two-step cylindrical reflector of the type shown in FIG. 46A. The left signal is the transmitting pulse; the three echoes on the right are from three different layers. The time scale is 1.1 µsec per division. The depths between the layers are $L_1=L_2=1$ mm. The reflector is mounted 4.7 mm from the reflector. The measured time between the consecutive echoes is 1.3 µsec, thus the calculated depth is $$L_1 = L_2 = d = \frac{v_c \times t}{2} = \frac{1500 \text{ m/s} \times 1.3 \text{ µsec}}{2} = 0.975 \text{ mm}$$

Figure 54:
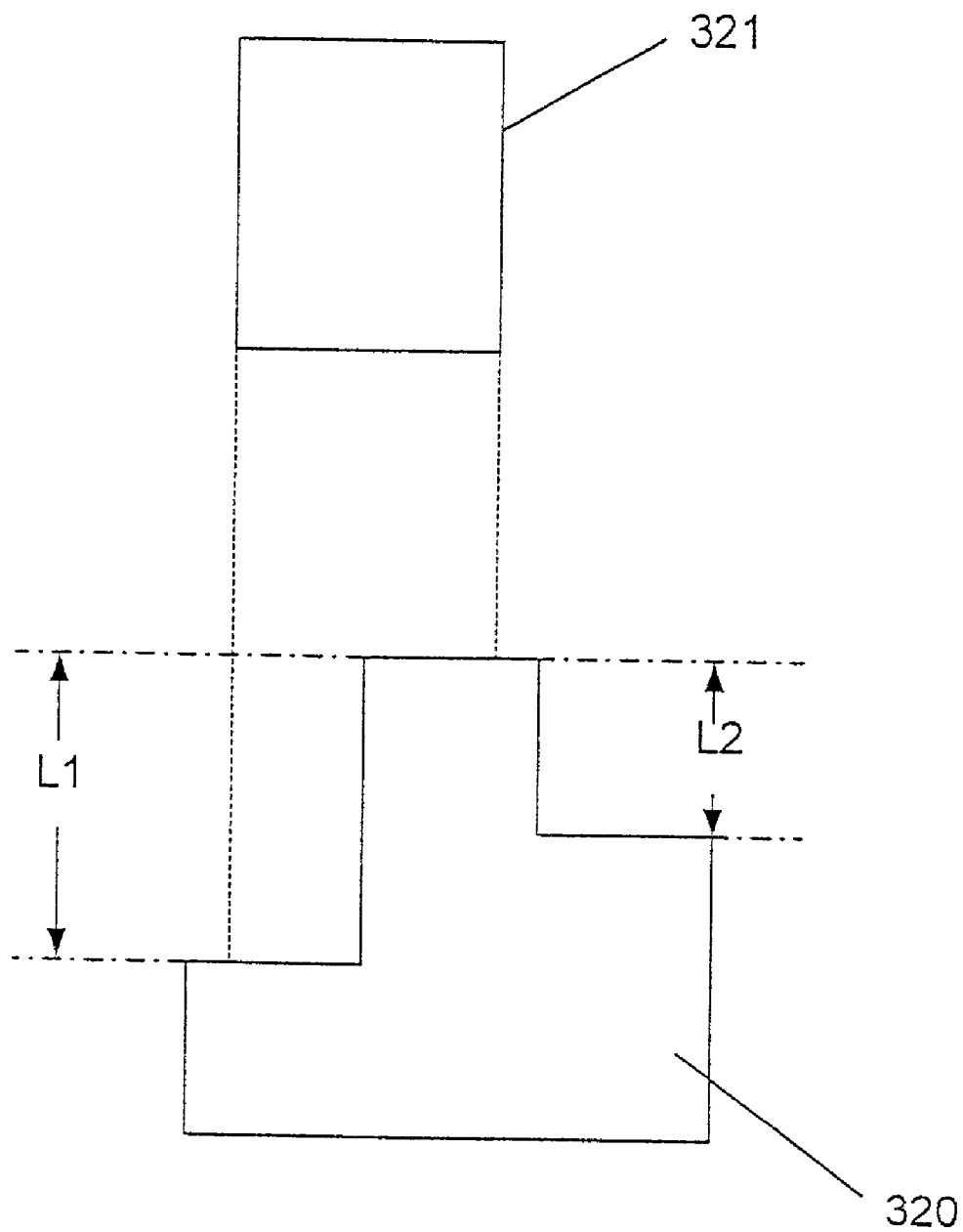
FIG. 54 schematically illustrates a two-step reflector.

Another procedure that forms a part of the present invention uses a displacement algorithm. This algorithm can be implemented only on two (or more) step (or bore) reflectors, i.e. a minimum of three echoes is required. In this embodiment, the reflector is built with different size step depths. If the emitted transducer spot falls on only some of the steps, then only some of the echoes will be received. The following example, described with reference to the step construction of FIG. 54, reveals the basis of the algorithm. FIG. 54 shows a two-step reflector 320 having two distinct step depths $L_1 \neq L_2$. The transmitting/receiving transducer is designated by the numeral 321.

For alignment detection, it is necessary to receive three echoes. In FIG. 54, the transducer is placed left of the aligned position. Therefore only two-echoes are received. Since the displacement algorithm calculates that the distance between the echoes is $L_1$, the algorithm will suggest to the operator to displace the transducer to the right until three echoes are received.

Figure 55A:
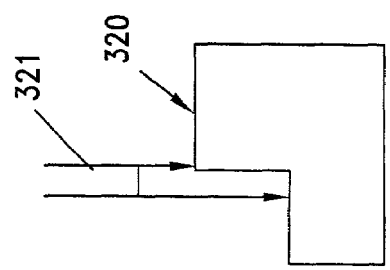
FIGS. 55A–55F schematically illustrate an alignment procedure.
Figure 55B:
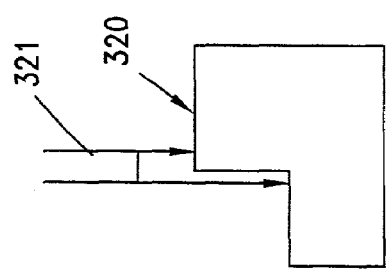
Figure 55C:
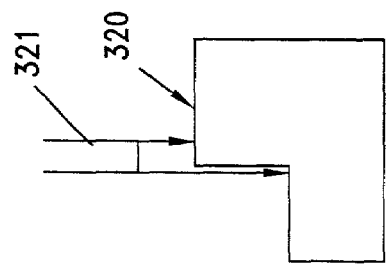

FIGS. 55A through 55F further illustrate the principles of the alignment procedure. In FIGS. 55A, 55B, and 55C a two-echo (one-step) reflector of the invention 320 is irradiated by a transducer 321.

Figure 55D:
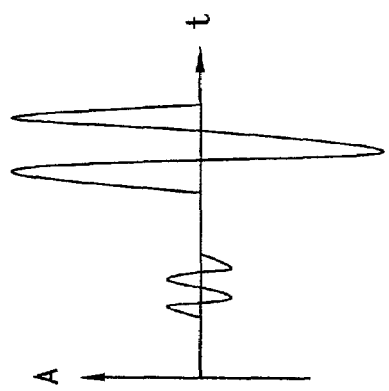
Figure 55E:
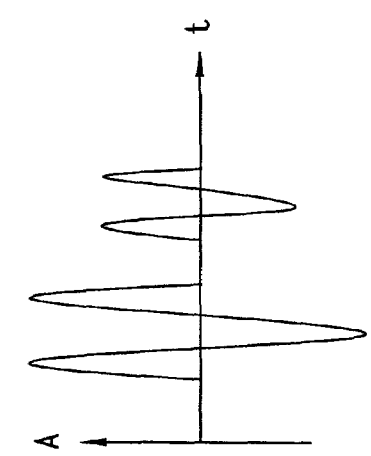
Figure 55F:
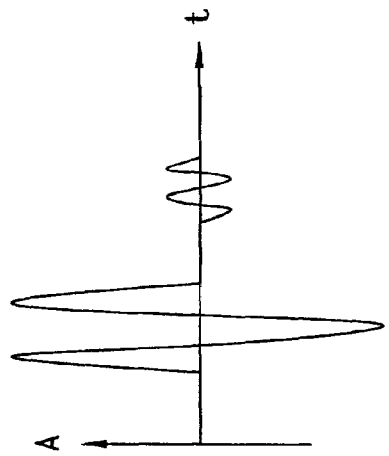

FIG. 55B shows the relative positions of the transducer and reflector when the system is aligned. In FIG. 55E, which schematically shows the corresponding received signal, a fixed relationship exists between the echoes from the two reflecting surfaces. In FIG. 55A, the transducer has "overshot" alignment and, as shown in FIG. 55D, the required ratio between the two-echoes does not exist, i.e. the echo from the farthest surface is much larger than from the closest surface. FIGS. 55C and 55F illustrate the situation in which the transducer has "under-shot" alignment. It should be clear to the skilled engineer how the operator can use this information to steer the elements into the correct alignment. The above procedure is the basis for the development of a process to automate the alignment procedure.

Figure 47:
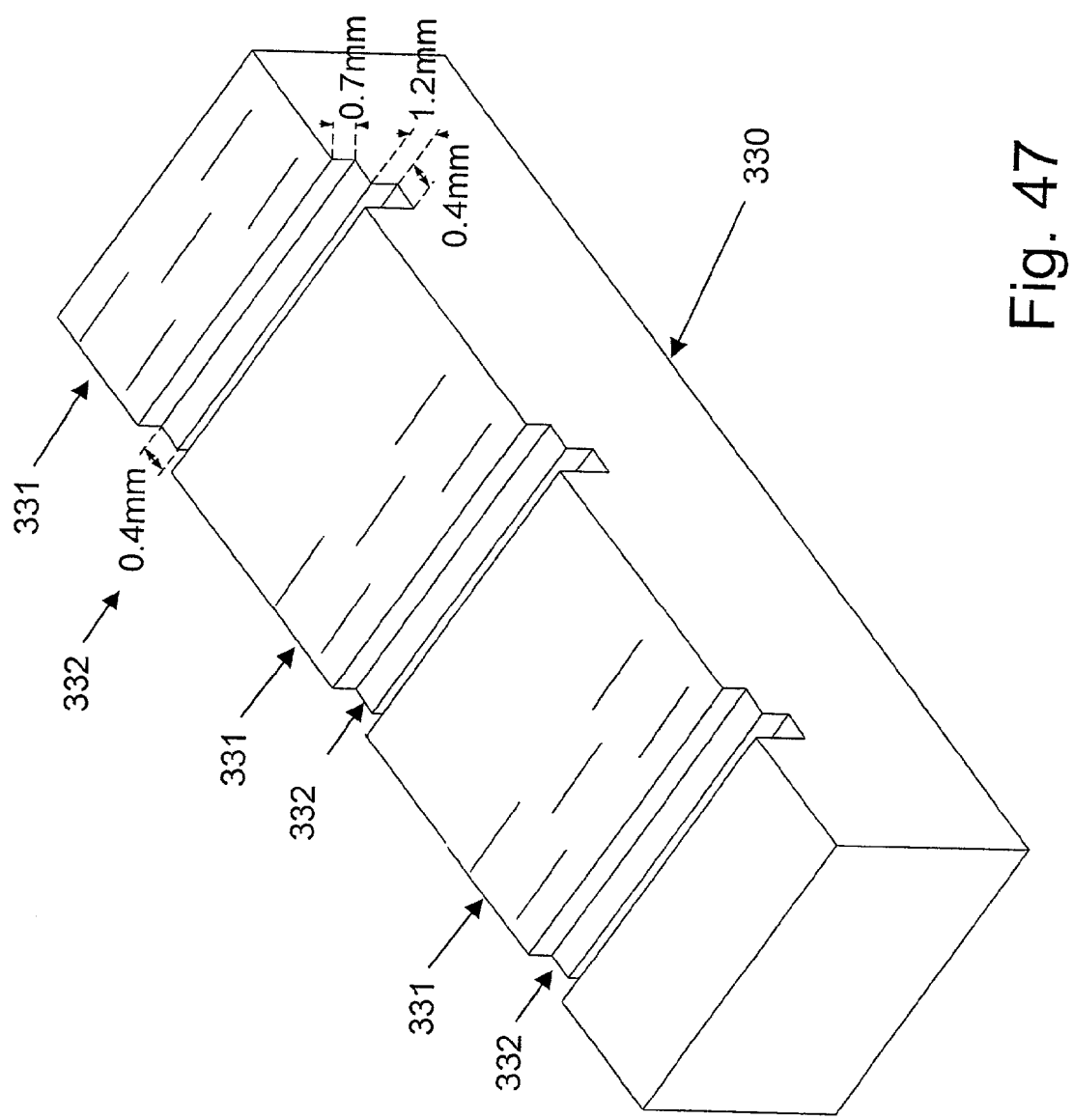
FIG. 47 schematically shows two-step reflectors on a staple cartridge.

FIG. 47 schematically shows the preferred embodiment of the invention applied to a stapler which may be, e.g., that disclosed above. The stapler cartridge is generally shown at 330. Numeral 331 designates each of the three arrays of five staples each and numeral 332 designates two-step reflectors that are created into the surface of the cartridge next to each array of staples. As an example, typical measurements are shown on one of the reflectors. In this embodiment, the transducer is located on the distal tip of the endoscope at, for example, one of the positions 114 in FIG. 17B. Many other possibilities exist for constructing the reflectors as an integral part of the cartridge. For example, in another preferred embodiment of the invention, the reflectors are created as a set of steps that protrude above the surface of the cartridge. The implementation of the methods of this invention in the case of four-way endoscopes has to be somewhat different then those for two-way endoscopes in order to include the effects of rotation. In one preferred embodiment of the invention for use with a four-way endoscope, a reflector is mounted on the cartridge and a transducer on the distal tip. If the distal tip is rotated relative to the reflector, then (as long as the transducer is not located at the center of the distal tip) the transmitted beam will not fall on the steps of the reflector and the reflected beams will not be detected.

Another preferred embodiment of the invention, for use with a four-way endoscope, makes use of two reflectors mounted on the cartridge. In this embodiment, the reflectors are mounted perpendicularly to each other. The depths of the steps of the two reflectors are different. Therefore it is possible to determine which of the reflectors is being irradiated by the transmitted beam. This information is incorporated into an algorithm to correct for the rotation and to bring the parts of the stapler into proper alignment.

In designing the reflecting elements employed in the above-described embodiments of the invention, several factors have to be taken into consideration. Among these considerations are the following:

1. The probability that echoes, with a certain time difference between them and with a certain amplitude relation, will be reflected back from the ambient area is very small. The probability is greatly reduced by using more than two echoes making the constructions that give rise to three echoes the preferred embodiments of the invention.
2. In order to receive high amplitude echoes, it is best to use step widths as wide as possible. In two-echo (one-step) reflectors the step width is unlimited. However, in three or more echo reflectors, it is very important that the accumulation of all step widths not exceed the beam width to insure that there are reflections from all of the surfaces when alignment is achieved. On the other hand, making the step widths excessively narrow will result in very weak amplitude reflections.
3. The height of the steps (i.e. the distances between the reflecting layers) must be more than the resolution of the measuring system i.e, it is best to design the step depth such that it is greater than the length of the echo duration multiplied by the speed of sound in the tissue (for example 1500 m/s) divided by 2. It is possible to work with depths less than these; but, in this case, the reflected echoes will be partially overlapping causing lower signal-to-noise ratio
4. In some cases it is possible to surround the reflecting surfaces with absorbing material and thus, to increase the contrast of the reflector.
5. One of the possible sources of inaccuracy in the use of multi-step reflectors is the air gaps that can be created if the tissue is not in firm contact with all of the reflecting surfaces. One possible solution to this problem is to fill the gaps with medical ultrasonic gel. The conventional gel is often displaced during insertion of the endoscope, therefore it is preferred to fill the steps with a hard or flexible material having acoustical matching to the tissue. In this case no air gaps are created and therefore no error will occur in the measurements. A suitable material for this purpose is, for example well known industrial silicon or commercially available bio-compatible silicon products well known in the art.
6. Transducers with many different characteristics can be employed in the various embodiments of the invention described above. An example of a transducer used in the preferred embodiment of the invention is a single element, directional transducer that is capable of both transmitting and receiving. The diameter of the transducer is one mm and its length is two mm. The connecting cable has a diameter of less than one mm. The device has a center frequency of 11 MHz and bandwidth (−6 dB) of 60%. The transducer is used in direct contact with the tissue and no matching layer is needed. The transducer is custom made for the Applicant by Blatek Inc., State College, Pa., USA.

The ultrasound circuit used to perform the distance and alignment measurements of the invention will now be described. The circuit can use either A-mode (one transducer for transmitting and receiving) or C-mode (two different transducers are used one for transmitting and one for receiving) scanning, without the imaging part. For the sake of brevity, the following description will be for A-mode but all the same principles can be implemented with the C-mode using the essentially the same electronic components and circuit.

Figure 48:
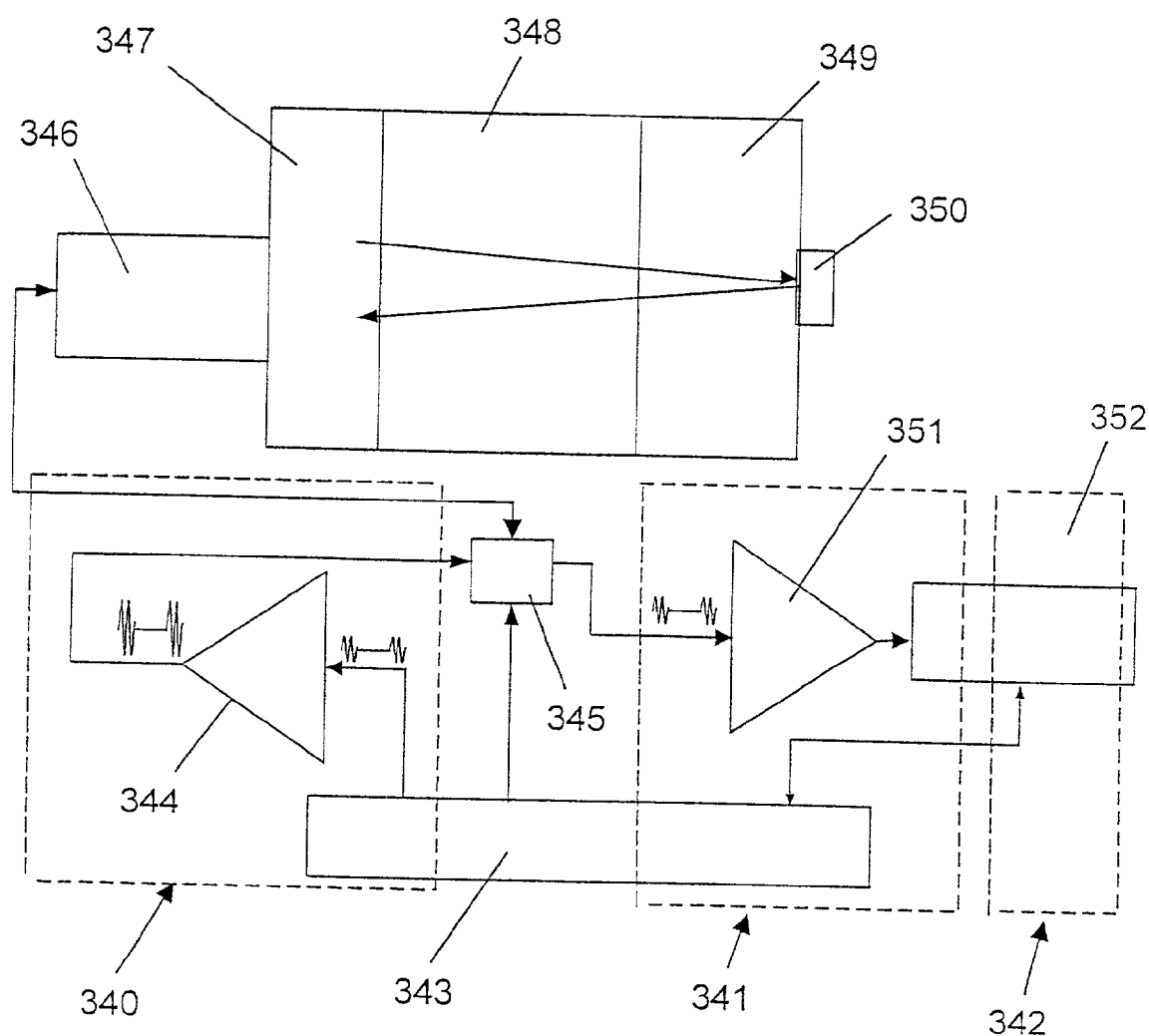
FIG. 48 is a block diagram of the ultrasound system according to another preferred embodiment of the invention.

FIG. 48 is a block diagram of the ultrasound circuit according to another preferred embodiment of the invention, which is composed of three interconnected units: the transmitter (generally shown at 340), the receiver 341, and the digitizing, signal processing (DSP), distance and alignment unit 342. Numeral 343 represents the timing and control circuits and the input/output (I/O) interfaces. The timing circuit generates one pulse or burst of pulses of frequency of, for example, 11 MHz and with a pulse repetition rate (or frequency) (PRF) of 100 Hz. These pulses are amplified by a power amplifier 344 and applied through a transmit/receive (T/R) switch 345 to a transducer or array of transducers 346 that is, for example capable of both transmitting and receiving ultrasonic signals (equivalent to 290 in FIG. 37, where the transducer is a transmitter only). The transducer converts the electric signal into an ultrasonic signal. In order to integrate the transducer with the endoscope, the dimensions of the transducer must be very small. In a preferred embodiment of the invention, these dimensions are 1 mm diameter and 2 mm length and the cable that connects the transducer to the electric circuit is a coaxial wire with less than 1 mm diameter. The transducer lobe is directional and since it works within the Fresnel zone it is essentially collimated. The emitted sound wave penetrates the boundary of the stomach 347, then passes through the fat tissue 348, and finally enters the esophagus 349. In the esophagus, the sound wave falls upon a very good reflector 350 (or, in C-mode, a receiving transducer equivalent to 261 in FIG. 35) that is mounted on (or is part of) the staple cartridge. The reflected signal returns along the same path until the transducer receives it and transforms the ultrasonic signal to an electrical signal. The electric signal then passes through the T/R switch 345 to amplifier 351, which amplifies the return signal from the transducer. The amplified signal then passes to an A/D device (located at 352, which also represents elements of the system that perform the DSP functions) to be digitized in order to carry out digital signal processing.

The DSP module has two main functions:
i) To measure the distance between the distal tip and the anvil
ii) To confirm alignment between the distal tip and the anvil.

The digitization must meet the well-known Nyquist criteria but, because the signal is narrow band, it is possible to use under-sampling and thus decrease calculation loads and omit some electrical circuits.

Figure 49:
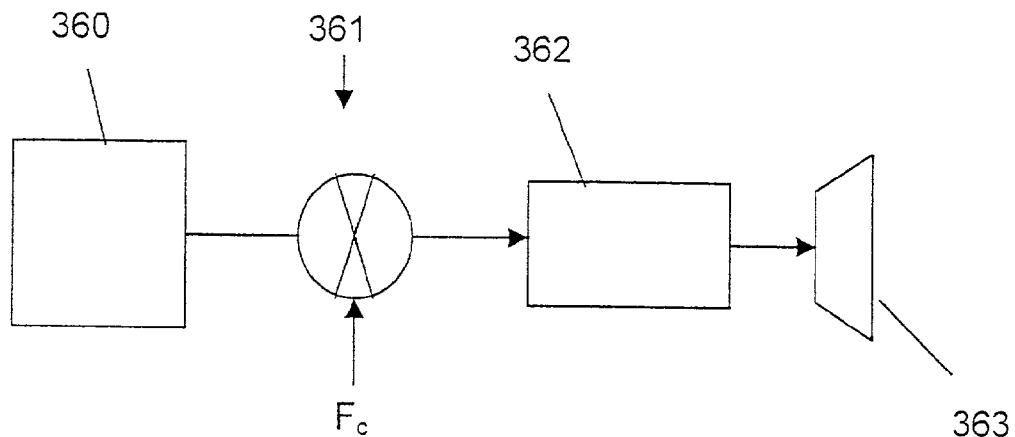
FIG. 49 schematically illustrates the transmitter portion of the ultrasound system.

The three main units of the ultrasound system of FIG. 48 will now be discussed in more detail. The transmitter unit is schematically shown in FIG. 49. The data bit generator and gate 360 are able to generate one pulse or bursts of data bits. They also determine the type of modulation of the carrier frequency Fc (which is a square or sinusoidal wave with an oscillation rate of, for example, 10.7 MHz) that is fed into the mixer 361. When transmitting one pulse only, the length of the pulse is determined by the transducer specification (in this example 100 nsec), and the pulse repetition frequency (PRF) is 100 Hz. By transmitting a burst of pulses or a random sequence of pulses or a modulated random burst of pulses it is possible to increase the reliability of the measurements and to work with very weak signals in a very noisy environment. The mixed (modulated) signal is transferred to the power amplifier 362 that filters and amplifies it before passing it to the transducer 363, which converts the electrical energy into ultrasonic energy.

Figure 50:
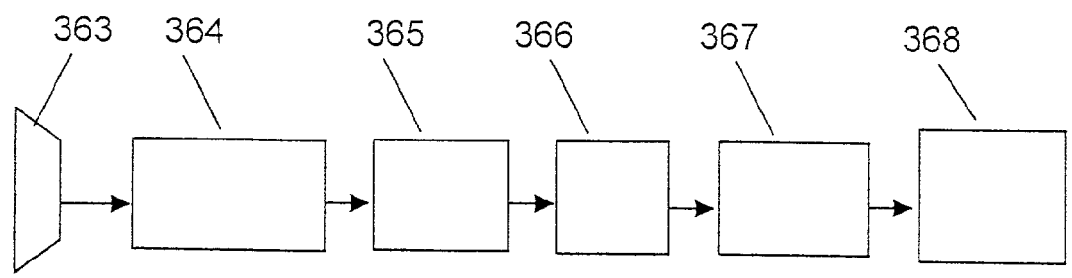
FIG. 50 schematically illustrates the receiver portion of the ultrasound system.

The receiver unit is schematically shown in FIG. 50. The ultrasonic wave that passes throughout all the tissues is received by the transducer 363, which converts the ultrasonic energy into electric energy. The signal is amplified by amplifier 364 and filtered by bandpass filter (or filters) 365 to eliminate any undesired frequencies. Then the signal is digitized with an analog-digital (A/D) unit 366 (which has, for example, 8 bit resolution and a sampling rate of 100 MHz). Since the sample rate is very high compare to the data transfer rate of the computer, then it is necessary to use a fast first-in-first out (FIFO) unit 367, that stores the data until it is passed to the main memory 368 of a personal computer (PC).

The digitization module is a PC card that includes an A/D unit with a sample rate of 50–100 MHz. When transmission is initiated, the A/D unit simultaneously starts to sample and the data is collected in the FIFO unit for about 20 μs (which is equivalent to a distance of about 3 cm) and then the data is transferred to a buffer in the computer main memory.

The preferred method for implementing the distance calculations involves the use of the following correlation algorithm. The sampled data in the buffer is cross-correlated with a predefined signal pattern that is stored in the computer memory.

Figure 51A:
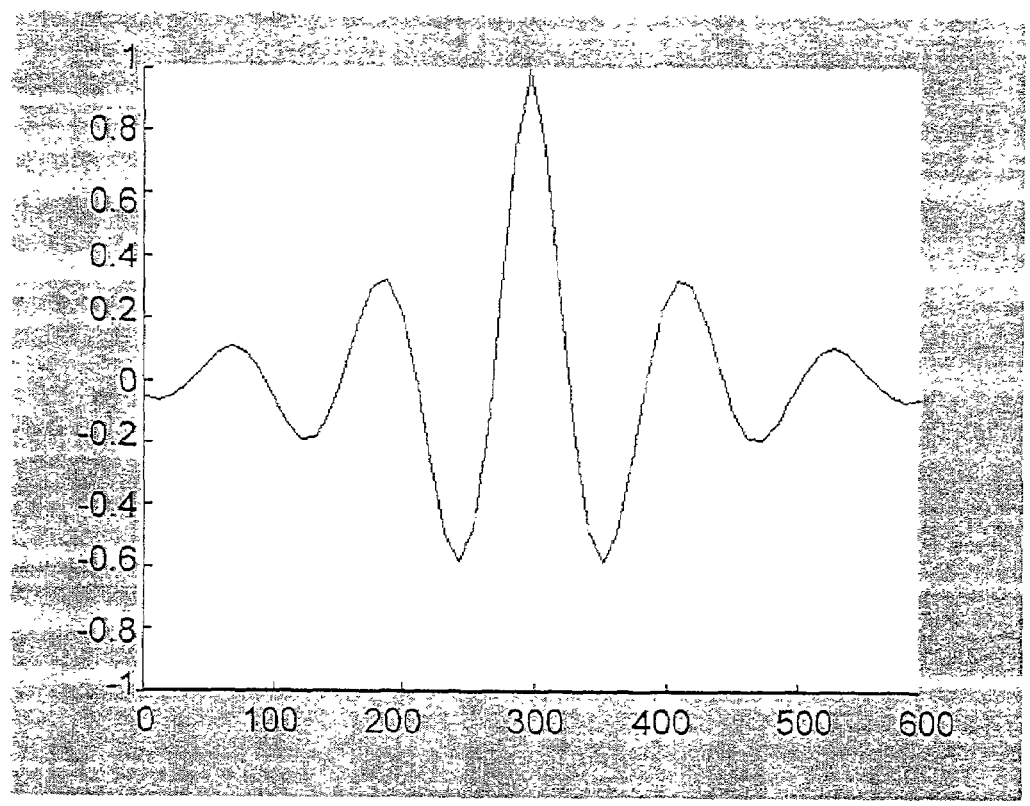
FIGS. 51A and 51B are reproductions of photographs of computer screens showing predefined reference signals.

The reference signal can be created in two ways. The first method makes use of the fact that it is possible to synthesize or to write a function that will generate the pattern of the reflected echo. An example of a function that generates such a reference signal is:

ref $(t)=Ie^{-\tau t}\cos(\omega_d t-\theta) t \geq 0$, ref $(t)=Ie^{\tau t}\cos(\omega_d t-\theta) t \leq 0$ where, $\tau$ is the dumping factor derived from the transducer specification, $\omega_d$ is the dumped natural frequency derived from the transducer specifications, and $\theta$ is a phase correction, if necessary (William W. Seto, Acoustics, Schaum's Outline Series, McGraw-Hill Inc., USA, 1971). FIG. 51A is a reproduction of a computer screen showing an example of a synthesized reference signal calculated using the above formula.

Figure 51B:
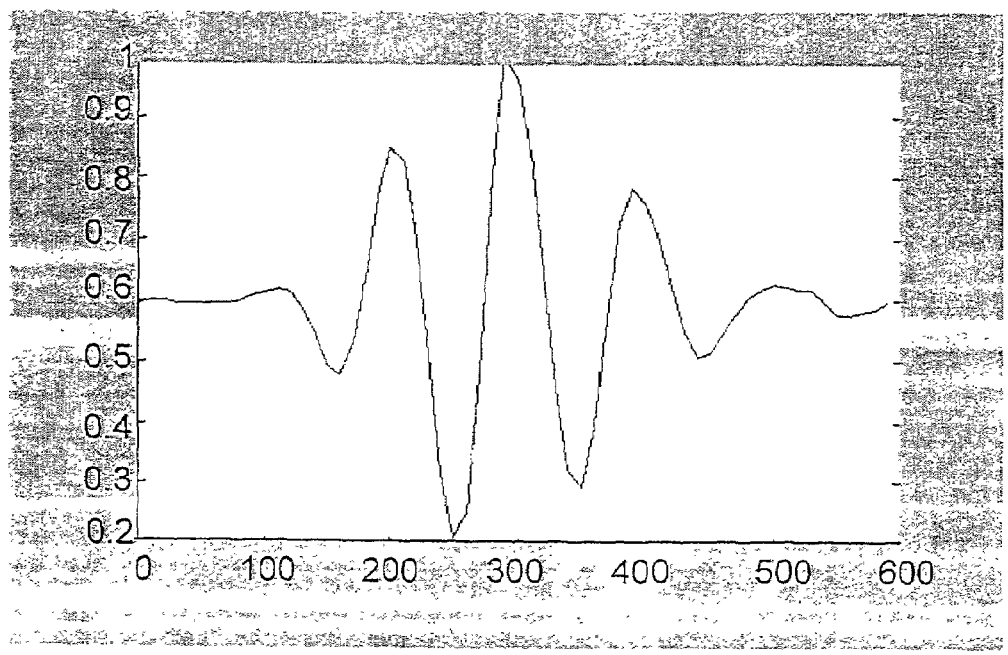

In the second method an actual echo is sampled and stored in the computer memory for use as the reference signal. The second method is preferred, since it includes exactly the characteristics of all of the transmitting and receiving system including those of the transducer. Thus if, for example, the transducer (or any other component of the system) is replaced with another part having slightly different characteristics; it is possible to store the exactly expected reference signal in the computer memory by making a simple calibration measurement (for example in water). FIG. 51B is a reproduction of a computer screen showing an example of a pre-measured reference signal. In FIGS. 51A and 51B. the horizontal axis represents time measured in nanoseconds. A cross-correlation result is obtained from the following formula:

$$r_{ref,sig}(1) = \sum_{n=1}^{N=1} ref(n-1) \cdot signal(n) \ 0 \leq 1 \leq N-1$$

where $r_{ref,sig}(1)$ is the cross correlation result, ref(n–1) is the reference signal and signal (n) is the received signal, N=length(signal)–length(ref).

The index of the element that contains the maximum in the correlation buffer ($r_{ref,sig}(1)$i corresponds to the place where the reference signal and the received signal best match. The time of arrival of the echo is calculated by $T_{arrival}$=(Buffer_index*1/Ts)/2, where Buffer_index is the index of the buffer where the maximum correlation is obtained and Ts is the sampling frequency.

It follows from the above that the accuracy of the measurement is determined by the sampling frequency, i.e., the error in the time measurement will be $\pm 1/T_s$. For example, if the sample rate is 100 MHz. Then, $$\frac{1}{100 \text{ MHz}} \times 1500 \text{ m/s} = 15 \text{ μm}$$

i.e., the accuracy in the distance is ±15 μm.

Figure 52A:
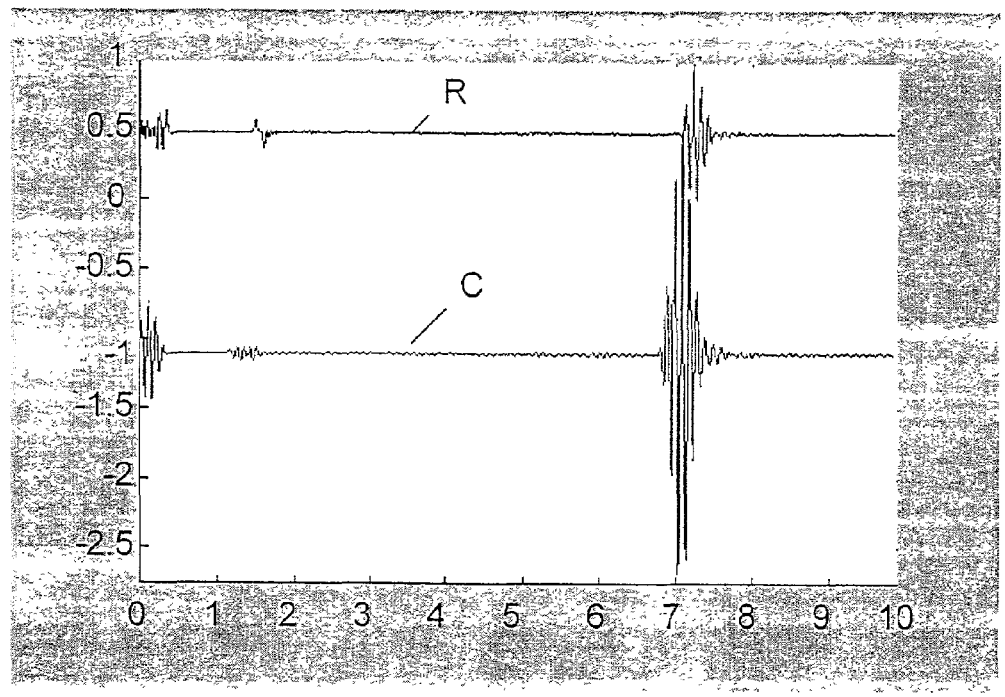
FIG. 52A is a reproduction of a photograph of a computer screen showing a measured received signal and a correlation result between the received signal and the reference signal of FIG. 51B.
Figure 52B:
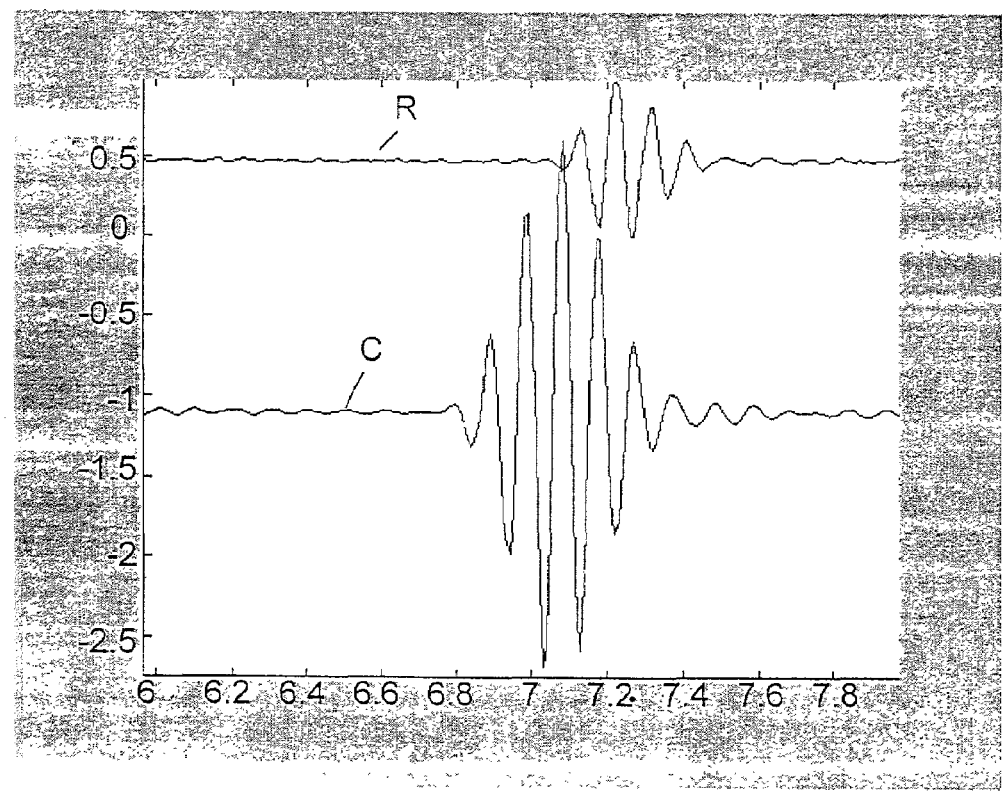
FIG. 52B is an enlargement of a section of FIG. 52A.

FIG. 52A is a reproduction of a computer screen showing the correlation results (lower curve-C) for a typical buffer between the received echo from a reflector (upper curve-R) and the pre-measured reference curve of FIG. 51B. FIG. 52B is an enlargement of part of FIG. 52A, showing more detail of the received signal and correlation results. The maximum of the correlation occurs exactly at the beginning of the received signal. In FIGS. 52A and 52B, the horizontal axis represents time measured in microseconds.

The alignment algorithm uses the distance measurement algorithm as one of the criteria for alignment detection. The following example is for a one-step (two-echo) reflector, but it can easily be expanded to cover the cases of reflectors having three or more echoes. The signal received in the buffer is correlated with the reference signal. Then the algorithm searches for the location of two maxima of the correlation. The distance between these two maxima must equal the depth of the step. If this criterion is not met then the transducer and reflector are not aligned.

If the distance between the maxima is correct, then the energy of the two echoes is compared to either meet the attenuation and area cross-section relationships heretofore presented or a pre-measured relation known from a calibration measurement. If these relations are not satisfied, then the alignment is not correct.

Figure 53:
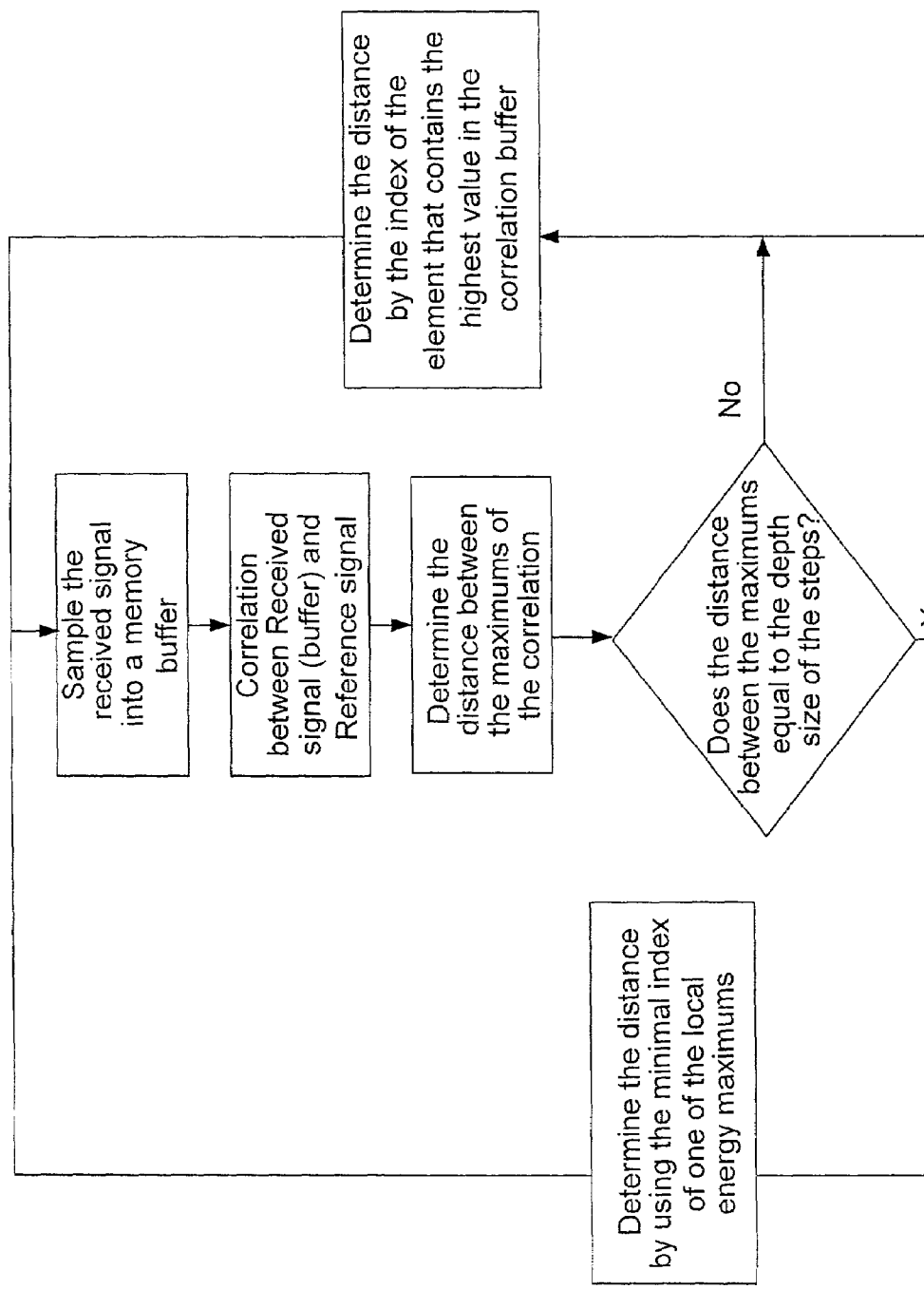
FIG. 53 is a flow chart of the alignment algorithm.
Figure 53:
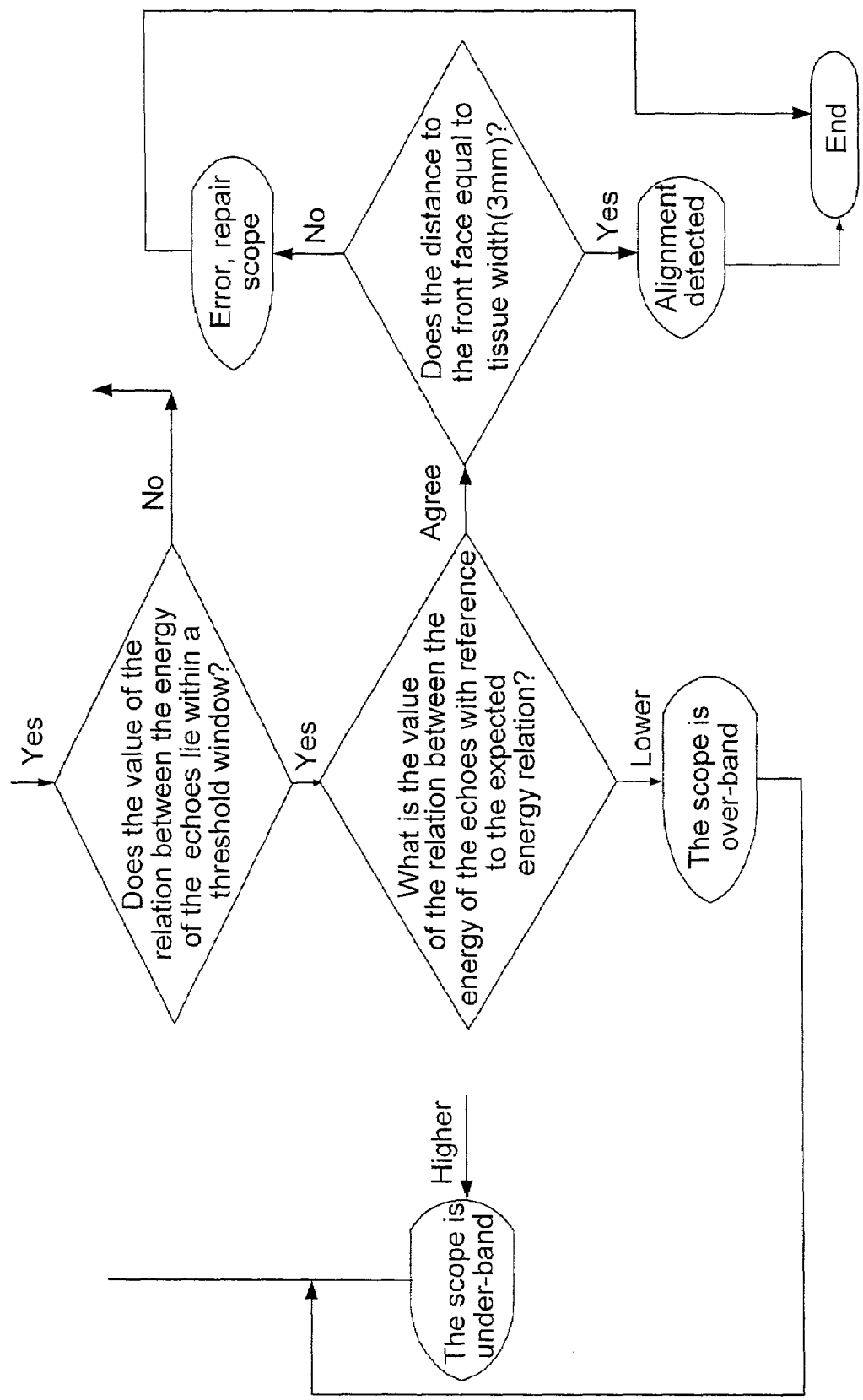

FIG. 53 is a flow chart of an alignment algorithm. The alignment is considered to be correct if, and only if, the echoes are measured at the distance that corresponds to the depth of the step and satisfy the amplitude relations.

In order to reduce the time of calculation, it is possible to find the maxima in the received buffer instead of the correlation maxima. However, in this case, errors occur when random noise with high amplitude occurs. Therefore in a preferred embodiment of the invention the calculation is made using the correlation peaks of the energy (equivalent to the integration of the intensity) and not by using the maxima from the received buffer.

While embodiments of the invention have been described by way of illustration, it will be understood that the invention can be carried out by persons skilled in the art with many modifications, variations and adaptations, without departing from its spirit or exceeding the scope of the claims.

The invention claimed is:

1. An endoscopic device for carrying out a partial fundoplication, comprising:
   a distal bending portion having a distal tip and a flexible portion suitable to be positioned in extended shape within the esophagus of a subject;
   a positioning assembly comprising two separate elements, one of which is located on said distal bending portion, and the other on said flexible portion;
   a stapling assembly comprising a staple ejecting device, wherein said staple ejecting device is located on either said bending portion or on said flexible portion, said staple ejecting device being in working positioned relationship when said two separate elements of said positioning assembly are aligned; and
   circuitry for determining when said two separate elements of said positioning assembly are aligned.

2. An endoscopic device according to claim 1, wherein the stapling assembly further comprises an anvil, wherein either said anvil or said staple ejecting device is located on said bending portion, and the other is located on said flexible portion, said anvil and said staple ejecting device being in working positioned relationship when the two separate elements of the positioning assembly are aligned.

3. An endoscopic device according to claim 2, wherein the portion of the stapling assembly located on the distal bending portion is located on the distal tip.

4. An endoscopic device according to claim 2, wherein the stapling assembly comprises portions including a staple ejecting device and an anvil, wherein said staple ejecting device and said anvil are located longitudinally displaced from one another along the longitudinal axis of said endoscopic device, with at least a part of the flexible portion between them.

5. An endoscopic device according to claim 4, wherein the portions of the stapling assembly are in correct working relationship when one or more alignment/locking pins that are stored either in the staple ejecting device or the anvil are extended and engage and lock into receptacles that have been provided on the other portion of said stapling assembly.

6. An endoscopic device according to claim 5, wherein the alignment/locking pins can be extended and retracted from the portion of the stapling assembly in which they are stored.

7. An endoscopic device according to claim 6, wherein a dual rack and single pinion system is employed to provide the motion of the alignment/locking pins.

8. An endoscopic device according to claim 5, wherein the alignment/locking pins can be locked and released from the receptacles that are provided in the portion of the stapling assembly.

9. An endoscopic device according to claim 5, wherein two alignment/locking pins are provided.

10. An endoscopic device according to claim 5, wherein the alignment/locking pins are stored in the anvil.

11. An endoscopic device according to claim 5, wherein the flexible portion is an articulation section and wherein the alignment/locking pins are manufactured such that the pin tips can be broken by the force exerted by unbending the articulation section.

12. An endoscopic device according to claim 4, wherein either the staple ejecting device or of the anvil is located proximately to the proximal end of the flexible portion and the other portion of the stapling assembly is located proximately to the distal end of said flexible portion.

13. An endoscopic device according to claim 12, wherein the staple ejecting device is located proximately to the proximal end of the flexible portion and the anvil is located on the distal tip of said flexible portion.

14. An endoscopic device according to claim 4, wherein either the staple ejecting device or the anvil is located on the flexible portion of the endoscopic device and the other portion of the stapling assembly is located proximately to the distal end of said flexible portion.

15. An endoscopic device according to claim 4, wherein either the staple ejecting device or the anvil is located on the flexible portion.

16. An endoscopic device according to claim 4, wherein the flexible portion is an articulation section.

17. An endoscopic device according to claim 16, wherein the articulation section is a two-way articulation section.

18. An endoscopic device according to claim 16, wherein the articulation section is a four-way articulation section.

19. An endoscopic device according to claim 16, wherein activation of the articulation section causes the portions of the stapling assembly to be brought into correct working relationship.

20. An endoscopic device according to claim 4, wherein the staple ejecting device contains a staple cartridge containing one or a plurality of arrays of staples each array consisting of one or a plurality of staples.

21. An endoscopic device according to claim 20, wherein the arrays of staples are fired by staple pushers actuated by cams actuable by proximal mechanism.

22. An endoscopic device according to claim 20, wherein the staple cartridge is indexable after the firing of each of the arrays of staples by the action of a proximal actuating device.

23. An endoscopic device according to claim 20, wherein the number of the arrays of staples is three and the number of staples in each of said arrays is five.

24. An endoscopic device according to claim 20, wherein the staples of each array are arranged in three rows with the pinholes aligned with the middle row.

25. An endoscopic device according to claim 4, comprising safety means for disabling the operation of the staple ejecting device when the two separate portions of the stapling assembly are not aligned.

26. An endoscopic device according to claim 2, wherein the staple ejecting device is a staple cartridge, said endoscopic device comprising a transducer, that transmits only, or receives only, or both transmits/receives, mounted into either the anvil or said staple cartridge.

27. An endoscopic device according to claim 1, comprising safety means for disabling the operation of the staple ejecting device when the two separate elements of the positioning assembly are not aligned.

28. An endoscopic device according to claim 1, comprising viewing means.

29. An endoscopic device according to claim 28, wherein the viewing means comprise a video camera.

30. An endoscopic device according to claim 28, wherein the viewing means comprise illumination apparatus.

31. An endoscopic device according to claim 1, comprising one or more channels for supplying one or more of the following:
water and suction.

32. An endoscopic device according to claim 1, further comprising positioning markings to position a portion of the stapling assembly within the esophagus at a location of about 5–6 cm above the gastroesophageal junction, when said endoscopic device is in working position.

33. An endoscopic device according to claim 32, wherein the portion of the stapling assembly comprises the staple ejecting device.

34. An endoscopic device according to claim 10, wherein the anvil is essentially ring-like in shape.

35. An endoscopic device according to claim 32, wherein the portion of the stapling assembly is displaced along the axis of said endoscopic device by the action of a flexible threaded cable coupled with a female thread located in said portion of said stapling assembly.

36. An endoscopic device according to claim 35, wherein the flexible threaded cable is located within said endoscopic device, and is in contact with the female thread through a slit provided in said endoscopic device.

37. An endoscopic device according to claim 35, wherein the flexible threaded cable is embedded in said endoscopic device, and is in direct contact with the female thread of the portion of the stapling assembly.

38. An endoscopic device according to claim 35, wherein the flexible threaded cable is rotated using a micrometric assembly, thereby to displace the portion of the stapling assembly positioned within the esophagus by a controlled distance.

39. An endoscopic device according to claim 1, wherein the element of the positioning assembly located on the distal bending portion is located on the distal tip.

40. An endoscopic device according to claim 1, comprising two or more separate optical channels that produce two or more distinct views, each of said optical channels consisting of an objective lens and a means of capturing or viewing the image, wherein each objective lens is located at a different position along the length of said endoscopic device.

41. An endoscopic device according to claim 40, in which each of said distinct multiple views may be formed by a single optical channel to produce a monocular view, or by multiple optical channels to produce a binocular or stereoscopic view.

42. An endoscopic device according to claim 41, in which the field of view of each of said optical channels may be of any suitable shape.

43. An endoscopic device according to claim 42, wherein the field of view of each of said optical channels is either circular or rectangular.

44. An endoscopic device according to claim 42, wherein the field of view of each of said optical channels has an angular view of up to more than 180 degrees or more.

45. An endoscopic device according to claim 40, in which the components of said optical channels and said display apparatus are chosen such that said endoscopic device can operate in either the visible, ultraviolet, infrared, or x-ray portions of the electromagnetic spectrum.

46. An endoscopic device according to claim 40, wherein each channel comprises one or more of the following elements: a) an optical relay system; b) an occular; and c) a coupling lens suitable to deliver the image acquired by said objective lens to an image sensor and display apparatus.

47. An endoscopic device according to claim 46, in which said objective lens, occular, and coupling lens have either fixed focal length, multiple focal lengths, or variable focal lengths.

48. An endoscopic device according to claim 40, in which the center of each of said distinct views is at an angle of between 0 and 180 degrees with respect to the mechanical axis of said endoscopic device.

49. An endoscopic device according to claim 1 wherein the staple ejecting device is a stapler cartridge comprising one or more reflectors of ultrasonic waves is created on or within or as an integral part of the surface of said cartridge.

50. A method for carrying out an endoscopic partial fundoplication of the fundus of the stomach of a patient, comprising the steps of:
(One) providing an endoscopic device comprising a bending portion and a flexible portion, a positioning assembly comprising two separate elements, and a stapling assembly comprising a staple ejecting device;
(Two) moving the distal tip of said endoscopic device so as to engage said fundus of said patient and to displace it toward the lower part of the esophagus;
(Three) bringing said stapling assembly into working positioned relationship by aligning said two separate elements of said positioning assembly, wherein one of said elements is located on the bending portion and the other on the flexible portion of said endoscopic device;
(Four) determining when said two separate elements of said positioning assembly are aligned by maximizing a signal resulting by bringing them into close positioned relationship, which is received at a signal receiving and analyzing circuit cooperating with said positioning assembly;
(Five) ejecting a plurality of staples from said staple ejecting device, thereby to connect the tissue between them; and
(Six) rotating said endoscopic device relative to the axis of said esophagus and repeating steps (c) through (e) for as many times as needed to achieve the desired partial fundoplication.

51. A method according to claim 50, wherein the stapling assembly further comprises an anvil, wherein either said anvil or said staple ejecting device is located on the bending portion, and the other is located on the flexible portion.

52. A method according to claim 51, wherein the distance between the staple ejecting device and the anvil is between about 0.5 and 1.5 cm.

53. A method according to claim 50, wherein the signal resulting by bringing the two separate elements of said positioning assembly into close positioned relationship is maximized by measuring a physical parameter which is a function of the distance.

54. A method according to claim 50, wherein the signal resulting by bringing the two separate elements of said positioning assembly into close positioned relationship is maximized by correlating it to a measured physical parameter.

55. A method for positioning the endoscopic device of claim 1 in pre-aligned working position, comprising the steps of:
(One) introducing said endoscopic device through the mouth of a patient and locating the position of the gastroesophageal junction;
(Two) determining the distance from a reference point located on said endoscopic device, and said gastroesophageal junction;
(Three) introducing said endoscopic device into the stomach to a distance below said gastroesophageal junction sufficient to permit the distal tip to be flexed into a position where the fundus is pushed toward the esophagus;
(Four) locking said endoscopic device such that it cannot move relative to the axis of said esophagus;
(Five) determining the position of the portion of the stapling assembly positioned within said esophagus by using its original axial location, said distance determined in step (two), and the radius of curvature of the distal portion of said endoscopic device; and
(Six) displacing said portion of the stapling assembly so as to position it in the range of about 5–6 cm above said gastroesophageal junction.

* * * * *